United States Patent
de Leeuw et al.

(10) Patent No.: US 10,961,214 B2
(45) Date of Patent: Mar. 30, 2021

(54) SMALL MOLECULE LIPID II INHIBITORS

(71) Applicants: Erik de Leeuw, Baltimore, MD (US); Alexander MacKerell, Baltimore, MD (US); Steven Fletcher, Baltimore, MD (US); Jamal Chauhan, Baltimore, MD (US)

(72) Inventors: Erik de Leeuw, Baltimore, MD (US); Alexander MacKerell, Baltimore, MD (US); Steven Fletcher, Baltimore, MD (US); Jamal Chauhan, Baltimore, MD (US)

(73) Assignee: UNIVERSITY OF MARYLAND, BALTIMORE, Baltimore, MD (US)

(*) Notice: Subject to any disclaimer, the term of this patent is extended or adjusted under 35 U.S.C. 154(b) by 0 days.

(21) Appl. No.: 16/064,276

(22) PCT Filed: Dec. 20, 2016

(86) PCT No.: PCT/US2016/067774
§ 371 (c)(1),
(2) Date: Jun. 20, 2018

(87) PCT Pub. No.: WO2017/112668
PCT Pub. Date: Jun. 29, 2017

(65) Prior Publication Data
US 2019/0002426 A1    Jan. 3, 2019

Related U.S. Application Data

(60) Provisional application No. 62/270,184, filed on Dec. 21, 2015.

(51) Int. Cl.
| | | |
|---|---|---|
| C07D 309/34 | (2006.01) |
| A61P 31/04 | (2006.01) |
| A61K 31/35 | (2006.01) |
| C07D 455/04 | (2006.01) |
| C07D 405/06 | (2006.01) |
| C07D 403/06 | (2006.01) |
| C07D 471/06 | (2006.01) |

(52) U.S. Cl.
CPC ............ C07D 309/34 (2013.01); A61P 31/04 (2018.01); C07D 403/06 (2013.01); C07D 405/06 (2013.01); C07D 455/04 (2013.01); C07D 471/06 (2013.01)

(58) Field of Classification Search
CPC .................................................. C07D 309/34
See application file for complete search history.

(56) References Cited

U.S. PATENT DOCUMENTS

| | | |
|---|---|---|
| 2,461,484 A | 2/1949 | Thompson |
| 3,250,615 A | 5/1966 | Van Allen et al. |
| 6,124,342 A * | 9/2000 | Okamoto ............... A61K 31/33 514/432 |
| 8,796,323 B2 | 8/2014 | Leeuw et al. |
| 9,351,963 B2 | 5/2016 | Leeuw et al. |
| 2013/0331413 A1 | 12/2013 | De Leeuw et al. |
| 2014/0308317 A1 | 10/2014 | Fan et al. |

FOREIGN PATENT DOCUMENTS

| | | |
|---|---|---|
| EP | 0024169 A2 | 2/1981 |
| EP | 0659407 A1 | 6/1995 |

OTHER PUBLICATIONS

Chauhan et al. PLOS One, p. 1-19 and Supplemental Material . (Year: 2016).*
Okamoto et al. Chemical Abstracts, vol. 123, No. 221957 (Abstract for EP 659407). (Year: 1995).*
Boiko et al Chemical Abstracts, vol. 108,No. 7484 (abstract for Ukrainskii Khimicccheskii Zhurnal, 53(4) 412-16) (Year: 1987).*
ISA/US, "International Search Report and Written Opinion for the corresponding PCT application PCT/US2016/06774", dated Feb. 17, 2017, pp. 1-8.

(Continued)

*Primary Examiner* — Emily A Bernhardt
(74) *Attorney, Agent, or Firm* — Wolter Van Dyke Davis, PLLC; Martha Cassidy; Eugene J. Molinelli

(57) ABSTRACT

Newly synthesized derivatives of BAS00127538 have been discovered to possess antibiotic activity and to combat resistant bacterial strains. Compounds and pharmaceutical compositions containing these compounds are described, and are based on a generic scaffold structure. Synthetic methods and methods of using the compounds also are described. Preferred compound 6jc48-1 ((E)-2,4-bis(4-bromophenyl)-6-(4-(dimethyl-amino)styryl)pyrylium boron tetrafluoride salt) binds to Lipid II with high affinity, has markedly reduced cytotoxicity than BAS00127538, and retains activity against drug-resistant strains of *Enterococci*. It is stable in plasma, has dramatically improved pharmacokinetic and pharmacodynamics properties, and possesses in vivo efficacy in a mouse model of sepsis.

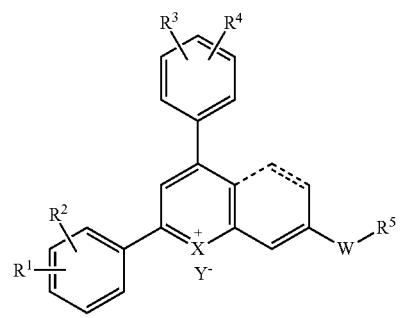

22 Claims, 13 Drawing Sheets

(56) References Cited

OTHER PUBLICATIONS

Allen N., et al, "Inhibition of peptidoglycan biosynthesis in vancomycin-susceptible and -resistant bacteria by a semisynthetic glycopeptide antibiotic", Antimicrobial Agents and Chemotherapy, vol. 40, Issue 10, pp. 2356-2362 (1996).
Aqvist J,. et al, "A new method for predicting binding affinity in computer-aided drug design", Protein Engineering, vol. 7, Issue 3, pp. 385-391 (1994).
Breukink E., et al, "Use of the cell wall precursor lipid II by a pore-forming peptide antibiotic", Science, vol. 286, pp. 2361-2364 (1999).
Breukink E., et al, "Lipid II is an intrinsic component of the pore induced by nisin in bacterial membranes", J of Biological Chem, vol. 278, Issue 22, pp. 19898-19903 (2003).
Breukink E., et al, "Lipid II as a target for antibiotics", Nature reviews drug discovery, vol. 5, Issue 4, pp. 1-12 (2009).
De Leeuw F, et al, "Functional Interaction of human neutrophil peptide-1 with the cell wall precursor lipid II", Febs Lett, vol. 548, Issue 8, pp. 1543-1548 (2010).
De Leeuw E., "Efficacy of the small molecule inhibitor of lipid II BAS00127538 against Acinetobacter baumannii", Design Drug Development and Therapy, vol. 8, pp. 1061-1064 (2014).
Den Blaauwen T., et al, "Bacterial cell division proteins as antibiotic targets", Bioorganic chem, vol. 55, pp. 27-38 (2014).
Essig A., et al, "Copsin a novel peptide-based fungal antibiotic interfering with the peptidoglycan synthesis", J Biological Chem, vol. 289, Issue 50, pp. 34953-34964 (2014).
Fletcher S., et al, "Structure-activity exploration of a small-molecule lipid II inhibitor", Drug Design Development Therapy, vol. 9, pp. 2383-2394 (2015).
Ganz T., "Defensins: antimicrobial peptides of innate immunity", Nature Reviews, vol. 3, pp. 710-720 (2003).
Munch D., et al, "Identification and in vitro analysis of the GatD/MurT enzyme-complex catalyzing lipid II amidation in *Staphylococcus aureus*", PLoS, vol. 8, pp. 1-11 (2012).
Oeemig J., et al, "Eurocin a new fungal defensin", J Biological Chem, vol. 287, Issue 50, pp. 42361-42372 (2012).
Oppedijk S., et al, "Hit 'em where it hurts: the growing and structurally diverse family of peptides that target lipid II" Biochem and Biophys, pp. 947-957 (2016).
Sass V., et al, "Human B-defensin 3 inhibits cell wall biosynthesis in staphylococci", Infection and Immunity, vol. 78, Issue 6, pp. 2793-2800 (2010).
Schmitt P., et al, "Insight into invertebrate defensin mechanism of action", J Biological Chem, vol. 285, Issue 38, pp. 29208-29216 (2010).
Schneider T., et al, "Plectasin a fungal defensin targets the bacterial cell wall precursor lipid II", Science, vol. 328, pp. 1168-1172 (2010).
Van Heijenoort J., "Lipid intermediates in the biosynthesis of bacterial peptidoglycan", Microbiol and molecular biol. rev., vol. 71, Issue 4, pp. 620-635 (2007).
Varney K., "Turning defense into offense: defensin mimetics as novel antibiotics targeting lipid II", PLoS, vol. 9, Issue 11, pp. 1-14 (2013).
Schneider T, et al, "Lipid II and other bactoprenol-bound cell wall precursors as drug targets", Curr. Op. Investigational Drugs, 2010, vol. 11, pp. 157-164.
Gavrilyuk, I., et al., "Pyrylocyanines. Unsymmetrical ?-pyrylo- and?-pyridocyanines", "Chemistry of Heterocyclic Compounds", Jan. 1, 1985, pp. 34-38, vol. 21, No. 1, Published in: NY, USA.
Haucke, G., et al., "Absorption and Fluorescence of Pyrylium Salts", "Ber. Bunsenges. Phys. Chem", Jul. 1, 1992, pp. 880-886, vol. 96, No. 7, Publisher: Verlagsgesellschaft, Published in: https://doi.org/10.1002/bbpc.19920960706.
ISA/EP, "Search Report for corresponding application PE959184EP dated Jun. 7, 2019", pp. 1-10, Published in: Munich, DE.
Reynolds, G., et al., "The Preparation and Certain Reactions of 3-Formyl-4H-flavene", "Journal of Organic Chemistry", Feb. 1, 1971, pp. 600-602, vol. 36, No. 4, Published in: https://doi.org/10.1021/jo00803a026.
Reynolds, G., et al., "Solvent Shifts of Certain Aminoarylpyrylium Salts", "Journal of Heterocyclic Chemistry", Apr. 1, 1975, pp. 367-368, vol. 12, No. 2, Published in: https://doi.org/10.1002/jhet.5570120231.

\* cited by examiner

FIG. 1A
FIG. 1B
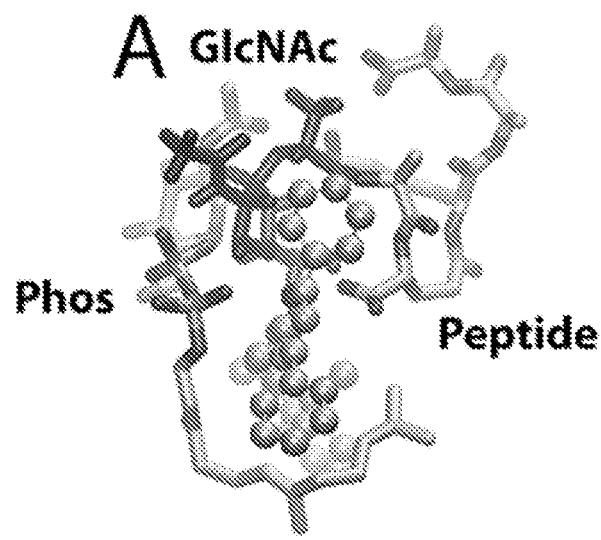
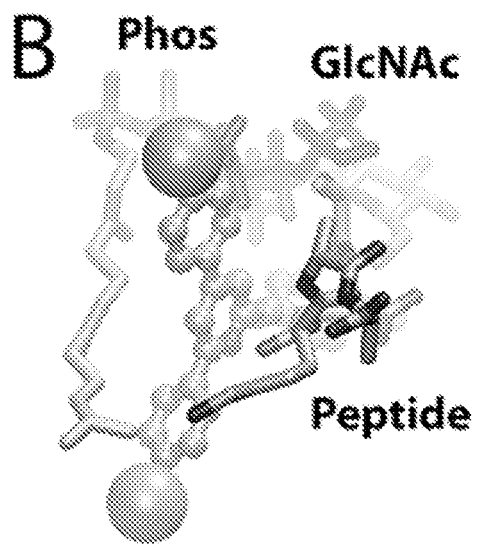
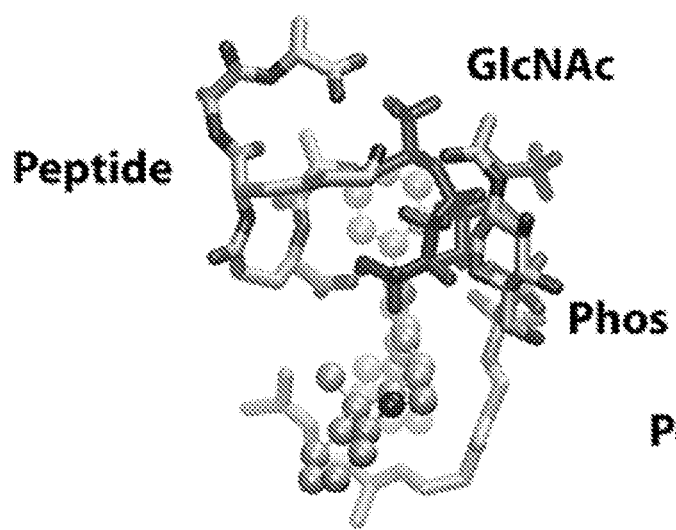
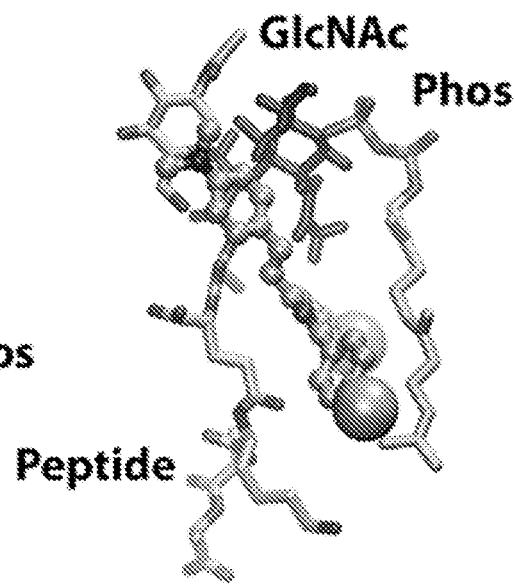

Scheme 1: A. Synthesis of lead compound 6jc48-1(BF$_4^-$ salt) and pyridinium analogs 4.
B.-C. Procedures to introduce chemical diversity into pyridinium and hindered pyrilium analogs.

FIG. 10A

| | 6jc37 | 6jc38 | 6jc39 | 6jc41-1 | 6jc43-1 | 6jc43-2 | 6jc48-1 | 6jc48-2 | Jc-49-1 | 6jc51-1 | BAS-00127538 |
|---|---|---|---|---|---|---|---|---|---|---|---|
| S. aureus MRSA 1094 | 16 | 64 | 2 | 16 | 4 | >=64 | 32 | >=64 | 8 | 1 | 0.5 |
| S. aureus HFH-30123 (MRSA) | 16 | >=64 | 4 | 32 | 4 | >=64 | 32 | >=64 | 8 | 2 | 0.5 |
| E. faecium EF1509 (VRE) | 64 | >=64 | 4 | 22.62742 | 4 | 64 | 2.828427 | 4 | 16 | 0.5 | 2 |
| E. faecium F118 (VRE) | 64 | >=64 | 4 | 8 | 4 | >=64 | 5.656854 | 16 | 16 | 2 | 2 |
| K. pneumoniae NR-15410 (KPC) | >=64 | >=64 | 64 | >=64 | >=64 | >=64 | >=64 | >=64 | >=64 | 16 | 8 |
| K. pneumoniae NR-15411 (KPC) | >=64 | >=64 | >=64 | >=64 | >=64 | >=64 | >=64 | >=64 | >=64 | 64 | 16 |
| A. baumanii ATCC 19606 | >=64 | >=64 | 16 | >=64 | 45.25483 | >=64 | >=64 | >=64 | >=64 | 8 | 4 |
| P. aeruginosa PA01 | >=64 | >=64 | >=64 | >=64 | >=64 | >=64 | >=64 | >=64 | >=64 | 64 | 64 |
| P. aeruginosa X13273 | >=64 | >=64 | >=64 | >=64 | >=64 | >=64 | >=64 | >=64 | >=64 | 45.25483 | >=64 |
| P. aeruginosa ATCC 27853 | >=64 | >=64 | >=64 | >=64 | >=64 | >=64 | >=64 | >=64 | >=64 | 64 | 64 |
| E. cloacae ATCC 13047 | >=64 | >=64 | >=64 | >=64 | >=64 | >=64 | >=64 | >=64 | >=64 | 64 | 32 |
| E. aerogenes ATCC 13048 | >=64 | >=64 | >=64 | >=64 | >=64 | >=64 | >=64 | >=64 | >=64 | 64 | 16 |
| $CC_{50\%}$ (72 h HeLa cells) | 18.96 | >32 | 1.31 | >32 | 0.93 | >32 | >100 | 60.51 | 2.2 | <.78125 | 0.56 |
| $CC_{50\%/MIC}$ (based on S. aureus) | 1.185 | NA | 0.655 | >2 | 0.2325 | NA | 3.125 | <0.945 | 0.275 | <.78125 | 1.12 |
| Lipid II binding Kd, $\mu M$ | No | No | 39±4 | 34±4 | 62±6 | ND | 0.15±0.03 | 1.14±0.3 | 0.17±0.05 | 9.2±2 | 1.81±0.3 |

FIG. 10B

| | 6jc51-2 | 6jc-53-2 | 6jc-58 | 6jc-59-1 | 6jc-59-3 | 6jc-60-1 | 6jc64-1 | 6jc64-2 | 6jc64-3 | 6jc65-1 | BAS-00127538 |
|---|---|---|---|---|---|---|---|---|---|---|---|
| S. aureus MRSA 1094 | 2 | 2 | 1.414214 | 2 | 4 | 8 | 4 | 8 | 5.66 | 2.83 | 0.5 |
| S. aureus HFH-30123 (MRSA) | 4 | 4 | 2 | 2 | 4 | 8 | 4 | 8 | 4 | 2 | 0.5 |
| E. faecium EF1509 (VRE) | 0.5 | 8 | 4 | 4 | 5.656854 | 8 | 4 | 5.66 | 8 | 2 | 2 |
| E. faecium F118 (VRE) | 2 | 5.656854249 | 4 | 4 | 8 | 8 | 5.66 | 16 | 8 | 4 | 2 |
| K. pneumoniae NR-15410 (KPC) | 64 | >=64 | 45.25483 | >=64 | >=64 | >=64 | >=64 | >=64 | 64 | 64 | 8 |
| K. pneumoniae NR-15411 (KPC) | >=64 | >=64 | 64 | >=64 | >=64 | >=64 | >=64 | >=64 | 64 | >=64 | 16 |
| A. baumanii ATCC 19606 | 32 | >=64 | 8 | >=64 | >=64 | >=64 | 16 | >=64 | >=64 | 11.31 | 4 |
| P. aeruginosa PA01 | >=64 | >=64 | 64 | >=64 | >=64 | >=64 | >=64 | >=64 | >=64 | 64 | 64 |
| P. aeruginosa X13273 | >=64 | >=64 | 32 | >=64 | >=64 | >=64 | >=64 | >=64 | >=64 | 64 | >=64 |
| P. aeruginosa ATCC 27853 | >=64 | >=64 | 64 | >=64 | >=64 | >=64 | >=64 | >=64 | >=64 | 64 | >=64 |
| E. cloacae ATCC 13047 | >=64 | >=64 | 64 | >=64 | >=64 | >=64 | >=64 | >=64 | 64 | 64 | 32 |
| E. aerogenes ATCC 13048 | >=64 | >=64 | 32 | >=64 | >=64 | >=64 | >=64 | >=64 | >=64 | 32 | 16 |
| CC$_{50\%}$ (72 h HeLa cells) | <.78125 | 1.12 | <.78125 | <.78125 | 1.35 | <.78125 | <.78125 | <.78125 | 3.29 | <.78125 | 0.56 |
| CC$_{50\%\text{MIC}}$ (based on S. aureus) | <.39 | 0.56 | 0.56 | 0.39 | 0.3375 | 0.097 | 0.195 | 0.097 | 0.581 | 0.276 | 1.12 |
| Lipid II binding Kd, μM | 9.5±2 | 10±3 | 17±4 | 1.9±0.3 | 27.9±3 | 37.9±4 | 07.28±0.3 | 23.8±4 | 4.92±0.5 | 2.17±0.2 | 1.81±0.3 |

FIG. 10C

| | 6jc65-2 | 6jc66-1 | 6jc66-2 | 6jc66-3 | 6jc66-4 | 6jc-67A | 6jc-69-1 | 6jc-69-3 | 6jc-69-4 | 6jc-69-5 | BAS-00127538 |
|---|---|---|---|---|---|---|---|---|---|---|---|
| S. aureus MRSA 1094 | 2 | 2.83 | 4 | 8 | 2 | 1 | 2 | 4 | 8 | >=64 | 0.5 |
| S. aureus HFH-30123 (MRSA) | 2 | 4 | 4 | 8 | 2 | 1 | 2 | 4 | 8 | 64 | 0.5 |
| E. faecium EF1509 (VRE) | 2 | 4 | 4 | 4 | 2 | 2 | 2 | 2.83 | 4 | 6 | 2 |
| E. faecium F118 (VRE) | 4 | 8 | 5.66 | 11.31 | 4 | 1.41 | 2 | 4 | 5.66 | 11.31 | 2 |
| K. pneumoniae NR-15410 (KPC) | 64 | >=64 | 64 | >=64 | 64 | 16 | >=64 | >=64 | >=64 | >=64 | 8 |
| K. pneumoniae NR-15411 (KPC) | >=64 | >=64 | >=64 | >=64 | >=64 | 32 | >=64 | >=64 | >=64 | >=64 | 16 |
| A. baumanii ATCC 19606 | 32 | 45.25 | 64 | >=64 | 64 | 4 | 32 | >=64 | >=64 | >=64 | 4 |
| P. aeruginosa PA01 | >=64 | >=64 | >=64 | >=64 | >=64 | 64 | >=64 | >=64 | >=64 | >=64 | 64 |
| P. aeruginosa X13273 | >=64 | >=64 | >=64 | >=64 | >=64 | 32 | >=64 | >=64 | >=64 | >=64 | >=64 |
| P. aeruginosa ATCC 27853 | >=64 | >=64 | >=64 | >=64 | >=64 | 32 | >=64 | >=64 | >=64 | >=64 | >=64 |
| E. cloacae ATCC 13047 | 64 | >=64 | >=64 | >=64 | >=64 | 32 | >=64 | >=64 | >=64 | >=64 | 32 |
| E. aerogenes ATCC 13048 | 64 | >=64 | >=64 | >=64 | >=64 | 16 | >=64 | >=64 | >=64 | >=64 | 16 |
| $CC_{50\%}$ (72 h HeLa cells) | 0.94 | 1.36 | 1.42 | 5.68 | 0.92 | <.78125 | <.78125 | <.78125 | 3.09 | 4.43 | 0.56 |
| $CC_{50\%}/MIC$ (based on S. aureus) | 0.47 | 0.48 | 0.355 | 0.71 | 0.46 | 0.78 | 0.39 | 0.195 | 0.38 | 0.06 | 1.12 |
| Lipid II binding Kd, μM | 3.9±0.4 | 2.9±0.3 | 1.6±0.2 | 60±11 | 27.9±2 | 7.89±0.2 | 16.1±0.3 | 0.6±0.1 | 30.3±0.5 | 32.7±2 | 1.81±0.3 |

FIG. 10D

| | 6jc67 | 6jc67A | 6jc69-1 | 6jc69-3 | 6jc69-4 | 6jc69-5 | 6jc76-1 | 6jc76-2 | 6jc77-1 | 6jc77-2 | BAS-00127538 |
|---|---|---|---|---|---|---|---|---|---|---|---|
| S. aureus MRSA 1094 | 0.5 | 1 | 2 | 4 | 8 | >=64 | 2 | 4 | 1.41 | 2 | 0.5 |
| S. aureus HFH-30123 (MRSA) | 0.5 | 1 | 2 | 4 | 8 | 64 | 2 | 4 | 2 | 4 | 0.5 |
| E. faecium EF1509 (VRE) | 2 | 2 | 2 | 2.83 | 4 | 6 | 2 | 2.83 | 2 | 2 | 2 |
| E. faecium F118 (VRE) | 2 | 1.41 | 2 | 4 | 5.66 | 11.31 | 2 | 2 | 2 | 4 | 2 |
| K. pneumoniae NR-15410 (KPC) | 16 | 16 | >=64 | >=64 | >=64 | >=64 | 64 | >=64 | >=64 | >=64 | 16 |
| K. pneumoniae NR-15411 (KPC) | 16 | 32 | >=64 | >=64 | >=64 | >=64 | 64 | >=64 | >=64 | >=64 | 16 |
| A. baumanii ATCC 19606 | 4 | 4 | 32 | >=64 | >=64 | >=64 | 8 | >=64 | 8 | 64 | 4 |
| P. aeruginosa PA01 | >=64 | 64 | >=64 | >=64 | >=64 | >=64 | 45.25 | >=64 | >=64 | >=64 | >=64 |
| P. aeruginosa X13273 | >=64 | 32 | >=64 | >=64 | >=64 | >=64 | 32 | >=64 | >=64 | >=64 | >=64 |
| P. aeruginosa ATCC 27853 | >=64 | 32 | >=64 | >=64 | >=64 | >=64 | 22.63 | >=64 | >=64 | >=64 | >=64 |
| E. cloacae ATCC 13047 | 32 | 32 | >=64 | >=64 | >=64 | >=64 | 32 | >=64 | >=64 | >=64 | 32 |
| E. aerogenes ATCC 13048 | 16 | 16 | >=64 | >=64 | >=64 | >=64 | 45.25483 | >=64 | >=64 | >=64 | 16 |
| $CC_{50\%}$ (72 h HeLa cells) | <.78125 | <.78125 | <.78125 | <.78125 | 3.09 | 4.43 | <.78125 | <.78125 | <.78125 | 1.995 | 0.56 |
| $CC_{50\%MIC}$ (based on S. aureus) | 1.56 | 0.78 | 0.39 | 0.195 | 0.38 | 0.06 | 0.39 | 0.195 | 0.55 | 0.99 | 1.12 |

SMALL MOLECULE LIPID II INHIBITORS

CROSS REFERENCE TO RELATED APPLICATIONS

This application is a 371 national stage application of PCT Application No. PCT/US16/067774, filed Dec. 20, 2016, and claims the benefit of provisional application 62/270,184, entitled "Small Molecule Lipid II Inhibitors," filed Dec. 21, 2015, the entire contents of which are incorporated herein.

STATEMENT OF GOVERNMENT INTEREST

This invention was made with government support under Grant Number A1092033 awarded by the National Institutes of Health. The government has certain rights in the invention.

BACKGROUND

1. Field of the Invention

The present invention generally relates to the field of medicine, and specifically to Lipid II (LII) binding agents which are novel antibiotic drugs which can be used in pharmaceutical compositions to treat bacterial infections. The disclosures herein relate, inter alia, to these molecules, their preparation, and their use.

2. Background of the Invention

The public is at increasing risk to emerging infectious diseases and resistant strains of bacteria. The development of resistant bacterial pathogens is rendering current antibiotics largely ineffective, making it essential that new drugs be developed to fight infections caused by these agents. LII is an essential precursor in bacterial membrane biogenesis and an established, yet underused target for antibiotics currently in clinical use. This invention, inter alia, provides small molecule LII inhibitors, identified based on the interaction between defensins, a family of natural antimicrobial peptides, and LII. Characterization of a preferred LII inhibitor reveals that it specifically binds to II, targets bacterial cell wall synthesis, specifically acts against *Enterococci* and possesses in vivo efficacy in a murine model for sepsis. These findings indicate that small molecule LII inhibitors can serve as a novel class of antibiotic compounds to combat pathogenic infections caused by multi-drug resistant organisms.

The chemical pathway of bacterial cell wall biosynthesis is well studied and a validated target for the development of antibacterial agents. Cell wall biosynthesis involves two major processes: (1) the biosynthesis of cell wall teichoic acids and (2) the biosynthesis of peptidoglycan. Key molecules in these pathways, including enzymes and precursor molecules are attractive targets for the development of novel antibacterial agents.

LII is an amphipathic peptidoglycan named for the bactoprenol hydrocarbon chain which anchors it into the bacterial cell membrane. LII is essential for bacterial cell wall biosynthesis, but is also present in bacteria without a cell wall, and is believed to be a crucial structural molecule in bacteria. LII translocates across the cell membrane to deliver and incorporate a disaccharide-peptide building block to the peptidoglycan mesh.

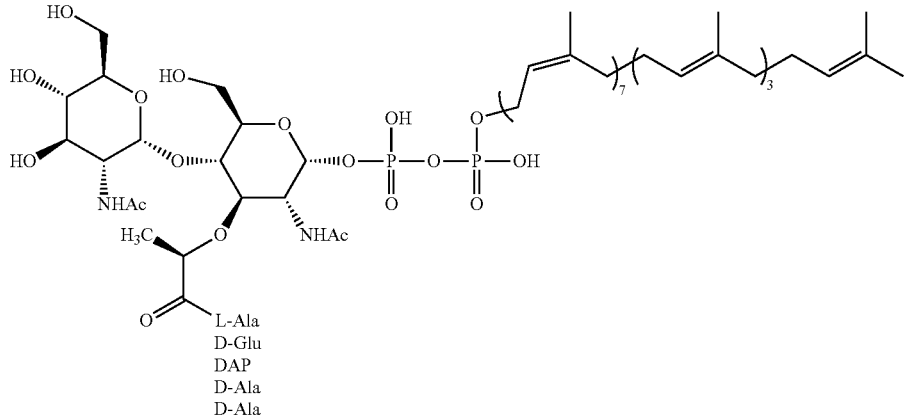

Lipid II (LII), $C_{94}H_{156}N_8O_{26}P_2$

The cell walls of both Gram-negative and Gram-positive bacteria comprise a peptidoglycan layer which is composed of a polymer of alternating amino sugars (N-acetylglucosamine (GlcNAc) and N-acetylmuramic acid (MurNAc)). On the cytoplasmic side of the plasma membrane, the soluble precursor UDP-MurNAc-pentapeptide is linked to the membrane carrier bactoprenol-phosphate ($C_{55}P$), yielding Lipid I (LI). In a second step, GlcNac is added by the enzyme MurG to yield LII. LII is essential for cell wall biosynthesis, is synthesized in limited amounts, and has a high turnover rate, making it an attractive target for antibacterial compounds.

Various classes of natural antibiotic peptides have been discovered that bind LII, including depsipeptides, lantibiotics, cyclic peptides and glycopeptides. Of these, vancomycin and its more recently developed derivatives daptomycin, oritavancin and telavancin, are approved as first line treatments for Gram-positive infections. However, resistance to these drugs is increasingly reported. Several studies on defensins, effector peptides of innate immunity, revealed specific interactions of defensins with LII, adding another class of natural compounds to the growing list of structurally unrelated peptides that bind this target. Based on the interaction between LII and human neutrophil peptide-1 (HNP1), this study produced, for the first time, low molecular weight synthetic compounds that target LII with high specificity and affinity. A lead compound, BAS00127538 (also sometimes referred to herein as 6jc67 or compound 6jc67), was characterized further and revealed a unique interaction with LII that differs from antibiotics currently in clinical use or development. In this study, the structural and functional relationships of derivatives of BAS00127538, and their uses, are reported.

SUMMARY OF THE INVENTION

The di-benzene-pyrylium-indolene inhibitor of Lipid II, termed BAS00127538 or 6jc67 (1-methyl-2,4-diphenyl-6-((1E,3E)-3-(1,3,3-trimethylindolin-2-ylidene)prop-1-en-1yl)pyryl-1-ium) tetrafluoroborate), is the first small molecule LII inhibitor and is structurally different from natural agents that bind LII, such as vancomycin.

BAS00127538

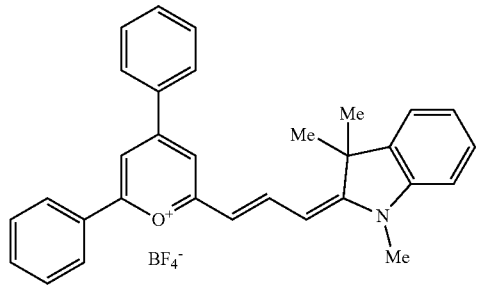

6jc67

Here, the synthesis and biological evaluation of new analogs of this compound is described. These compounds are designed to investigate the structure-activity relationships of the molecule scaffold. The results provided here indicate an activity map of the scaffold and identify regions of the molecule that affect cytotoxicity. LII binding, and the range of antibacterial action. The compound, 6jc48-1, showed particularly enhanced drug-like properties compared to BAS00127538.

6jc48-1

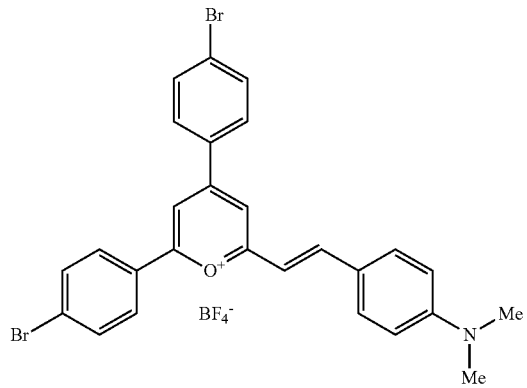

Compound 6jc48-1 ((E)-2,4-bis(4-bromophenyl)-6-(4-(dimethylamino)styryl)pyrylium boron tetrafluoride salt) has reduced cytotoxicity, but retains specific LII binding and activity against *Enterococcus* spp. in vitro and in vivo. In addition, Compound 6jc48-1 was stable in plasma and had a markedly improved pharmacokinetic profile, with a half-life of over 13 hours upon intravenous administration. These results suggest that scaffolds like that of Compound 6jc48-1 provide a basic structure for small molecule antibiotic drugs that target LII. See Compound 6jc48-1 Scaffold (Formula I) structure below. Active compounds include but are not limited to those compounds according to Formula I.

Formula I

Compound 6jc48-1 Scaffold

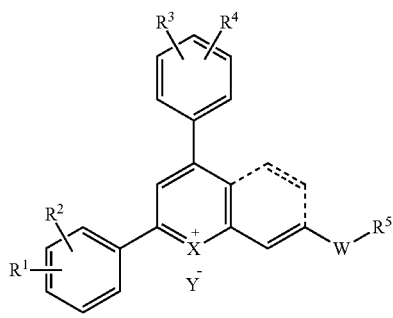

wherein each $R^1$, $R^2$, $R^3$ and $R^4$ independently is H; halogen; trihalomethyl; —$OR^6$; —$NHR^6$; —$NR^6R^6$; $C_1$-$C_6$ alkyl optionally substituted with amino or halo; $C_4$-$C_6$ tert-alkyl; $C_5$-$C_7$ cycloalkyl optionally substituted with amino or halo; $C_4$-$C_6$ cycloheteroalkyl optionally substituted with amino or halo; aryl optionally substituted with amino or halo; or heteroaryl optionally substituted with amino or halo, wherein each $R^6$ independently is H, $C_1$-$C_6$ alkyl, $C_5$-$C_7$ cycloalkyl, $C_4$-$C_6$ cycloheteroalkyl, aryl or heteroaryl and wherein halo is chloride, fluoride or bromide;
wherein W is a bond, —$CH_2$—, —CH—, —$CH_2$—CH—, —CH—$CH_2$—, —CH=CH—, —CH=CH—$CH_2$—, or —$CH_2$—CH=CH—;
wherein $R^5$ is a mono-, bi- or tri-cyclo group containing 4-18 carbon atoms and optionally containing one or more nitrogen heteroatoms, which optionally is substituted with an amino group, a methyl group, an ethyl group, or a halogen, wherein halo is chloride, fluoride or bromide;
wherein X is O, S or $NR^7$, wherein $R^7$ is H, methyl, or ethyl; wherein Y is an anion; and
wherein the dotted lines indicate an optional ethenyl group.
Generally preferred compounds are those wherein
$R_1$ is H, methyl, ethyl, t-butyl, bromo, fluoro, or chloro;
$R_2$ is H, methyl, ethyl, t-butyl, bromo, fluoro, or chloro;
W is a bond, methyl, or ethenyl;
$R_3$ is a substituted or unsubstituted mono-, bi- or tri-cyclo group containing 4-14 carbon atoms and optionally containing one or more nitrogen heteroatoms, such as a phenyl, indolino, quinolino or pyridoquinolino group, wherein the optional substitution is an amino, methyl, ethyl, methylamino, dimethylamino, halogen or trihalomethyl group;
X is oxygen; and
Y is $BF_4^-$.
The disclosures herein describe an invention that includes small molecule compounds, methods of synthesis and intermediate compounds, and methods for their use in killing bacteria and treating bacterial infection.

The invention therefore relates to compounds according to:

Formula I

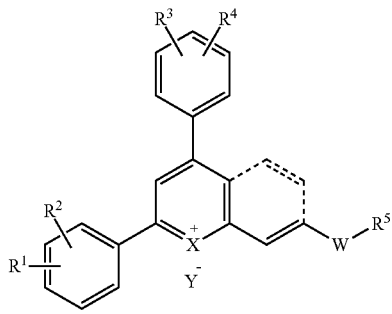

wherein each $R^1$, $R^2$, $R^3$ and $R^4$ independently is H; halogen; trihalomethyl; —$OR^6$; —$NHR^6$; —$NR^6R^6$; $C_1$-$C_6$ alkyl optionally substituted with amino or halo; $C_4$-$C_6$ tert-alkyl; $C_5$-$C_7$ cycloalkyl optionally substituted with amino or halo; $C_4$-$C_6$ cycloheteroalkyl optionally substituted with amino or halo; aryl optionally substituted with amino or halo; or heteroaryl optionally substituted with amino or halo, wherein each $R^6$ independently is H, $C_1$-$C_6$ alkyl, $C_{5-7}$cycloalkyl, $C_4$-$C_6$ cycloheteroalkyl, aryl or heteroaryl and wherein halo is chloride, fluoride or bromide;
wherein W is a bond, —$CH_2$—, —CH—, —$CH_2$—CH—, —CH=CH—, —CH=CH—$CH_2$—, or —$CH_2$—CH=CH—;
wherein $R^5$ is a mono-, bi- or tri-cyclo group containing 4-18 carbon atoms and optionally containing one or more nitrogen heteroatoms, which optionally is substituted with an amino group, a methyl group, an ethyl group, or a halogen, wherein halo is chloride, fluoride or bromide;
wherein X is O, S or $NR^7$, wherein $R^7$ is H, methyl, or ethyl;
wherein Y is an anion; and
wherein the dotted lines indicate an optional ethenyl group.

Compounds wherein each $R^1$, $R^2$, $R^3$ and $R^4$ independently are in the meta or para position are preferred, as are compounds wherein each $R^1$, $R^2$, $R^3$ and $R^4$ independently are selected from the group consisting of H, bromine, methyl, ethyl, and tert-alkyl. In addition, compounds wherein $R^5$ is p-dimethylaminophenyl optionally substituted with halogen, trihalomethyl, —$OR^4$, —$NHR^4$, —$NR^4R^4$, $C_1$-$C_6$ alkyl, $C_5$-$C_7$ cycloalkyl, $C_4$-$C_6$ cycloheteroalkyl, aryl, heteroaryl; 1H-indol-3-yl; 1-methyl-1H-indol-3-yl; or 1,2,3,5,6,7-hexahydropyrido(3,2,1-ij)quinolin-9-yl, and 1,3,3-trimethylindolin-2-ylidene also are preferred.

Compounds wherein halo is bromide or wherein W is selected from the group consisting of a bond, —CH=CH— and —CH=CH—CH=, or wherein Y is $BF_4^-$ also are preferred. Specific compounds according to the invention include those selected from the group consisting of compounds 6jc39, 6jc43-1, 6jc48-1, 6jc48-2, 6jc51-1, 6jc51-2, 6jc53-2, 6jc58, 6jc59-1, 6jc59-2, 6jc59-3, 6jc64-1, 6jc64-2, 6jc64-3, 6jc65-1, 6jc65-2, 6jc66-1, 6jc66-2, 6jc66-3, 6jc66-4, 6jc67, 6jc69-1, 6jc69-3, 6jc69-4, 6jc76-1, 6jc76-2, 6jc77-1, 6jc77-2, 7jc46-1, 7jc47-1, and 7jc47-2. More preferred compounds include those selected from the group consisting of compounds 6jc48-1, 6jc58, 6jc66-3, 6jc66-4, 6jc67, 6jc77-1, 6jc77-2, 7jc46-1, 7jc47-1, and 7jc47-2. Most preferred compounds include those selected from the group consisting of compounds 6jc48-1, 6jc67, 7jc46-1, 7jc47-1, and 7jc47-2; and most particularly compound 6jc48-1.

The invention also relates to pharmaceutical compositions comprising a pharmaceutically acceptable vehicle and a compound of Formula I, above, including compounds 6jc39, 6jc43-1, 6jc48-1, 6jc48-2, 6jc51-1, 6jc51-2, 6jc53-2, 6jc58, 6jc59-1, 6jc59-2, 6jc59-3, 6jc64-1, 6jc64-2, 6jc64-3, 6jc65-1, 6jc65-2, 6jc66-1, 6jc66-2, 6jc66-3, 6jc66-4, 6jc67, 6jc69-1, 6jc69-3, 6jc69-4, 6jc76-1, 6jc76-2, 6jc77-1, 6jc77-2, 7jc46-1, 7jc47-1, and 7jc47-2. More preferred compounds for use in a pharmaceutical composition include those selected from the group consisting of compounds 6jc48-1, 6jc58, 6jc66-3, 6jc66-4, 6jc67, 6jc77-1, 6jc77-2, 7jc46-1, 7jc47-1, and 7jc47-2. Most preferred compounds for use in a pharmaceutical composition include those selected from the group consisting of compounds 6jc48-1, 6jc67, 7jc46-1, 7jc47-1, and 7jc47-2; and most particularly compound 6jc48-1.

The invention also involves a method of treating a subject in need for bacterial infection, comprising administering to the subject a compound of Formula I. In preferred embodiments, the subject suffers from infection with *Enterococcus* spp., such as *E. faecalis* and *E. faecium*. In preferred embodiments, the subject suffers from infection with a bacterium selected from the group consisting of *E. faecalis, E. faecium. Staphylococcus aureus, Bacillus anthracia*, and *Acinetobacter baumanii*. In additional preferred embodiments, the bacterial infection is an infection with an antibiotic-resistant bacterial strain.

In further embodiments, the invention comprises a method of synthesizing a compound according to Formula I:

Formula I

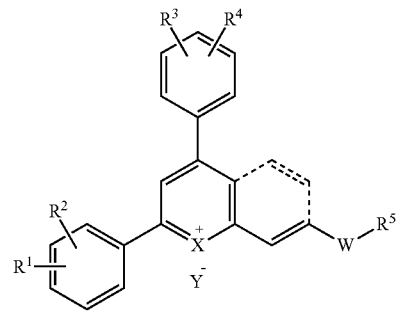

wherein each $R^1$, $R^2$, $R^3$ and $R^4$ independently is H; halogen; trihalomethyl; —$OR^6$; —$NHR^6$; —$NR^6R^6$; $C_1$-$C_6$ alkyl optionally substituted with amino or halo; $C_4$-$C_6$ tert-alkyl; $C_5$-$C_7$ cycloalkyl optionally substituted with amino or halo; $C_4$-$C_6$ cycloheteroalkyl optionally substituted with amino or halo; aryl optionally substituted with amino or halo; or heteroaryl optionally substituted with amino or halo, wherein each $R^6$ independently is H, $C_1$-$C_6$ alkyl, $C_5$-$C_7$ cycloalkyl, $C_4$-$C_6$ cycloheteroalkyl, aryl or heteroaryl and wherein halo is chloride, fluoride or bromide;
wherein W is a bond, —$CH_2$—, —CH—, —$CH_2$—CH—, —$CH$—$CH_2$—, —CH=CH—, —CH=CH—$CH_2$—, or —$CH_2$—CH=CH—;
wherein $R^5$ is a mono-, bi- or tri-cyclo group containing 4-18 carbon atoms and optionally containing one or more nitrogen heteroatoms, which optionally is substituted with an amino group, a methyl group, an ethyl group, or a halogen, wherein halo is chloride, fluoride or bromide;

wherein X is O, S or NR$^7$, wherein R$^7$ is H, methyl, or ethyl;

wherein Y is an anion; and wherein the dotted lines indicate an optional ethenyl group;

comprising the steps:

(1) condensing a compound of Formula A, a compound of Formula B and a compound of Formula C, with an acidic reagent to obtain compound of Formula D

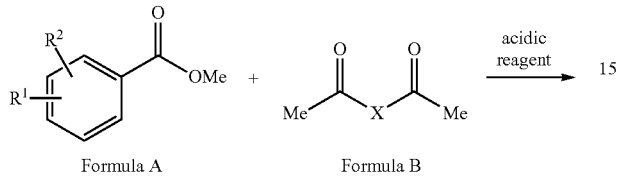

Formula A    Formula B

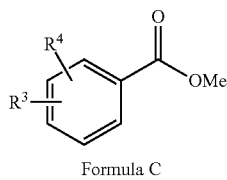

Formula C

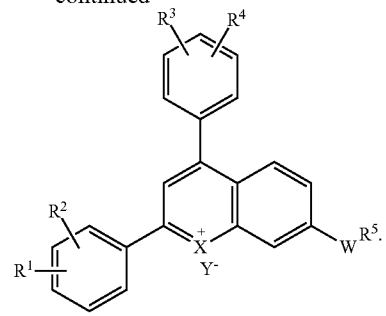

Formula D (2) optionally condensing Formula D with W-R$^5$ to obtain compound of Formula I Formula D Formula I In preferred embodiments, the acidic reagent is boron trifluoride etherate and/or W is selected from the group comprising: —CH$_2$—, —CH=CH—, —CH=CH—CH—, and —CH=CH—CH=. Yet further embodiments of the invention include a method of killing or reducing bacteria comprising contacting the bacteria with a compound of Formula I, and a method of killing or reducing bacteria on an object comprising contacting the object with a compound of Formula I and a method of protecting an object from colonization by bacteria comprising contacting the object with a compound of Formula I.

BRIEF DESCRIPTION OF THE DRAWINGS

The following drawings form part of the present specification and are included to further demonstrate certain embodiments of the present invention. The invention may be better understood by reference to one or more of these drawings in combination with the detailed description of specific embodiments presented herein.

FIG. 1A and FIG. 1B are models of BAS00127538 (FIG. 1A) and compound 6jc48-1 (FIG. 1B), in complex with a LII analog. The compounds are shown in standard CPK atom format, with the Br atoms for compound 6jc48-1 shown as vdW spheres. The LII is in licorice representation. The phosphate (Phos), sugars (GlcNAc) and pentapeptide (Peptide) are indicated. The upper and lower panels of each of FIG. 1A and FIG. 1B are approximately 180° rotations of the complexes. FIG. 1C provides the chemical structure of de novo synthesized BAS00127538 and the 6jc48-1 derivative.

FIG. 10A, FIG. 10B, FIG. 10C and FIG. 10D are a table showing the antibacterial activity of the indicated compounds.

FIG. 11A) and 6jc67 (BAS00127538) (MIC 2 µg/ml; FIG. 11B) on the macromolecular synthetic pathways for DNA, cell wall, protein, and lipid.

DETAILED DESCRIPTION

Figure 2:
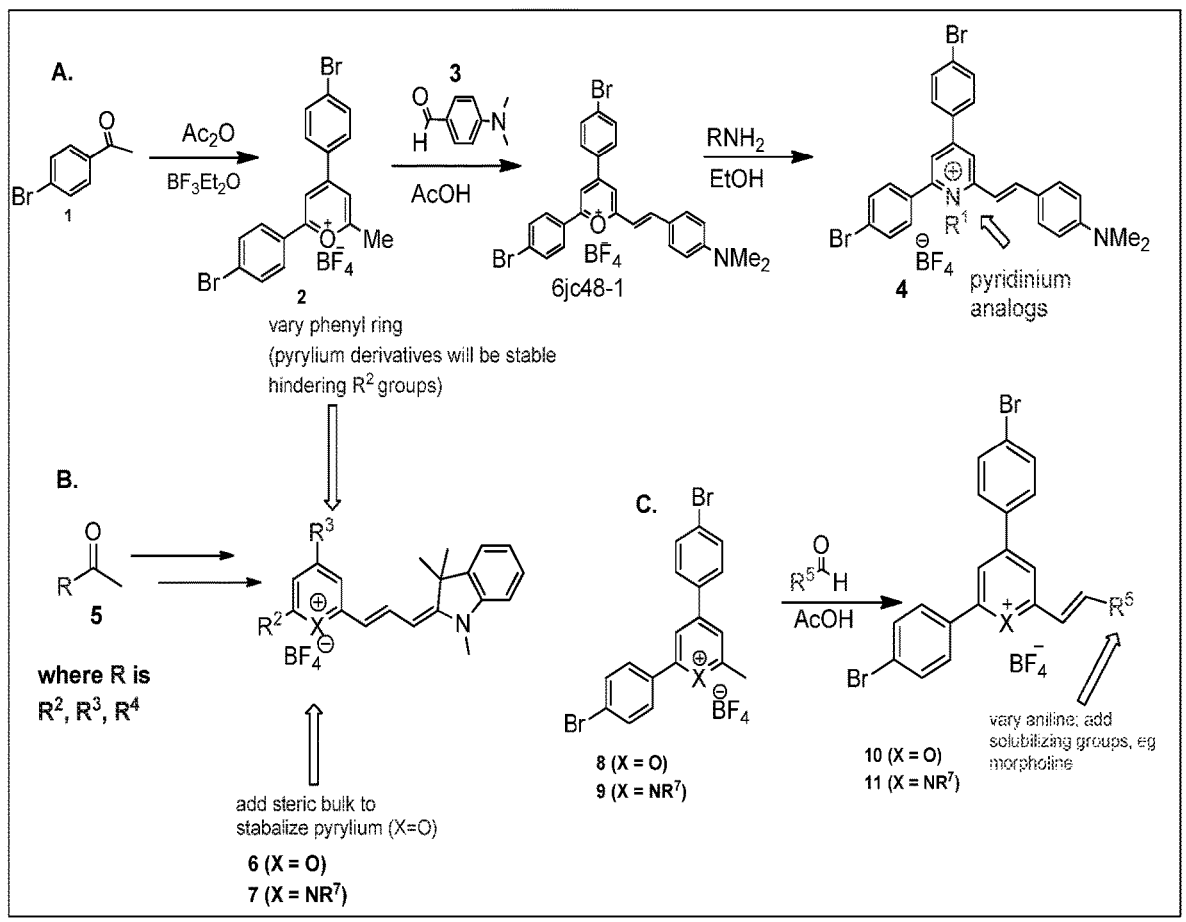
FIG. 2 shows a chemical synthetic scheme for the synthesis of BAS00127538.

In the following description, for the purposes of explanation, numerous specific details are set forth in order to provide a thorough understanding of the present invention. It will be apparent, however, to one skilled in the art that the present invention may be practiced without these specific details. In order that the invention may be readily understood and put into practical effect, particular preferred embodiments will now be described by way of the following non-limiting examples.

1. DEFINITIONS

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Generally, nomenclature used in connection with, and techniques of, chemistry and chemical synthesis described herein are those well-known and commonly used in the art. The methods and techniques of the present invention are performed generally according to conventional methods well known in the art and as described in various general and more specific references that are cited and discussed throughout the present specification unless otherwise indicated. Unless defined otherwise, all technical and scientific terms used herein have the same meaning as commonly understood by one of ordinary skill in the art.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and intended to be non-limiting. Furthermore, where the description of one or more embodiments uses the term "comprising," those skilled in the art would understand that, in some specific instances, the embodiment or embodiments can be alternatively described using the language "consisting essentially of" and/or "consisting of."

The term "scaffold" refers to the core region of a compound, or a generic chemical structure based on the compound, which contains the portion of the structure that imparts some or all of the appropriate binding and/or activity to the compound. Additional or modified moieties can be placed on the structure to optimize such binding and activity.

The term "subject" or "subject in need" as used herein refers to animals, such as mammals, or to organs an tissues of an animal, such as for transplant. Animals contemplated as subjects include humans, companion and service animals, farm animals, zoo animals, and the like, including humans; primates; dogs; cats; sheep; cattle; goats; pigs; horses; poultry such as chickens, turkeys, ducks, geese, and the like; mice; rats; rabbits; guinea pigs; and the like. The terms "subject," "patient," and "host" are used interchangeably. Preferably, the subject suffers from or is susceptible to a condition caused by or involving infection by bacteria. Most preferably, the subject suffers from or is subject to a condition that does lead or could lead to bacteremia of the blood (sepsis), of the urinary tract, of the intra-abdominal and pelvic region, of the heart valve (endocarditis), of the lungs, of the central nervous system, or lead to complicated or acute soft skin and tissue infections (SSTIs) and the like. Treatment of infections associated with medical devices and equipment such as ventilator-associated pneumonia (VAP) or central-line associated blood stream infections (CLABSIs) and the like obtained in a hospital or community setting are included. These infections generally are caused by bacteria, such as Gram-positive or Gram-negative bacteria, including, but not limited to any species of *Actinobacteria, Firmicutes, Tenericutes, Aquificae, Bacteriodetes, Deinococcus, Fusobacteria, gemmatemonadetes, Nitrospirae, Planctomycetes, Verrucomicrobia, Proteobacteria, Spirochaetes*, and *Synergistetes*. Preferred bacteria are Gram-positive. Most preferred are *Enterococci* spp., *Staphylococci* spp., or *Streptococci* spp.

The compounds and methods of the invention also can be used to reduce or kill bacteria in excised tissues of the animal body, such as organs and tissues for transplant, and can be used on objects that can be subject to undesirable colonization by bacteria, or used to protect food and food service items from colonization and/or infection by bacteria. Therefore, the term subject can loosely refer to the whole organism or to parts thereof.

The term "pharmaceutically acceptable" in respect of salts, ingredients or carriers and the like in pharmaceutical products, and in compounds used in or on the living body or tissues/organs of the body, refers to any convenient compound or group of compounds that are not toxic and that do not destroy or significantly diminish the pharmacological or antibacterial activity of the agent with which it is formulated. Such pharmaceutically acceptable carriers or vehicles encompass any of the standard pharmaceutically accepted solid, liquid, or gaseous carriers known in the art, such as those discussed in the art.

2. OVERVIEW

This invention involves identifying and optimizing small molecule antagonists of LII. A lead compound, BAS00127538, was structurally optimized to reduce cytotoxicity, increase in vivo stability and retain activity against *Enterococci* bacterial pathogens. In the United States, *Enterococci* infections in hospital settings are the second most common and vancomycin resistance is on the rise. The compound 6jc48-1, a preferred compound, retained activity against *Enterococci* spp. specifically, a result that is somewhat surprising. The parent scaffold of BAS00127538 is potent against *S. aureus* and *Enterococci*, yet it displays broad-range antibacterial activity, including activity against Gram-negative species. Without wishing to be bound by theory, one possible explanation could be variations of LII composition between different bacterial species, which would cause differences in binding and/or activity. For example, amidation of the D-iso-glutamine residue of LII has been described in strains of *S. aureus*, resulting in reduced sensitivity to the glycopeptide antibiotics such as vancomycin. This modification has not been found in vancomycin-resistant *Enterococci* spp.

Additional variations, such as differences in amino acid linkage between peptidoglycan subunits or variations in the MurNac/GlnNac moieties of LII could further potentiate binding of the benzoaldehyde moiety of 6jc48-1, but not the indolene moiety in the BAS00127538 scaffold. This is consistent with the model of the 6jc48-1 interactions shown in FIG. 1. The second major difference between parent BAS00127538 structure and compound 6jc48-1 is reduced cellular cytotoxicity. Mechanism-of-action studies revealed that compound 6jc48-1 does not inhibit protein synthesis to the same extent as BAS00127538. Since the incorporation of bromines in the para positions of the phenyl rings of the parent scaffold did not reduce cytotoxicity (compound 6jc67A), the indolene moiety in BAS00127538 likely contributes to cytotoxicity. The model revealed similar interactions of the parent scaffold and compound 6jc48-1 with LII, possibly suggesting that the indolene moiety in the parent BAS00127538 molecule contributes to the interference of protein synthesis as a cause for cytotoxicity. Studies showed that in the interaction of BAS00127538 with LII, the pyrylium interacts with phosphate; the indolene interacts with isoprenyl; and the diphenyl interacts with muramic acid.

The present in vitro and in vivo data indicate that the oxonium moiety in compound 6jc48-1 is chemically stable. In a previous study, replacement of the positively charged oxygen with nitrogen increased antibacterial activity and LII binding, but did not lead to an improvement of cytotoxicity in the BAS00127538 scaffold. Introducing this change in the compound 6jc48-1 scaffold could further enhance its antibacterial spectrum while maintaining low cytotoxicity.

3. EMBODIMENTS

A. Ligand Design Strategy

A molecular model of the interaction of BAS00127538 with a LII analog was obtained, consistent the NMR data obtained. See Varney et al., *Turning defense into offense: defensin mimetics as novel antibiotics targeting lipid II.* PLoS Pathog. 9(11):e1003732, 2013. The model is shown in FIG. 1A with LII. In the model, the two phenyl rings and the pyrylium wrap around LII with the positive charge of the pyrylium being in the vicinity of the Lipid II phosphates, one phenyl ring interacting with the sugar moiety and the second interacting with the top of the aliphatic tail. In addition, the indolene moiety also interacts with the aliphatic tail. Based on this interaction motif it can be hypothesized that the increased hydrophobicity of the phenyl groups would lead to more favorable interactions with the sugar moiety and aliphatic tail of lipid II. Similarly, the presence and nature of the indolene was varied as well as the pyrylium to ring linker length and composition to understand their impact the SAR. Throughout, the positively charged pyrylium was maintained given that previous results had shown that pyridinium was not active.

This led to the design, synthesis and experimental validation of the compounds shown in Table 5. Subsequent modeling of the preferred synthesized compound (6jc48-1) showed the binding orientation to be similar to that of BAS00127538 (see FIGS. 1B and 1C), though some variation in the LII conformation upon binding of compounds within the complex does occur. These include additional interactions of the bromophenyl moieties with the sugar and aliphatic moieties. In addition, the dimethylaniline analog in compound 6jc48-1 interacts with the peptidic portion of LII and the ligand is shifted further away from the phosphate moieties. In contrast, the indolene moiety of BAS00127538 seemingly interacts with the aliphatic chain of the C55 only.

B. Chemical Compounds

The compounds of the invention include, but are not limited to, any compounds containing the basic structure according to Formula I. In general, structures according to this general formula that have increased polar surface area are preferred. In addition, structures with a lower C log P (as a measure of hydrophilicity, or solubility) also are preferred.

C. Pharmaceutical and Other Products

The compounds discussed herein can be present in the form of pharmaceutically acceptable salts, acids, hydrates, and solvates, or as a base. These compounds can exist in amorphous form or in any crystalline form. Preferably, the pharmaceutical compositions comprise a therapeutically effective amount. Any pharmaceutically acceptable salt can be used, as may be convenient. Generally, these salts are derived from pharmaceutically and biologically acceptable inorganic or organic acids and bases or metals. Examples of such pharmaceutically acceptable salts include, but are not limited to: acetate, adipate, alginate, ammonium, aspartate, benzoate, besylate, bicarbonate, bisulfate, butyrate, citrate, camphorate, camphorsulfonate, carbonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, magnesium, maleate, malonate, mesylate, 2-naphthalenesulfonate, nicotinate, nitrate, oxalate, palmoate, pectinate, persulfate, 3-phenylpropionate, phosphate, picrate, pivalate, potassium, propionate, salicylate, sodium, succinate, sulfate, tartrate, thiocyanate, toluenesulfonate (tosylate) and undecanoate salts. The compounds described here are drawn, where appropriate, as boron tetrafluoride salts, which is a preferred salt.

The therapeutic agents of some embodiments are also meant to include any or all stereochemical forms of the therapeutic agents where they exist (i.e., the R and/or S configurations for each asymmetric center). Therefore, single enantiomers, racemic mixtures, and diastereomers of the therapeutic agents are within the scope of the invention. Also within the scope of the invention are steric isomers and positional isomers of the therapeutic agents. The therapeutic agents of some embodiments are also meant to include compounds which differ only in the presence of one or more isotopically enriched atoms. For example, therapeutic agents in which one or more atom is replaced by, for example, deuterium, tritium, $^{13}C$, $^{14}C$ (or any isotopic labels as commonly used in the art such as phosphorus, calcium, iodine, chlorine, bromine, or any other convenient element for isotopic labeling) are within the scope of this invention.

In a preferred embodiment, the therapeutic agents of some embodiments are administered as a pharmaceutical composition that includes a pharmaceutically acceptable carrier or vehicle. The terms "pharmaceutically acceptable carrier" or pharmaceutically acceptable vehicle" refer to any convenient compound or group of compounds that is not toxic and that does not destroy or significantly diminish the pharmacological activity of the therapeutic agent with which it is formulated. Such pharmaceutically acceptable carriers or vehicles encompass any of the standard pharmaceutically accepted solid, liquid, or gaseous carriers known in the art, such as those discussed in the art.

Suitable carriers depend on the route of administration contemplated for the pharmaceutical composition, and are well-known in the art. The forms which the pharmaceutical composition can take include, but are not limited to: tablets, capsules, caplets, lozenges, dragees, pills, oral solutions, powders for dilution, powders for inhalation, vapors, gases, granules, sterile solutions for injection, transdermal patches, buccal patches, inserts and implants, rectal suppositories, vaginal suppositories, creams, lotions, ointments, topical coverings (e.g., wound coverings and bandages, and the like).

The carriers can be liquid, semi-liquid, gaseous, semi-solid, or solid, and serve to contain and deliver the active agent to the subject in a convenient form. Liquid or semi-liquid carriers can be in the form of a solution, suspension, emulsion, oil, gel, and the like, and include, for example aqueous solution (e.g., saline solutions, phosphate-buffered saline solutions, Ringer's, and the like), oil-in-water or water-in-oil suspensions, creams, lotions, ointments, and the like. Gaseous carriers can include, for example air, oxygen, fluorocarbons, dispersing agents, and the like. Solid carriers can include, for example, starch (e.g., corn starch, potato starch, rice starch, and the like), cellulose (e.g., microcrystalline cellulose, methylcellulose, and the like), sugars (e.g., lactose, sucrose, glucose, and the like), clays, minerals (e.g., talc, and the like), gums, and the like.

Extended and sustained release compositions also are contemplated for use with and in the inventive embodiments. Thus, suitable carriers can include any of the known ingredients to achieve a delayed release, extended release or sustained release of the active components. These methods are well known in the art.

A non-inclusive list of types of carriers and vehicles contemplated for use with the invention follows: fillers, diluents, adjuvants, pH adjusters, containers (e.g., ampoules, bottles, pre-filled syringes, and the like), flavorings, preservatives, colorings, taste-masking agents, sweeteners, oils, solvents, solvents, solubility enhancers, saline solutions, emulsifiers, suspending agents, wetting agents, dispersants, binders, releasing agents, lubricants, and the like. The person of skill is able to select from the known compounds used in pharmaceutical formulation to achieve the desired qualities and to produce an attractive and useful product.

The compounds discussed here also can be formulated into a liquid, solid or gaseous formulation for application to the surface of objects or impregnated into objects for the purpose of curtailing bacterial growth and the potential for infection. Such formulations can be used to coat medical instruments for use in surgery (e.g., metal or plastic instruments or containers therefor, surgical drapes, sutures, surgical gloves, catheters, trocars, wound dressings and bandages, sponges, and the like, or any object for which protection from or reduction of biofilm or bacterial growth is desirable in a medical or veterinarian medical setting. The compounds can be applied to objects e.g., by coating spraying, soaking or dipping, or any convenient method prior to or during use.

In addition, the compounds are useful in the food industry. The compounds of the invention can be applied to (e.g., by coating spraying, soaking or dipping) an object such as food or food containers, food processing equipment or tools and instruments used in food preparation. Hence the invention also included methods of preventing or reducing bacterial growth on objects by contacting the object with the compounds of the invention or a composition containing the compounds.

Therefore, in general, the compounds of the invention can be used to kill or reduce bacteria on an object by contacting the object with the compound. Such contacting can include soaking, dipping, spraying, and the like with a solution or dispersion/suspension of the compound, or by forming a coating on the object by application of a solution, dispersion, suspension, gel, powder or any convenient form containing the compounds of the invention. The coating can be temporary, semi-permanent, or permanent. Porous materials can be soaked or sprayed with the compounds to impregnate the material.

D. Administration

The products of the invention are contemplated to be administered to a subject in need by any convenient route of administration available to the physician or other person of skill. This can be any route which the practitioner deems to be most effective or convenient using considerations such as the patient, the patient's general condition, and the specific condition to be treated. For example, routes of administration can include, but are not limited to: oral, intravenous injection or infusion, subcutaneous injection, intraarterial injection, intrathecal injection, intraperitoneal injection, local injection into a site of infection, potential infection or injury, injection into a tumor, rectal, vaginal, topical, nasal, buccal, transdermal, sublingual, inhalation, transmucosal, wound covering, and the like. More than one route of administration can be used in one subject or in different subjects undergoing a treatment, for example, topical and intravenous, local injection and oral, and the like.

Appropriate dosages can be determined by the practitioner or any skilled person, based on the size of the subject, the disease condition, the severity of the infection, the bacteria responsible, and other factors. In general, for intravenous administration, intramuscular injection, nasal delivery, or oral delivery, the compounds can be administered every week, every day, twice per day, three times per day, four times per day, six times per day, or more often, at a dose range of about 100 mg to about 4000 mg, or about 200 mg to about 3000 mg, or about 400 mg to about 2000 mg, for example at a dose of about 100 mg, 200 mg, 400 mg, 500 mg, 750 mg, 1000 mg, 1500 mg, 2000 mg, 2500 mg, 3000 mg or 4000 mg. Preferably, a pharmaceutical product containing about 400 mg to about 2000 mg is given every 4-12 hours, or the product is administered at about 1 mg/kg to about 30 mg/kg every 4-12 hours. Therefore, a product designed to deliver or contain these amounts of compound contains a pharmaceutically effective amount of the inventive compound.

When the compound is formulated for topical use, in a gel, lotion, cream, ointment, and the like, a suitable pharmaceutical composition contains about 0.1% to about 10% of the compound in a suitable carrier. Preferred pharmaceutical compositions for topical use contain about 0.5% to about 5% of the compound, or about 1% to about 5% of the compound, including about 0.1%, about 0.5%, about 1%, about 2%, about 3%, about 5%, about 7.5%, or about 10% of the compound. These concentrations can be w/w or w/v. Therefore, a product designed to deliver or contain these amounts of compound contains a pharmaceutically effective amount of the inventive compound. For nasal delivery, the compound is contained in a suitable delivery vehicle for spray, at a concentration of about 25% to about 90% of the compound, or about 50% to about 90% of the compound, or about 60% to about 75% of the compound (w/v). Therefore, a product designed to deliver or contain these amounts of compound contains a pharmaceutically effective amount of the inventive compound.

For application to an object, the compounds can be dissolved or suspended in any convenient solution such as water, sterile water, saline, alcohol, oil, and the like which is convenient for preparing a soaking or dipping solution, a spray, which later optionally can be dried. The compounds can be formulated as a solid, for example a powder, or in a semi-solid, such as a gel, for application to any object. For example a food container or a catheter can be soaked in the composition prior to use, or a wound dressing can be impregnated with the composition. In addition, the compounds can be formulated in a hand wash or hand sanitizer, for example, in order to clean and sanitize skin or other objects. Alternatively, food itself, skin or other objects can be sprayed with the composition, or the composition mixed into the food to reduce bacteria. In such compositions, the compounds preferably comprise about 0.01% (w/w) to about 20% (w/w) of the carrier for soaking or spraying solutions, or food products. More preferably, about 1% (w/w) to about 10% (w/w) is used, or most preferably 2% (w/w) to about 10% (w/w).

The inventive compounds can be used alone, or in combination with other antibiotic or bactericidal compositions such as are known in the art. For example in treatment for an infection, the compound can be administered as a monotherapy, or in combination with another agent, either simultaneously or sequentially administered. The inventive compounds also can be used as part of an antibiotic cocktail. More than one of the inventive compounds can be used together as well, as a treatment for infection in a subject, or as an applied composition for treatment of an object, as well as in combination with other known antibiotics.

E. Treatment

The compounds and pharmaceutical compositions of the invention are contemplated for use in the treatment of disease conditions related to the presence of bacteria in a subject. Primarily, the conditions involve an infection, as discussed above, and the like. Treatment of infections with a Gram positive organism is preferred, but treatment of infections with a Gram-negative organism or multiple organisms is contemplated also. Resistant strains of bacteria also are contemplated to be treated with the compounds and compositions of the invention. Preferably, the bacteria are *Enterococcus* spp., including *E. faecalis*, *E. faecium*, *S. aureus* (SA), including vancomycin-resistant *S. aureus* (VRSA), vancomycin intermediate resistant *S. aureus* (VISA) and methicillin resistant *S. aureus* (MRSA) strains, *Bacillus* anthracia, and *Acinetobacter baumannii*, including multi-drug resistant (MDR) strains. Preferably, the bacteria are antibiotic resistant, and most preferably vancomycin resistant.

Conditions which can be treated with the inventive compounds, compositions and methods include, but are not limited to the following: urinary tract infections (asymptomatic bacteriuria, catheter-associated infections, urosepsis, and the like), skin and soft tissue infections (SSTIs), bacteremia, biliary tract infections (e.g., cholecystitis and cholangitis, both community acquired and hospital acquired), diverticulitis, pancreatitis, peritonitis (e.g., spontaneous bacterial peritonitis, secondary peritonitis/GI perforation, peritonitis related to peritoneal dialysis, and the like), pelvic infectious disease, prophylaxis (e.g., pre-operative and pre-procedure use, use in transplantations for donors or recipients, neutropenic patients, and the like), central line-associated blood stream infections, central line associated infections, sepsis, catheter-related blood stream infections, infective endocarditis (native valve or prosthetic valve related), infections related to permanent pacemaker (PPM), infections related to implantable cardioverter-defibrillator (ICD), meningitis, brain abscess, infections related to a central nervous system shunt, pre- and postseptal orbital cellulitis, pneumonia (naturally-occurring, health-care acquired (HAP), or ventilator-associated (VAP), infections related to cystic fibrosis (e.g., treatment of *S. aureus*), skin infections, soft tissue infections, bone infections, surgical site infections (SSIs), serious, deep tissue infections (such as necrotizing fasciitis), anthrax (cutaneous, inhalational, or gastrointestinal), and the like.

The organisms to be treated with the inventive compounds can include any bacteria, but preferably are Gram-positive bacteria. Such organisms include, but are not limited to: Gram-positive bacteria such as any species of *Staphylococcus* or *Enterococcus*, for example *Staphylococcus aureus* (including methicillin-resistant *S. aureus* (MRSA), methicillin-sensitive *S. aureus* (MSSA), vancomycin-resistant *S. aureus* (VRSA), vancomycin-intermediate *S. aureus* (VISA), daptomycin-resistant *S. aureus*, and coagulase-positive *S. aureus*); coagulase-negative *Staphylococci*, drug-resistant *Staphylococci*, *S. epidermidis*, *S. saprophyticus*, *E. faecalis*, *E. faecium*, drug-resistant *Enterococcus* spp., vancomycin-resistant *Enterococcus* (VRE), and the like. Additional preferred organisms include, but are not limited to *Bacillus* anthracia and *Acinetobacter baumannii*, including multi-drug-resistant (MDR) *A. baumannii*.

4. SUMMARY OF EXPERIMENTAL RESULTS

A structure-to-activity (SAR) study of the small molecule LII antagonist BAS00127538 has identified compound 6jc48-1, which displays improved drug-like properties compared to the parent scaffold. Compound 6jc48-1 is stable and efficacious in vivo, has low toxicity and can be administered intravenously and orally. Synthesized BAS00127538 (compound 6jc67) was found to have the same activity as the commercially available product. Compound 6jc67-A, the methyl analog of BAS00127538, also had the same activity. Using an optimized scaffold, compound 6jc48-1 was produced and found to have a 50-fold reduction in cytotoxicity compared to the parent BAS00127538 compound while retaining antimicrobial activity against

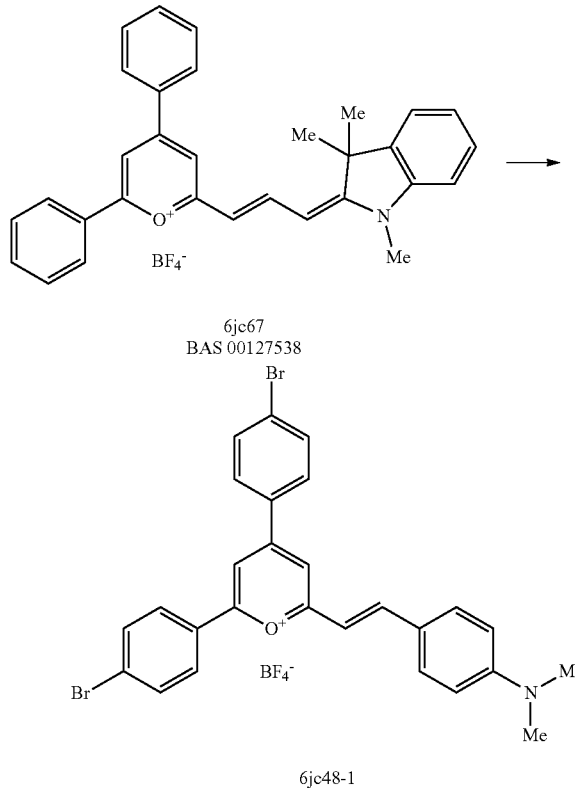

6jc67
BAS 00127538

6jc48-1 vancomycin-resistant (VRE) *Enterococci* spp.

Molecular models of BAS00127538 and compound 6jc48-1 complexed with LII, while qualitative in nature, indicate that the overall interaction pattern of the two compounds with LII are similar, though specific differences are present, suggesting that variations of the scaffold can lead to further improvements or changes in activity. The compound 6jc48-1 scaffold, together with increased understanding of scaffold functionality that impact LII interactions as well as bioavailability considerations, facilitate the development of the first small molecule antibiotic that targets LII. Therefore, the following compounds are preferred compounds contemplated as part of this invention, and are useful as antibiotic compounds for use in treatment: 6jc39, 6jc43-1, 6jc48-1, 6jc48-2, 6jc51-1, 6jc51-2, 6jc53-2, 6jc58, 6jc59-1, 6jc59-2, 6jc59-3, 6jc64-1, 6jc64-2, 6jc64-3, 6jc65-1, 6jc65-2, 6jc66-1, 6jc66-2, 6jc66-3, 6jc66-4, 6jc67, 6jc69-1, 6jc69-3, 6jc69-4, 6jc76-1, 6jc76-2, 6jc77-1, 6jc77-2, 7jc46-1, 7jc47-1, and 7jc47-2.

Preferred compounds include: 6jc48-1, 6jc58, 6jc66-3, 6jc66-4, 6jc67, 6jc77-1, 6jc77-2, 7jc46-1, 7jc47-1, and 7jc47-2, and most highly preferred compounds include: 6jc48-1, 6jc67, 7jc46-1, 7jc47-1, and 7jc47-2. See Table 5.

5. EXAMPLES

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1: Materials and Methods

A. Bacterial Strains

TABLE 1

| Bacterial Strains. | | |
|---|---|---|
| Bacterial Species | Accession Number | Source |
| *Staphylococcus aureus* | ATCC 29213 | MicrobiologicsTM (St. Cloud, MN) |
| *Escherichia coli* | ATCC 25922 | MicrobiologicsTM (St. Cloud, MN) |
| *Enterococcus faecalis* | ATCC 29212 | MicrobiologicsTM (St. Cloud, MN) |
| *Streptococcus pneumonia* | ATCC 49619 | MicrobiologicsTM (St. Cloud, MN) |
| *Acinetobacter baumanii* | ATCC 19606 | MicrobiologicsTM (St. Cloud, MN) |
| *Enterococcus faecalis* | ATCC 51575 | Laboratory of Pathology, University of Maryland Baltimore School of Medicine |
| *Enterococcus faecalis* | ATCC 51299 | Laboratory of Pathology, University of Maryland Baltimore School of Medicine |
| *Enterococcus faecalis* | REMEL C99707 | Laboratory of Pathology, University of Maryland Baltimore School of Medicine |
| *Enterococcus faecium* | ATCC 51559 (MDR) | Laboratory of Pathology, University of Maryland Baltimore School of Medicine |
| *Enterococcus faecium* | REMEL IH79985 | Laboratory of Pathology, University of Maryland Baltimore School of Medicine |
| *Enterococcus faecium* | REMEL C110914 | Laboratory of Pathology, University of Maryland Baltimore School of Medicine |

B. General Methods
1. 3-Lipid II Purification

Short-chain water-soluble LII containing a lipid tail of three isoprene units (3-LII) was generated and purified essentially according to methods known in the art. See Breukink et al., *Lipid II is an intrinsic component of the pore induced by nisin in bacterial membranes*. J. Biol. Chem. 278(22):19898-19903, 2003, the contents of which are hereby incorporated by reference. Typically, *M. flavus* vesicles (120 μmol lipid-Pi) were incubated together with 500 μmol UDP-GlcNAc, 500 μmol UDP-MurNAC-pentapeptide and 400 μmol farnesyl phosphate in 100 mM Tris-HCl pH 8.0, 5 mM $MgCl_2$. The incubation period was approximately two hours at room temperature for 3-LII (3-P). The synthesis of 3-Lipid II was followed by RP-8 reversed phase TLC (Merck™) developed with 75% methanol. For purification, the membranes were removed by centrifugation at 40,000×g; the supernatant was collected and loaded on a C18 HPLC column and eluted with a linear gradient from 50 mM ammonium bicarbonate to 100% methanol in 30 minutes. Farnesyl-Lipid II (3-Lipid II) eluted at approximately 60% methanol. Its identity was confirmed by mass spectroscopy.

2. Quality Control

Purity of the synthesized compounds was assessed was performed on a Sciex™ 6500 QTrap™ LC-MS/MS operated in Information Dependent Analysis (IDA) mode. The test compound was prepared at 5 µM and 500 nM in three matrices: 50/50 water/methanol, 50/50 water/methanol+ 0.1% formic acid and 50/50 water/methanol+10 mM ammonium bicarbonate. The IDA mass spectrometric method was designed to perform a full scan (20-700 Da) and obtain a product ion spectrum (MS/MS) from each of the 3 most abundant ions in the full scan. This IDA was run in both positive and negative mode. When operated in negative mode, a mobile phase of 50/50 water/methanol+10 mM ammonium bicarbonate was used. When operated in positive mode, a mobile phase of 50/50 water/methanol+0.1% formic acid was used. No LC column was employed, but an Agilent™ 1290 Infinity Liquid Chromatograph (Agilent Technologies™, Santa Clara, Calif.) was used to produce an isocratic flow for introduction of samples directly into the mass spectrometer. Each sample was directly injected into the mass spectrometer, via the autosampler, and the total run time for each sample was 2 minutes. Peak areas were analyzed using the Analyst software. MS/MS data were compared to full spectrum data to determine if the most abundant peaks were due to the test compound, impurity, or in-source fragmentation of the test compound. A percent purity was calculated from the ratio of the known peak areas to the total peak areas in each positive and negative mode. Calculated percent purities, in positive and negative modes, were weighted according to the total observed signal in the full scans and averaged.

3. Solubility

Solubility of compounds in water can be determined using a NEPHELOstar$^{plus}$™ laser nephelometer (BMG Labtech, Cary, N.C.) at a wavelength of 635 nm and bottom read optics using a 96-well plate format. For example, a solution of compound 6jc48-1 was prepared at a concentration of 2.5 mg/mL in DMSO. The DMSO solution (10 µl) was added to wells containing water (290 µl) for a final concentration of 125 µg/ml. The plate was incubated at room temperature for two hours prior to reading in the nephalometer. All samples were run in triplicate. Control samples (DMSO with no analyte) were prepared and run in parallel.

4. Plasma Protein Binding

Human plasma protein binding was determined using TRANSIL$^{XL}$ PPB™ plates (Sovicell, Leipzig, Germany). The compound 6jc48-1 (15 µL, 32% DMSO stock solution) was added to each well of a column (8 wells total) on a room temperature equilibrated plate. The plate was incubated for twelve minutes on a shaker at 1000 rpm then centrifuged for 10 minutes at 750×g to sediment the beads from the suspension. Aliquots (100 µl) were transferred from the supernatants to 96-well plate for MS analysis. Plasma protein binding data analysis was completed by using the supplied spreadsheet from the manufacturer (Sovicell™, User Guide TRANSIL™ PPB binding kit V2.01, 2013).

5. Animal Care

Care of the mice used in this study met or exceeded the standards set forth by the National Institutes of Health Guide for the care and use of laboratory animals and the AVMA panel on Euthanasia. All procedures in this study were approved by the Institutional Animal Care and Use Committee (IACUC) at the University of Maryland Baltimore School of Medicine. Adult C57BL/6J mice (about 18 grams, 8-10 weeks old) were used for all experiments. Mice were obtained from the Jackson Laboratory™ (Bar Harbor, Me., USA) and housed in the IHV SPC animal core facility. Mice were fed standard chow (Harlan Laboratories™) and water ad libitum.

C. Computer-Aided Drug Discovery Modeling and Molecular Dynamics Simulations

Molecular modeling, energy minimization and Molecular Dynamics (MD) simulations were performed with the program CHARMM using the CHARMM36 lipid protein and carbohydrate force field for LII; the TIP3P water model along with the CHARMM General force field was used for the ligands. Using the final snapshot from the 10 ns MD simulations of the BAS00127538-LII complex in aqueous solution the aromatic rings of the 48-1 analogs were aligned with those of BAS00127538. The system then was subjected to a short energy minimization, following which a 100 ps MD simulation with an integration time step of 0.5 fs was carried out. The system then was subjected to a 20 ns MD simulation run with a time step of 1 fs. Simulations were carried out in the NPT ensemble at 300° K and 1 Atm with SHAKE (an algorithm for applying holonomic constraints in the simulation of semiflexible molecules) of covalent bonds involving hydrogens. There were no restraints in the simulations. Free energies of binding, ΔG, were estimated using the linear interaction energy (LIE) method (see Vanommeslaeghe and Mackerell, *Automation of the CHARMM General Force Field (CGenFF) I: Bond Perception and Atom Typing.* J. Chem. Inf. Model. 52(12):3144-3154, 2012, the $$\Delta G = \alpha (\langle E_{bound}^{elec} \rangle - \langle E_{unbound}^{elec} \rangle) + \beta (\langle E_{bound}^{vdw} \rangle - \langle E_{unbound}^{vdw} \rangle) + \gamma$$

disclosures of which are hereby incorporated by reference), where
in which $\alpha=0.5$, $\beta=0.16$, $\gamma$ cancels out because only the relative free energies ($\Delta\Delta G$) were considered, and the unbound interaction energies were computed from 5 ns MD simulations of the compounds alone in water. The final structures from the simulations were used for visualization of the ligand-LII interactions.

D. Surface Plasmon Resonance Determination of Lipid II Binding

Surface Plasmon Resonance binding experiments were carried out on a BIAcore T100 system (BIAcore™ Inc., Piscataway, N.Y.) at 25° C. The assay buffer was 10 mM HEPES, 150 mM NaCl, 0.05% surfactant P20, pH 7.4 (±3 mM EDTA) supplemented with 10% DMSO. 3-Lipid II (50 RUs) was immobilized on CMS sensor chips using the amine-coupling chemistry recommended by the manufacturer. For initial determination of binding, compounds were introduced into the flow-cells (30 µl/min) in the running buffer at 10 µM. Resonance signals were corrected for nonspecific binding by subtracting the background of the control flow-cell. Binding to immobilized 3-LII on the chip surface was determined and scored "yes" in Table 5 when more than 20 Resonance Units or RUs were detected. Detection of less than 20 RUs was scored as "no", meaning no significant binding to LII. After each analysis, the sensor chip surfaces were regenerated with 50 mM NaOH for 30 seconds at a flow rate 100 µL/min, and equilibrated with the buffer prior to next injection. For binding kinetics studies, binding isotherms were analyzed with manufacturer-supplied software for BIAcore™ T100. For results, see Table 5.

E. Antibacterial Activity Assay

Determination of the Minimal Inhibitory Concentrations (MIC) by dilution was carried out by broth dilution according to CLSI standards. See CLSI, *Methods for Dilution*

*Antimicrobial Susceptibility Tests for Bacteria That Grow Aerobically; Approved Standard—Eighth Edition.* 2009, the contents of which are hereby incorporated by reference. Briefly, the minimum inhibitory concentration (MIC), is the lowest concentration of a compound that prevents visible growth of a bacterium, in other words at which it has bacteriostatic activity. The lower the MIC, the more active the compound.

F. Cytotoxicity Testing

The cytotoxicity concentration of antibacterial compounds that produces half maximal decrease in viability (CC50) against mammalian cells (HeLa, ATCC CCL-2.2) was determined as described in Butler et al., *Antibacterial activity and mechanism of action of a novel anilinouracil-fluoroquinolone hybrid compound.* Antimicrob. Agents Chemother. 51(1):119-127, 2007, the contents of which are hereby incorporated by reference. The effect of compounds on HeLa cell viability was assessed in triplicate by measuring the mitochondrial activity using MTS assays according to the manufacturer's instructions (Cell Titer 96 proliferation assay, Promega™). The cells were incubated for 72 hours in RPMI1640 medium containing the compounds at final concentrations ranging from 64 to 0.125 μg/ml. CC50 was determined using a standard curve of serially diluted untreated cells in each experiment.

G. Macromolecular Synthesis Assays

The effect of compounds on the macromolecular synthetic pathways of *E. faecalis* EF1509 were measured as follows. Cells were grown at 35° C. overnight on tryptic soy agar broth (Remel™, Lenexa, Kans.). Growth from the plate was used to inoculate 15 mL of Mueller Hinton Broth. The culture was grown to early exponential growth phase ($OD_{600}$=0.2 to 0.3) while incubating in a shaker at 35° C. and 150 rpm. For each macromolecular assay, the test agents 1499-1221 and BAS00127538 were added at either 0, 0.25-, 0.5-, 1-, 2-, or 4-fold their respective MIC values for *S. aureus* ATCC 29213. As positive control drugs, the following antibiotics were added at 8×MIC in order to validate each assay: vancomycin (which targets cell wall synthesis), ciprofloxacin (which targets DNA synthesis), rifampin (which targets RNA synthesis), cerulenin (which targets lipid synthesis), and linezolid (which targets protein synthesis).

For DNA and protein synthesis experiments, 100 μL of cell culture reaching early exponential phase was added to triplicate wells containing various concentrations of test compound or control antibiotics (2.5 μL) at 40× the final concentration in 100% DMSO (0.1% methanol in water for Rifampicin). A 2.5% DMSO-treated culture served as the "no drug" control for all experiments. Cells were added in 1.25× strength MHB to account for the volume of drug added to each reaction, or in M9 minimal medium for protein synthesis reactions. Following a 5 minute incubation at room temperature either [$^3$H]Thymidine (for DNA synthesis) or [$^3$H]leucine (for protein synthesis) was added at 0.5-1.0 μCi per reaction. Reactions were allowed to proceed at room temperature for 15-40 minutes and then stopped by adding 12 μL of cold 5% trichloroacetic acid (TCA) or 5% TCA/2% casamino acids (protein synthesis). Reactions were incubated on ice for 30 minutes and the TCA precipitated material was collected on a 25 mm GF/1.2 pin PES 96 well filter plate (Corning™). After washing five times with 200 μL per well of cold 5% TCA, the filters were allowed to dry, and then counted using a Packard™ Top Count microplate scintillation counter.

For cell wall synthesis experiments, bacterial cells in early exponential growth phase were transferred to M9 minimal medium and added to 1.5 mL Eppendorf tubes (100 μL/tube) containing various concentrations of test compound or control antibiotics (2.5 μL) at 40× the final concentration in 100% DMSO as described above. Following a 5-minute incubation at 37° C., N-acetyl-glucosamine (0.4 μCi/reaction) was added to each tube and incubated for 45 minutes in a 37° C. heating block. Reactions were stopped by addition of 100 μL of 8% sodium dodecyl(lauryl) sulfate (SDS) to each tube. Reactions were then heated at 95° C. for 30 minutes in a heating block, cooled, briefly subjected to centrifugation, and spotted onto pre-wetted hydroxylapatite (HA) filters (0.45 μM). After washing three times with 5 mL of 0.1% SDS, the filters were rinsed two times with 5 mL deionized water, allowed to dry, and then counted using a Beckman™ LS3801 liquid scintillation counter.

For lipid synthesis, bacterial cells were grown to early exponential growth phase in MHB and 100 μL was added to 1.5 mL Eppendorf tubes (in triplicate) containing various concentrations of test compound or control antibiotics as described above. Following a 5-minute incubation at room temperature, [$^3$H] glycerol was added at 0.5 μCi per reaction. Reactions were allowed to proceed at room temperature for 40 minutes and then stopped by addition of 375 μL of chloroform/methanol (1:2) followed by vortexing for 20 seconds. Chloroform (125 μL) was then added to each reaction and vortexed, followed by the addition of 125 μL $dH_2O$ and vortexing again. Reactions were centrifuged at 13,000 rpm for 10 minutes, and then 150 μL of the organic phase was transferred to a scintillation vial and allowed to dry in a fume hood for at least 1 hour. Samples then were counted using liquid scintillation counting. Each data point provided is the average of three replicates and the error bars represent standard deviation.

H. In vitro Absorption, Distribution, Metabolism, Excretion, Toxicity (ADMET) Studies For ADMET studies, liquid chromatography tandem mass spectrometry (LC-MS/MS) was used. Analysis was performed on a Sciex™ 6500 QTrap™ Triple Quadrupole Mass Spectrometer (Sciex™, Ottawa, Ontario) coupled with an Agilent™ 1290 Infinity Liquid Chromatograph (Agilent Technologies™, Santa Clara, Calif.). Separation was performed on a Halo™ C18 Column (2.7 um, 2.1 mm×50 mm) (Advanced Materials Technology™, Wilmington, Del.) with mobile phase A (methanol with 0.1% formic acid) and mobile phase B (0.1% formic acid in water). A chromatographic ramp consisting of 0 min→3 min: 95% mobile phase B→95% mobile phase A, 3 min→3.1 min: 95% mobile phase A→95% mobile phase B, 3.1 min→6 min: 95% mobile phase B was employed. The chromatographic flow rate was 500 μL/min. The autosampler compartment was held at 10° C. The mass spectrometer was operated in positive, electrospray mode using multiple reaction monitoring (MRM). The following MS settings were employed: ion source temperature, 600° C.; capillary voltage, +5500V; curtain gas, 30; collision assisted dissociation (CAD) gas, medium; ion source gas 1, 50; and ion source gas 2, 70; declustering potential, 45V; entrance potential, 10V. The ion transitions were as follows: 525.9 Da→182.7 Da, collision energy=54 eV, collision cell exit potential=24V and 525.9 Da→155.0 Da, collision energy=94 eV, collision cell exit potential=19V were monitored. Peak areas were integrated using Analyst™ software (Sciex, Ottawa, Ontario).

I. Plasma Stability

Plasma stability of compounds can be determined as follows. For the compound 6jc48-1, plasma stability was determined using heparinized, pooled human plasma (BioreclamationIVT™, Hicksville, N.Y.). The test compound was spiked into plasma at a final concentration of 1 µM. The test compound solution was subsequently incubated at 37° C. for up to 1 hour. Aliquots were removed at 0, 5, 10, 20, 30, 40, 50 and 60 minutes incubation time and diluted 1:2 in cold acetonitrile. Samples were centrifuged at 4000 rpm for 10 minutes. Supernatant was collected and diluted 1:2 in 30% methanol in water. The diluted supernatant was analyzed by LC-MS/MS using the method described above. Stability in plasma was calculated by integrating peak areas of samples using Analyst™ software (Sciex™, Ottawa, Ontario).

J. Cytochrome P450 Inhibition Testing

Cytochrome P450 inhibition testing was conducted according to the method of Paradise et al. (2007) with modifications. Briefly, drug inhibition of the test compound was measured on specific cytochrome P450 enzymes using traditional substrates for CYP3A4, CYP2D6 and CYP2C19. Recombinant human CYP450 3A4, 2D6 and 2C19 enzymes (Supersome™) were obtained from Corning®. Supersomes™ typically have a CYP450 content of 1000-2000 pmol/mL. Standard substrates (mephenytoin, dextromethorphan, testosterone) were prepared at 500 µM in acetonitrile. The final concentration of each substrate was 1 µM. Positive control inhibitors and test compounds were prepared 50× the final concentration in acetonitrile; 0.25 mM ketoconazole (inhibitor of 3A4), 25 µM quinidine (inhibitor of 2D6) and 5 mM tranylcypromine (inhibitor of 2C19). The typical $IC_{50}$ values for the standard inhibitor/substrate combinations are listed in Table 2, below. Eight concentrations of a positive control inhibitor, eight concentrations of test compound, a no inhibitor control and a background control were tested.

TABLE 2

Cytochrome P450 Inhibitor/Substrate Combinations.

| Enzyme | Substrate | Inhibitor | Time (mins) | IC50 |
| --- | --- | --- | --- | --- |
| CYP2C19 | Mephenytoin | 5 mM Tranylcypromine | 45 | 2.5 uM |
| CYP2D6 | Dextromethorphan | 25 uM Quinidine | 30 | 23 nM |
| CYP3A4 | Testosterone | 0.25 mM Ketoconazole | 15 | 60 nM |

The test compound had a final concentration range from 20 µM to single-digit nanomolar. After a 10 minute pre-incubation at 37° C., a 2× concentrated enzyme/substrate mixture was added to all samples with the exception of the background control. The enzyme/substrate solution contained 100 mM potassium phosphate buffer (pH 7.4), water, substrate and 50 pmol/ml of the respective enzyme. The reactions were quenched with acetonitrile at the appropriate time points.

All samples were centrifuged for 3 minutes at 13,000×g at room temperature. The supernatant was collected for analysis by LC-MS/MS. For computation of the $IC_{50}$ values, the background of no-enzyme samples was averaged to determine the background value. The positive control or full-reaction samples were averaged to determine the signal value. The percent activity of each sample was calculated using the following equation:

[(Test compound metabolite−average background)/ (average signal−average background)]×100=% activity.

GraphPad Prism™ software was used to plot the calculated percent activity values versus the log concentrations of test compound. The $IC_{50}$ value was calculated using non-linear regression. $IC_{50}$ values for standard inhibitors, calculated in-house, are shown in Table 2, above. Although the $IC_{50}$ values may vary slightly, literature reports demonstrate similar values (see Paradise et al., *Cytochrome P450 inhibition assays using traditional and fluorescent substrates*. Curr. Protoc. Pharmacol., 2007. Chapter 7: p. Unit7 11).

K. Liver Microsome Stability Testing

The in vitro microsome stability assay was performed using human liver microsomes and a Biomek FXP™ liquid handling workstation to deliver reagents to a deep 96-well plate on a shaking peltier with temperature controls. Human liver microsomes were purchased from Corning™. The test compound was incubated in an aqueous reaction mixture (200 µL total volume) consisting of human liver microsomes (150 mixed donor pool) and NADPH Regenerating System Solutions A and B (Corning®) in the presence of 100 mM potassium phosphate buffer (pH 7.4). NADPH Regenerating System Solution A comprises nicotinamide adenine dinucleotide phosphate (NADP+) and glucose 6-phosphate; NADPH Regenerating System Solution B contains glucose-6-phosphate dehydrogenase. Solutions A and B were combined prior to adding to the reaction plate to generate a supply of NADPH. The NADPH was added last to initiate the reactions simultaneously. The final concentration of the test compound was 10 µM and the microsomal protein concentration was 0.5 mg/ml. After incubation at 37° C., the reaction was terminated at 0, 5, 10, 20, 30, 40, 50 and 60 minutes, respectively, by the addition of 600 µL acetonitrile. Three replicates were run for each time point. The quenched reaction plate was centrifuged at 4500 rpm for 10 minutes. The supernatant was diluted 1:2 in 30% methanol in water for LC/MS/MS analyses to monitor substrate depletion. Water was substituted for NADPH for the zero time-point samples. A control plate, without NADPH cofactor, was completed on the same day, using the same conditions.

The half-life (t½) was calculated using the following equation:

$$t_{1/2} = \frac{-0.693}{\text{slope}},$$

where "slope" is the slope of the line formed by ln(% remaining test compound) vs. time. The in vitro intrinsic clearance ($CL_{int}$) was calculated using equation:

$$CL_{int} = \left(\frac{0.693}{t_{1/2}}\right)\left(\frac{\text{incubation volume (ul)}}{\text{total microsomal protein (mg)}}\right).$$

The data were compared to a positive control, dextromethorphan, which exhibited a $t_{1/2}$ of 40 minutes and an intrinsic clearance value of 31 µL/min/mg, consistent with literature values (McNaney et al., ASSAY and Drug Development Technologies, Volume 6, Number 1, 2008).

Example 2: Exemplary General Chemical Syntheses

The general strategy for preparing BAS00127538 and new analogs of BAS00127538 is shown in Schemes 1, 2 and 3 below. This method allows for independent variation of $R^1$ and the $R^2$ groups in the scaffold.

General procedure for pyrylium salt synthesis (scheme 1):

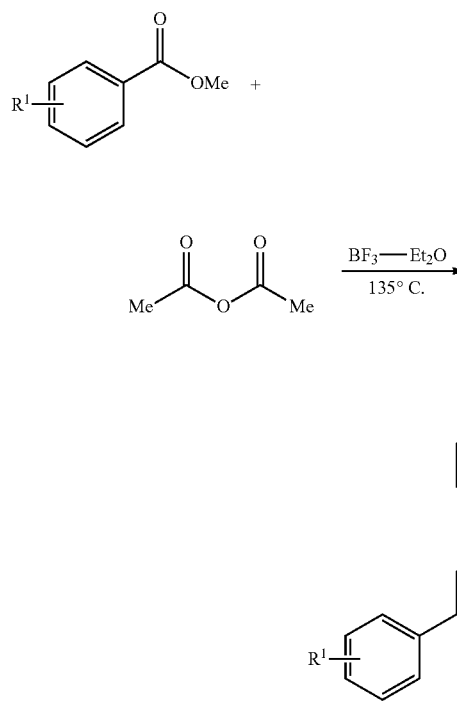

Boron trifluoride etherate (32.0 mmol) was added to a substituted acetophenone and acetic anhydride at room temperature. $R^1$ on the acetophenone can signify any desirable group or protected group for inclusion in the final product, but preferably is a halogen such as bromide or fluoride. Other salts can be used, including acetate, adipate, alginate, ammonium, aspartate, benzoate, besylate, bicarbonate, bisulfate, butyrate, citrate, camphorate, camphorsulfonate, carbonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, magnesium, maleate, malonate, mesylate, 2-naphthalenesulfonate, nicotinate, nitrate, oxalate, palmoate, pectinate, persulfate, 3-phenylpropionate, phosphate, picrate, pivalate, potassium, propionate, salicylate, sodium, succinate, sulfate, tartrate, thiocyanate, toluenesulfonate (tosylate) and undecanoate salts. The compounds described here are drawn, where appropriate, as boron tetrafluoride salts, which is a preferred salt. The reaction was heated to 135° C. for 4 hours, cooled, poured into EtOAc and allowed to stand for 1 hour. The resulting solid was filtered and washed with excess EtOAc to give the title compounds as the boron tetrafluoride salts. The $R^1$ groups can be any chemical moiety for testing, but preferably are, each independently, one or more of H, halogen, $-OR^2$, $-NHR^2$, unsubstituted or substituted $C_1$-$C_6$ alkyl, unsubstituted or substituted $C_5$-$C_7$ cycloalkyl, unsubstituted or substituted $C_4$-$C_6$ cycloheteroalkyl, unsubstituted or substituted aryl, or unsubstituted or substituted heteroaryl, and wherein the substitutions are selected from the group consisting of one or more of $C_1$-$C_5$ alkyl, $C_1$-$C_5$ alkenyl, $C_1$-$C_5$ alkynyl, amino, and halo; and wherein $R^2$ is H, alkyl, cycloalkyl, cycloheteroalkyl, aryl or heteroaryl.

General procedure for condensation reaction with aldehydes (scheme 2), wherein $R^1$ is defined as for Formula I:

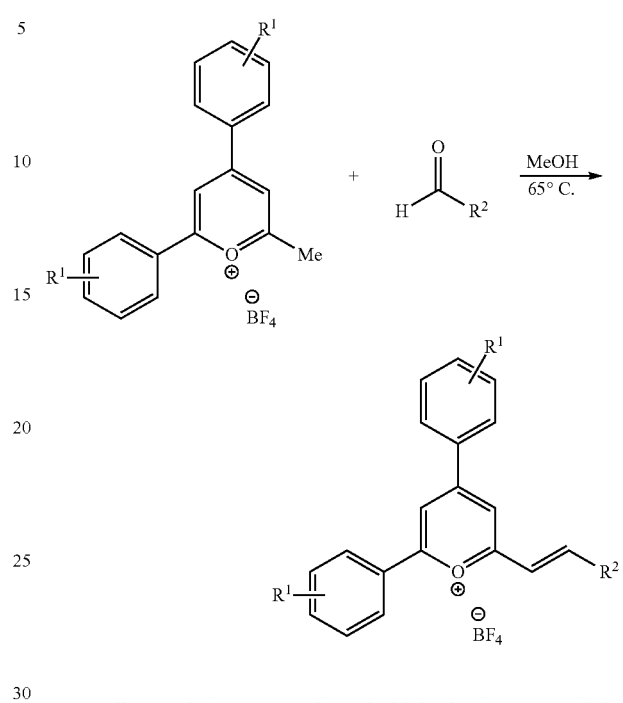

Pyrylium salt (0.28 mmol) and aldehyde (0.34 mmol) in MeOH (8 mL) was heated to reflux for 4 hours. The reaction was cooled, reduced in vacuo, poured into EtOAc and allowed to stand for 1 hour. The dark solid was filtered and washed with excess EtOAc to give the title compounds as the boron tetrafluoride salt. As discussed above, the R1 groups can be any suitable group or protected group which is desired to be part of the final compound, but preferably are, each independently, one or more of H, halogen, $-OR^2$, $-NHR^2$, unsubstituted or substituted $C_1$-$C_6$ alkyl, unsubstituted or substituted $C_5$-$C_7$ cycloalkyl, unsubstituted or substituted $C_4$-$C_6$ cycloheteroalkyl, unsubstituted or substituted aryl, or unsubstituted or substituted heteroaryl, and wherein the substitutions are selected from the group consisting of one or more of $C_1$-$C_5$ alkyl, $C_1$-$C_5$ alkenyl, $C_1$-$C_5$ alkynyl, amino, and halo; and wherein $R^2$ is H, alkyl, cycloalkyl, cycloheteroalkyl, aryl or heteroaryl.

General synthesis of the BAS00127538 scaffold showing some non-limiting preferred R group substituents for the indicated compounds is shown below:

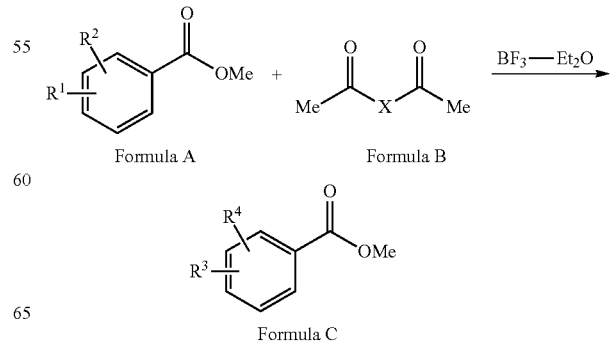

-continued

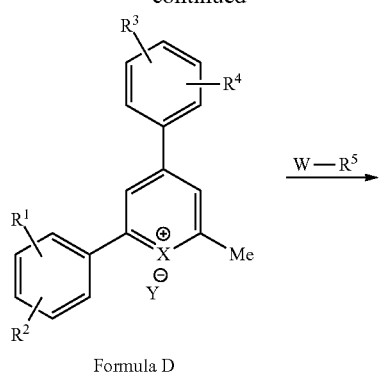

Formula D

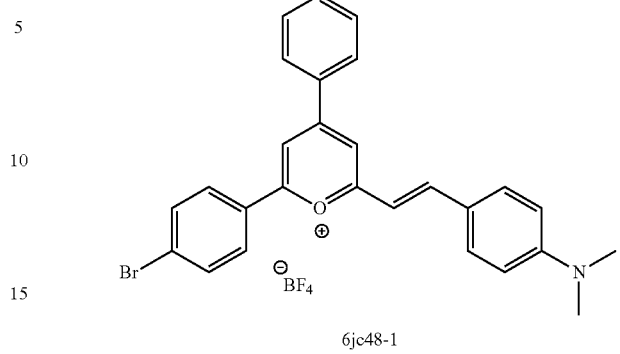

6jc48-1

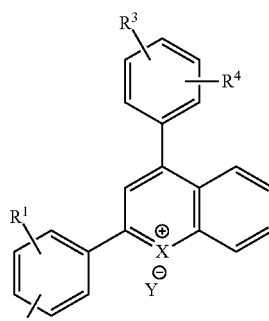

Formula I wherein $R^1$, $R^2$ $R^3$ and $R^4$ each preferably are in the meta or para position, and the $R^1$, $R^2$, $R^3$, $R^4$, W, X, and Y substituents are identified as in the general Formula I and in the specific examples presented herein. See FIG. 2. Two examples of the synthesis include:

Boron trifluoride etherate (3.68 mL, 32.0 mmol was added to a mixture of p-bromo-acetophenone (2.42 g, 12.12 mmol) and acetic anhydride (1.14 mL, 12.12 mmol) at room temperature. The reaction was heated to 135° C. for 2 hours, cooled, poured into EtOAc, and the resulting yellow solid filtered to give 705 mg. δH(MeOH-d₄, 400 MHz) 8.95 (s, 1H, Ar), 8.45 (s, 1H, Ar), 8.30 (d, 2H, J=8.8, Ar), 8.20 (d, 2H, J=8.8), 8.00-7.86 (m, 4H, Ar), 3.03 (s, 3H, Me). (100 mf, 0.20 mmol) p-dimethylamino benzaldehyde (32 mg, 0.02 mmol) in MeOH (10 mL) was added and stirred at room temperature overnight. The solvent was removed and the residue was suspended in ether and filtered to give a blue solid. Recrystallization from EtOH gave 95 mg of the named compound 6jc48-1, a blue solid. δ$_H$(DMSO-d₆, 400 MHz) 8.56 (s, 1H, Ar), 8.47 (s, 1H, Ar), 8.43-8.38 (m, 3H, Ar, HC=), 8.27 (d, 2H, J=8.4, Ar), 8.00-7.90 (m, 4H, Ar), 7.84 (d, 2H, J=8.4, Ar), 7.39 (d, 1H, J=15.6, HC=), 6.94 (d, 2H, J=8.8, Ar), 3.18 (s, 6H, 2×Me).

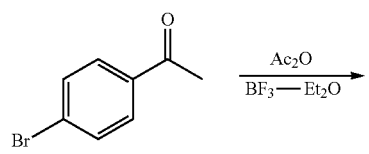

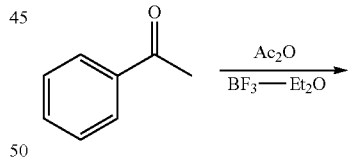

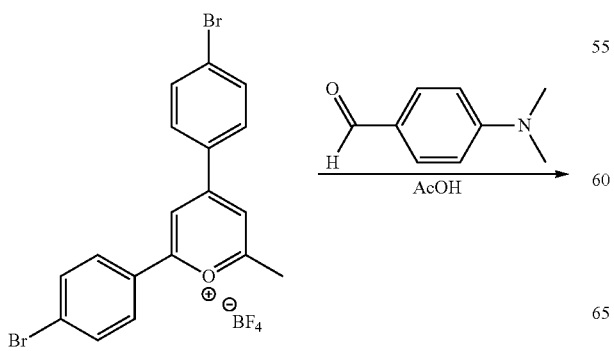

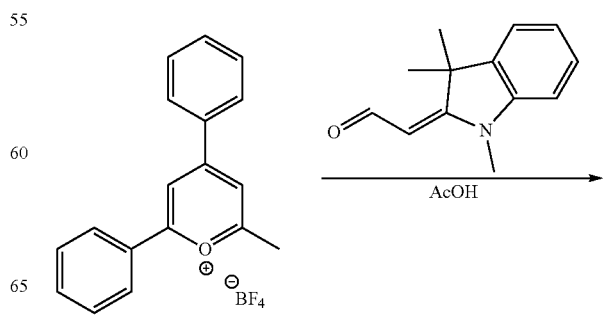

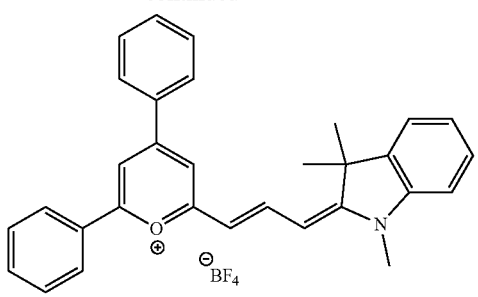

6jc67

To pyrylium salt (50 mg, 0.14 mmol) and 2-(1,3,3-trimethylindolin-2-ylidene)acetaldehyde (28 mg, 0.14 mmol) in acetic anhydride (2 mL) was stirred at reflux for 1 hr. The reaction was cooled and co-evaporated with toluene (×3), washed with ether and decanted (×2). The residue was purified by column chromatography DCM/MeOH and transferred to a vial to give a blue solid 69 mg. $\delta_H$(DMSO-$d_6$, 400 MHz) 8.47 (t, 1H, J=13.2, HC=), 8.26-8.10 (m, 4H, Ar), 7.95 (s, 1H, Ar), 7.90-7.59 (m, 8H, Ar), 7.53-7.44 (m, 2H, Ar), 7.35 (t, 1H, J=7.6, Ar), 6.58 (d, 1H, J=13.2, HC=), 6.39 (br s, 1H, HC=), 3.73 (s, 3H, NMe), 1.74 (s, 6H, 2×CH$_3$).

Example 3: De Novo Synthesis of Compound 6jc48-1

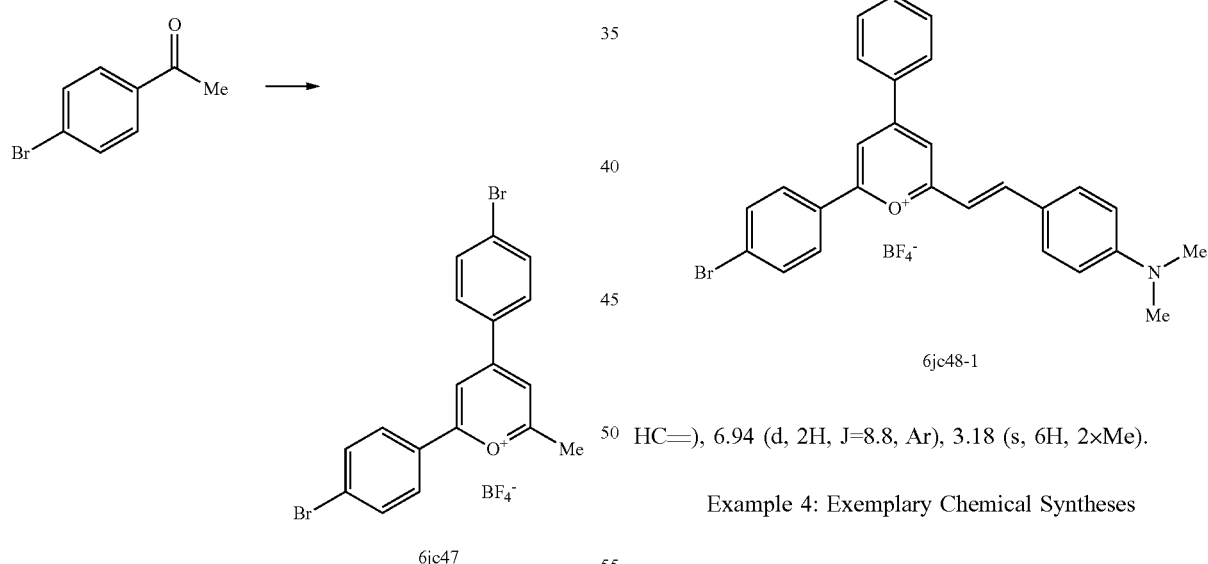

Boron trifluoride etherate (3.68 mL, 32.0 mmol was added to a mixture of p-bromo-acetophenone (2.42 g, 12.12 mmol) and acetic anhydride (1.14 mL, 12.12 mmol) at room temperature. The reaction was heated to 135° C. for 2 hours, cooled, poured into EtOAc, and the resulting yellow solid filtered to give 705 mg. $\delta_H$(MeOH-$d_4$, 400 MHz) 8.95 (s, 1H, Ar), 8.45 (s, 1H, Ar), 8.30 (d, 2H, J=8.8, Ar), 8.20 (d, 2H, J=8.8), 8.00-7.86 (m, 4H, Ar), 3.03 (s, 3H, Me). 2,4-bis(4-bromophenyl)-6-methylpyrylium boron tetrafluoride salt, Compound 6jc47.

To compound 6jc47 (100 mf, 0.20 mmol), p-dimethylamino benzaldehyde (32 mg, 0.02 mmol) in MeOH (10 mL) was added and stirred at room temperature overnight. The solvent was removed and the residue was suspended in ether and filtered to give a blue solid. Recrystallization from EtOH gave 95 mg of the named compound 6jc48-1, a blue solid. $\delta_H$(DMSO-$d_6$, 400 MHz) 8.56 (s, 1H, Ar), 8.47 (s, 1H, Ar), 8.43-8.38 (m, 3H, Ar, HC=), 8.27 (d, 2H, J=8.4, Ar), 8.00-7.90 (m, 4H, Ar), 7.84 (d, 2H, J=8.4, Ar), 7.39 (d, 1H, J=15.6, HC=), 6.94 (d, 2H, J=8.8, Ar), 3.18 (s, 6H, 2×Me).

Example 4: Exemplary Chemical Syntheses

Example 4A: Compound 6jc26; 2-methyl-4,6-diphenylpyrylium boron tetrafluoride Salt

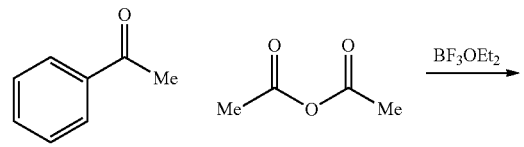

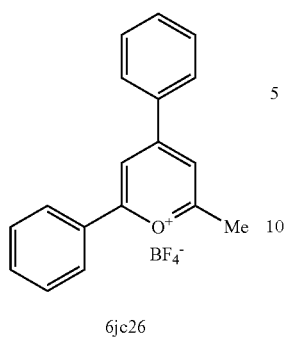

6jc26

Boron trifluoride etherate (3.40 mL, 22.50 mmol) was added to acetophenone (2 g, 1667 mmol) and acetic anhydride (1.57 mL, 16.67 mmol) at room temperature. The reaction mixture was heated to 135° C. for 2 hours, cooled, poured into EtOAc, and the resulting yellow solid filtered. Recrystallization from AcOH gave 813 mg yellow solid.

$\delta_H$(MeOH-d4, 400 MHz) 8.95 (s, 1H, Ar), 8.43 (s, 1H, Ar), 8.41 (d, 2H, J=8.0), 8.30 (d, 2H, J=8.0), 7.82 (t, 2H, J=7.2, Ar), 7.73 (t, 4H, J=7.6, Ar), 3.04 (s, 3H, Me, exchanges with deuterium over time).

Example 4B: Compound 6jc32-1; 2,4-bis(4-chlorphenyl)-6-methylpyrylium boron tetrafluoride Salt

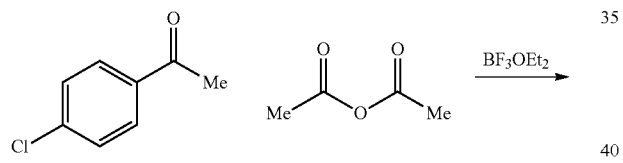

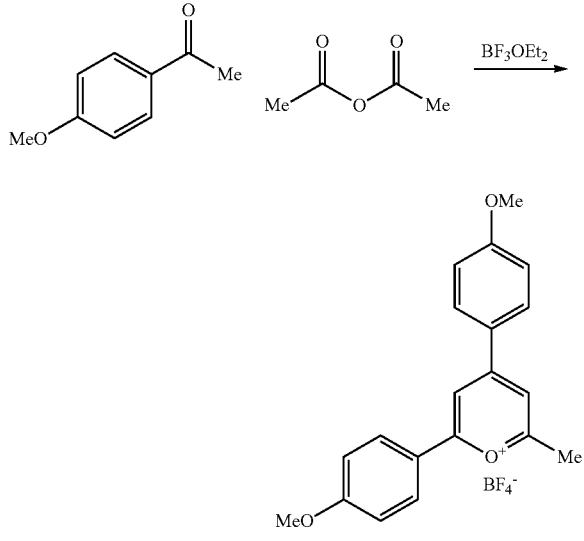

6jc32-1

Boron trifluoride etherate (4 mL, 32.0 mmol) was added to p-chloro-acetophenone (2 g, 13.0 mmol) and acetic anhydride (1.22 mL, 13.0 mmol) at room temperature. The reaction was heated to 135° C. for 2 hours, cooled, poured into EtOAc, and the resulting yellow solid filtered to give 644 mg of the title compound.

$\delta_H$(MeOH-d4, 400 MHz) 8.95 (s, 1H, Ar), 8.44 (s, 1H, Ar), 8.40 (d, 2H, J=8.8), 8.29 (d, 2H, J=8.8), 7.75 (d, 4H, J=7.2, Ar), 3.04 (s, 3H, Me).

Example 4C: Compound 6jc32-2; 2,4-bis(4-methoxyphenyl)-6-methylpyrylium boron tetrafluoride Salt 6jc32-2

Boron trifluoride etherate (4 mL, 32.0 mmol) was added to p-methoxy-acetophenone (2 g, 13.0 mmol) and acetic anhydride (1.22 mL, 13.0 mmol) at room temperature. The reaction was heated to 135° C. for 2 hours, cooled, poured into EtOAc, and the resulting red solid filtered to give 313 mg of the title compound.

$\delta_H$(MeOH-$d_4$, 400 MHz) 8.67 (s, 1H, Ar), 8.44 (s, 1H, Ar), 8.37 (d, 2H, J=89.6), 8.32 (d, 2H, J=9.2), 8.15 (s, 1H, Ar), 7.25-7.21 (m, 4H, Ar), 3.97 (s, 3H, OMe), 3.96 (s, 3H, OMe), 2.91 (s, 3H, Me).

Example 4D: Compound 6jc36: 2,4,6-trimethylpyrylium boron tetrafluoride Salt

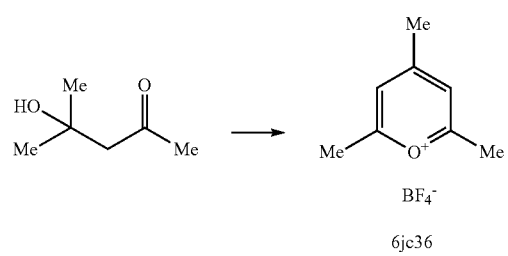

6jc36

Boron trifluoride etherate (2.5 mL, 10.0 mmol) was added to pentanone (1.16 g, 10.0 mmol) and acetic anhydride (9.5 mL, 100.0 mmol) at room temperature. The reaction was heated to 135° C. for 2 hours, cooled, poured into EtOAc, and the resulting white solid filtered to give 980 mg of the title compound.

$\delta_H$(MeOH-$d_4$, 400 MHz) 7.86 (s, 2H, Ar), 2.89 (s, 6H, 2×Me), 2.70 (s, 3H, Me).

Example 4E: Compound 6jc37: (E)-4-(4-(dimethylamino)styryl)-2,6-dimethylpyrylium boron tetrafluoride Salt

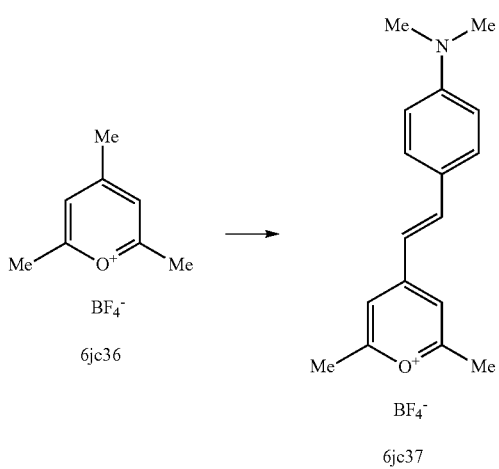

p-dimethylamino benzaldehyde (150 mg, 1.00 mmol) was added to pyrylium salt 6jc36 (210 mg, 1.00 mmol) in MeOH (10 mL) at room temperature overnight. The solvent was removed and the residue was suspended in ether and filtered to give blue solid. Recrystallization from EtOH yielded 110 mg of the blue solid title compound.

$\delta_H$(DMSO-$d_6$, 400 MHz) 8.35 (d, 1H, J=14.8, H-vinyl), 7.76 (d, 2H, J=8.4, Ar), 7.69 (s, 2H, Ar), 7.13 (d, 1H, J=14.8, H-vinyl), 6.91 (d, 2H, J=8.4, Ar), 3.16 (s, 6H, 2×Me), 2.63 (s, 6H, NMe$_2$).

Example 4F: Compound 6jc38; 4-((1E,3E)-4-(4-(dimethylamino)phenyl)buta-1,3-dien-1-yl)-2,6-dimethylpyrylium boron tetrafluoride Salt

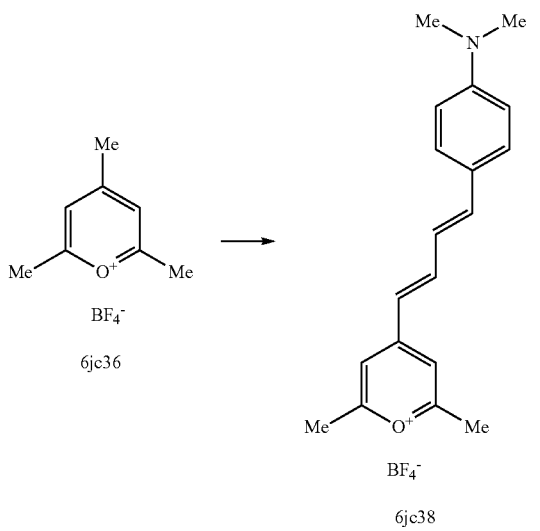

p-dimethylamino benzaldehyde$_{176}$ mg. 1.00 mmol) and pyrylium salt 6jc36 (210 mg, 1.00 mmol) were stirred in MeOH (10 mL) at room temperature overnight. The solvent was removed and the residue was suspended in ether and filtered to give blue solid. Recrystallization from EtOH gave green solid of 110 mg.

$\delta_H$(DMSO-$d_6$, 400 MHz) 8.25 (dd, 1H, J=14.8, 14.4, H-vinyl), 7.73 (s, 2H, Ar), 7.65 (d, 2H, J=8.8, Ar), 7.39 (d, 1H, J=14.8, H-vinyl), 7.27 (t, 1H, J=14.8, H-vinyl), 6.81 (d, 2H, J=8.8, Ar), 6.63 (d, 1H, J=14.4, H-vinyl), 3.10 (s, 6H, 2×Me), 2.64 (s, 6H, NMe$_2$).

Example 4G: Compound 6jc39; (E)-2-(4-(dimethylamino)styryl)-4,6-diphenylpyrylium boron tetrafluoride

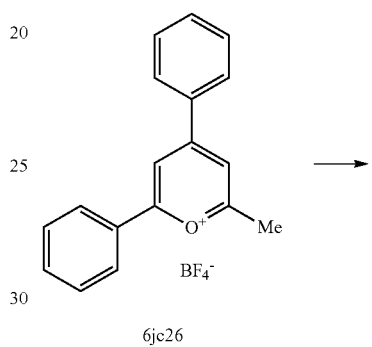

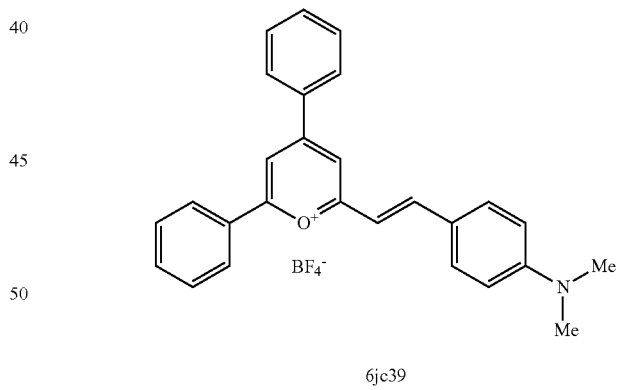

Pyrylium salt 6jc26 (100 mg, 0.30 mmol) and p-dimethylamino benzaldehyde (50 mg, 0.32 mmol) in MeOH (6 mL) were stirred at room temperature overnight. The solvent was removed and the residue suspended in ether and filtered to give 81 mg of green solid.

$\delta_H$(DMSO-$d_6$, 400 MHz) 8.62 (s, 1H, Ar), 8.51-8.42 (m, 4H, Ar, HC=), 8.34 (d, 2H, J=7.2, Ar), 7.86 (d, 2H, J=9.6, Ar), 7.84-7.70 (m, 6H, Ar), 7.42 (d, 1H, J=15.6, HC=), 6.93 (d, 2H, J=8.4, Ar), 3.17 (s, 6H, 2×Me).

Example 4H: Compound 6jc41; (E)-2,4-bis(4-chlorophenyl)-6-(4-(dimethylamino)styryl) pyrylium boron tetrafluoride Salt

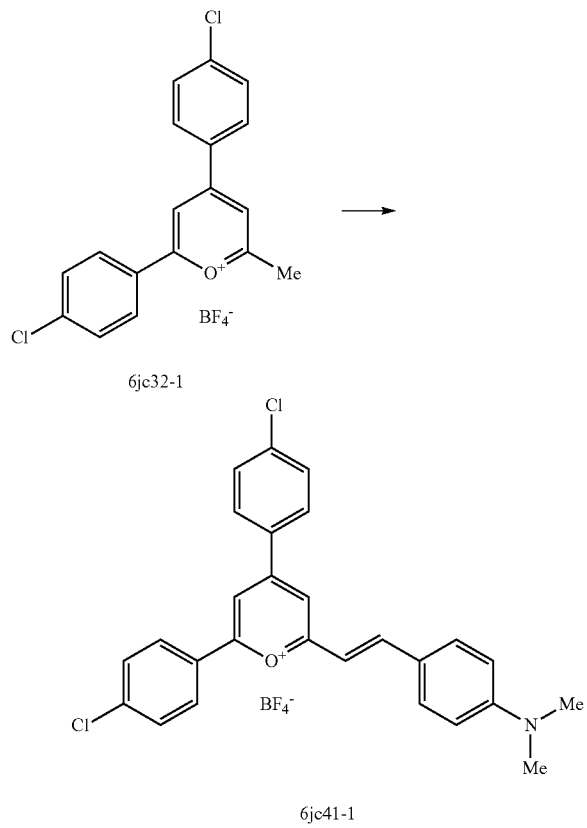

Pyrylium salt 6jc32-1 (134 mg, 0.33 mmol) and p-dimethylamino benzaldehyde (50 mg, 0.33 mmol) in MeOH (6 mL) were stirred at room temperature overnight. The solvent was removed and the residue suspended in ether and filtered to give dark blue solid of 105 mg.

$\delta_H$(DMSO-$d_6$, 400 MHz) 8.57 (s, 1H, Ar), 8.49-8.40 (m, 4H, Ar, HC=), 8.34 (d, 2H, J=8.4, Ar), 7.84-7.77 (m, 6H, Ar), 7.37 (d, 1H, J=15.6, HC=), 6.92 (d, 2H, J=8.4, Ar), 3.17 (s, 6H, 2×Me).

Example 4I: Compound 6jc43-1; 2-((1E,3E)-4-(4-(dimethylamino)phenyl)buta-1,3-dien-1-yl)-4,6-diphenylpyrylium boron tetrafluoride Salt

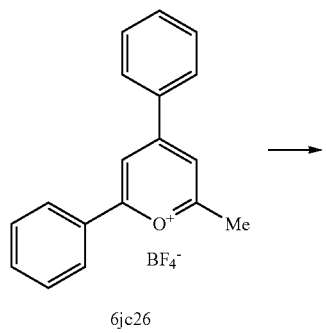

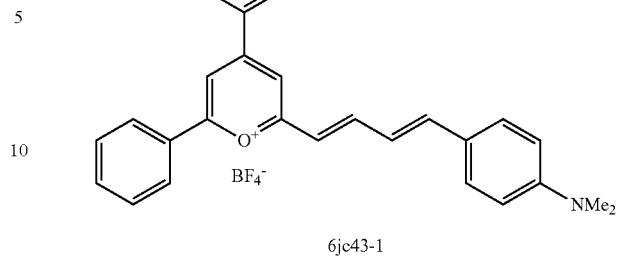

Pyrylium salt 6jc26 (94 mg, 0.28 mmol) and p-dimethylamino cinnamaldehyde (60 mg, 0.34 mmol) in MeOH (8 mL) were heated to reflux for 2 hours. The reaction was cooled, the solvent removed and the residue was suspended in ether, washed with EtOAc and filtered to give dark blue solid of 55 mg.

$\delta_H$(DMSO-$d_6$, 400 MHz) 8.67 (s, 1H, Ar), 8.54-8.44 (m, 3H, Ar), 8.36 (d, 2H, J=8.0, Ar), 8.31 (t, 1H, J=14.8, H-vinyl), 7.85-7.70 (m, 6H, Ar), 7.65 (d, 2H, J=8.4, Ar), 7.57 (d, 1H, J=14.8, H-vinyl), 7.31 (t, 1H, J=14.8, H-vinyl), 6.88 (d, 1H, J=14.8, H-vinyl), 6.83 (d, 2H, J=8.4, Ar), 3.09 (s, 6H, NMe$_2$).

Example 4J: Compound 6jc43-2; 2,4-bis(4-chlorophenyl)-6-((1E,3E)-4-(4-(dimethylamino)

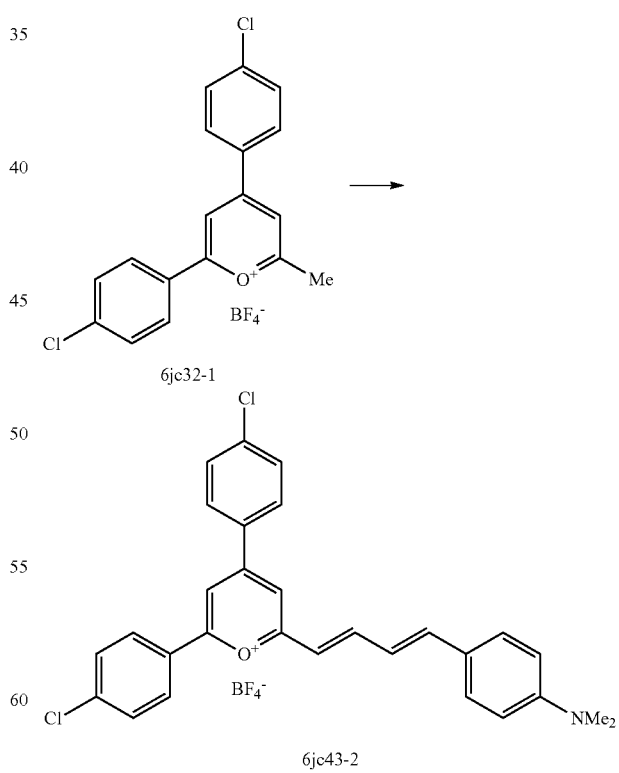

phenyl)buta-1,3-dien-1-yl)pyrylium boron tetrafluoride Salt

Pyrylium salt 6jc32-1 (112 mg, 0.28 mmol) and p-dimethylamino cinnamaldehyde (60 mg, 0.34 mmol) in MeOH (8 mL) were heated to reflux for 2 hours. The reaction was cooled, the solvent removed and the residue suspended in ether, washed with EtOAc and filtered to give dark blue solid of 46 mg.

$\delta_H$(DMSO-$d_6$, 400 MHz) 8.62 (s, 1H, Ar), 8.54-8.44 (m, 3H, Ar), 8.37 (d, 2H, J=7.2, Ar), 8.28 (t, 1H, J=13.6, H-vinyl), 7.89-7.72 (m, 4H, Ar), 7.64 (d, 2H, J=8.0, Ar), 7.55 (d, 1H, J=15.2, H-vinyl), 7.30 (t, 1H, J=13.2, H-vinyl), 6.69-6.73 (m, 3H, Ar, H-vinyl), 3.10 (s, 6H, NMe$_2$).

Example 4K: Compound 6jc48-2; 2,4-bis(4-bromophenyl)-6-((1E,3E)-4-(4-(dimethylamino) phenyl) buta-1,3-dien-1-yl)pyrylium boron tetrafluoride Salt

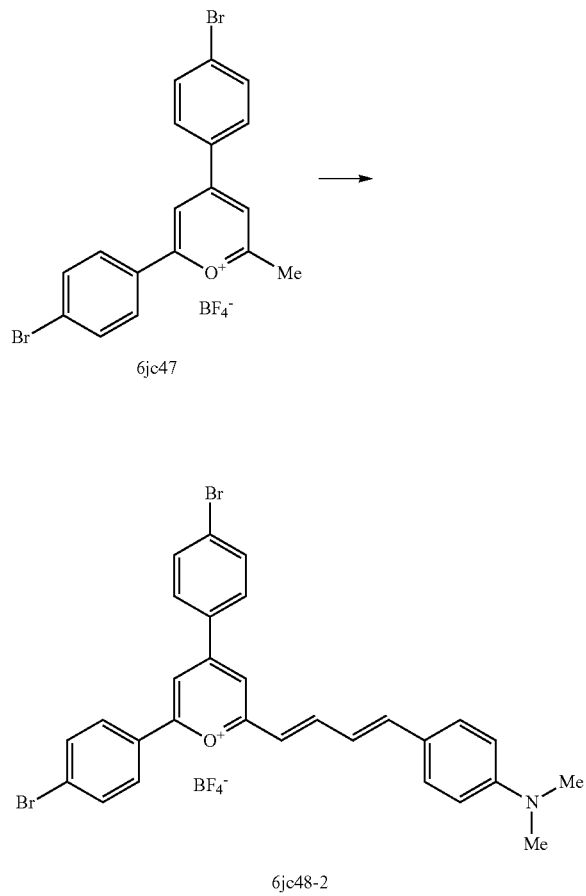

Pyrylium salt 6jc47 (100 mg, 0.20 mmol) and p-dimethylamino cinnamaldehyde (38 mg, 0.20 mmol) in MeOH (10 mL) was stirred at room temperature overnight. The solvent was removed and the residue was suspended in ether and filtered to give blue solid. Recrystallization from EtOH gave blue solid of 41 mg.

$\delta_H$(DMSO-$d_6$, 400 MHz) 8.64 (s, 1H, Ar), 8.49 (s, 1H, Ar), 8.39 (d, 2H, J=8.4, Ar), 8.35-8.24 (m, 3H, Ar, HC=), 8.00-7.89 (m, 4H, Ar), 7.65 (d, 2H, J=8.4, Ar), 7.56 (d, 1H, J=14.8, HC=), 7.32 (t, 1H, J=14.8, HC=), 6.90-6.81 (m, 3H, Ar, HC=), 3.10 (s, 6H, NMe$_2$).

Example 4L: Compound 6jc49-1; (E)-2-(2-(1H-indol-3-yl)vinyl)-4,6-diphenylpyrylium boron tetrafluoride Salt

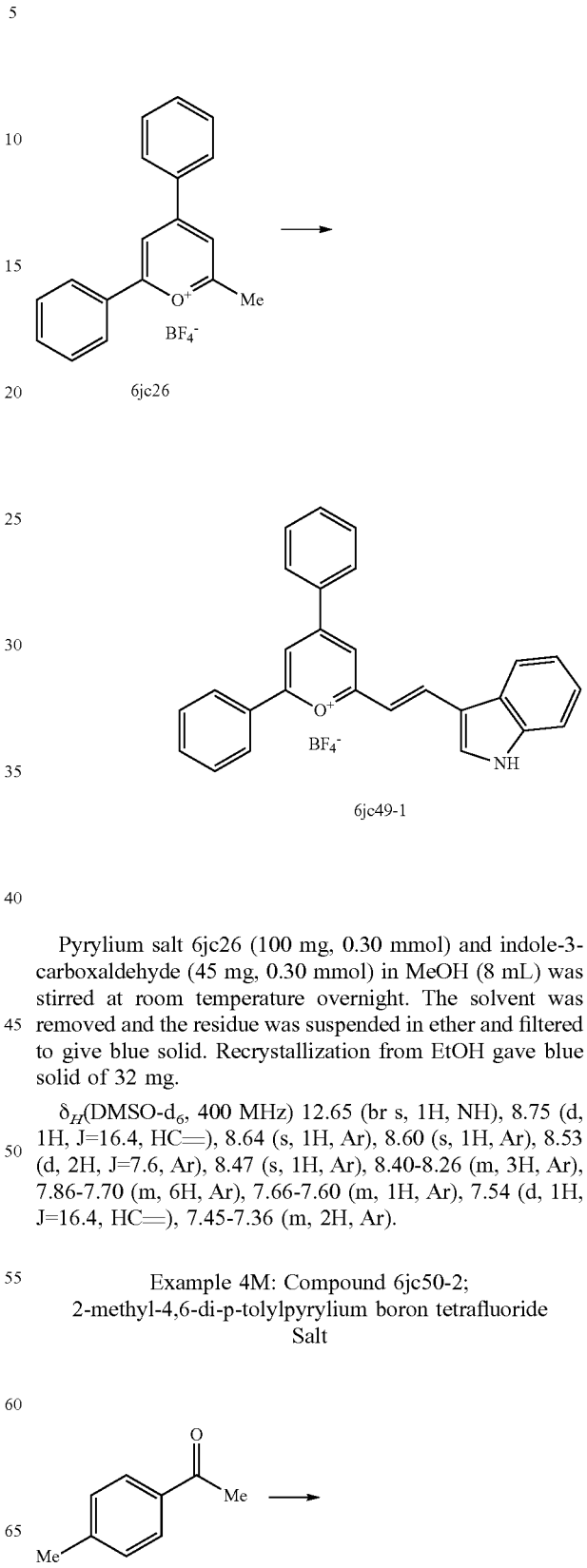

Pyrylium salt 6jc26 (100 mg, 0.30 mmol) and indole-3-carboxaldehyde (45 mg, 0.30 mmol) in MeOH (8 mL) was stirred at room temperature overnight. The solvent was removed and the residue was suspended in ether and filtered to give blue solid. Recrystallization from EtOH gave blue solid of 32 mg.

$\delta_H$(DMSO-$d_6$, 400 MHz) 12.65 (br s, 1H, NH), 8.75 (d, 1H, J=16.4, HC=), 8.64 (s, 1H, Ar), 8.60 (s, 1H, Ar), 8.53 (d, 2H, J=7.6, Ar), 8.47 (s, 1H, Ar), 8.40-8.26 (m, 3H, Ar), 7.86-7.70 (m, 6H, Ar), 7.66-7.60 (m, 1H, Ar), 7.54 (d, 1H, J=16.4, HC=), 7.45-7.36 (m, 2H, Ar).

Example 4M: Compound 6jc50-2; 2-methyl-4,6-di-p-tolylpyrylium boron tetrafluoride Salt

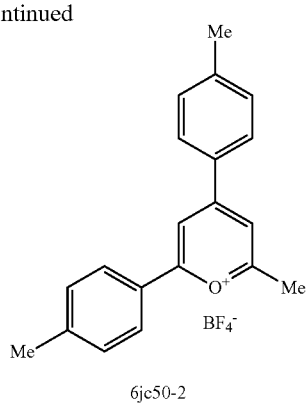

6jc50-2

Boron trifluoride etherate (4.55 mL, 36.9 mmol) was added to p-methyl-acetophenone (2.00 g, 15.0 mmol) and acetic anhydride (1.40 mL, 15.0 mmol) was added at room temperature. The reaction was heated to 135° C. for 2 hours, cooled, poured into EtOAc and the yellow solid filtered to give 609 mg.

$\delta_H$(MeOH-d$_4$, 400 MHz) 8.83 (s, 1H, Ar), 8.32 (s, 1H, Ar), 8.29 (d, 2H, J=8.0, Ar), 8.20 (d, 2H, J=8.0, Ar), 7.59-7.50 (m, 4H, Ar), 2.98 (s, 3H, Me), 2.50 (s, 6H, 2×Me).

Example 4N: Compound 6jc51-1; (E)-2-(4-(dimethylamino)styryl)-4,6-di-p-tolylpyrylium boron tetrafluoride Salt

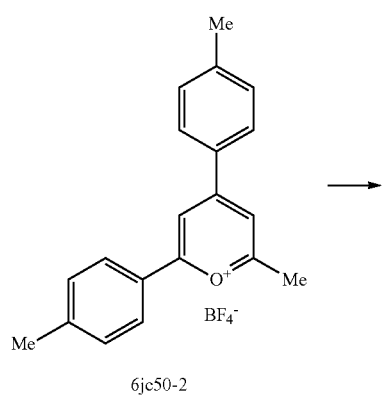

6jc51-1

Pyrylium salt 6jc50-2 (100 mg, 0.27 mmol) and p-dimethylamino benzaldehyde (43 mg, 0.27 mmol) in MeOH (8 mL) were stirred at room temperature overnight. The solvent was removed and the residue was suspended in ether and filtered to give blue solid. Recrystallization from EtOH gave blue solid of 73 mg.

$\delta_H$(DMSO-d$_6$, 400 MHz) 8.58 (s, 1H, Ar), 8.43 (s, 1H, Ar), 8.42-8.35 (m, 3H, Ar, HC=), 8.28 (d, 2H, J=8.0, Ar), 7.83 (d, 2H, J=8.8, Ar), 7.58-7.50 (m, 4H, Ar), 7.38 (d, 1H, J=15.6, HC=), 6.91 (d, 2H, J=8.8, Ar), 3.15 (s, 6H, NMe$_2$), 2.49 (s, 6H, 2×Me).

Example 4O: Compound 6jc51-2; 2-((1E,3E)-4-(4-(dimethylamino)phenyl)buta-1,3-dien-1-yl)-4,6-di-p-tolylpyrylium boron tetrafluoride Salt

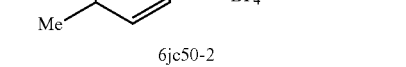

6jc50-2

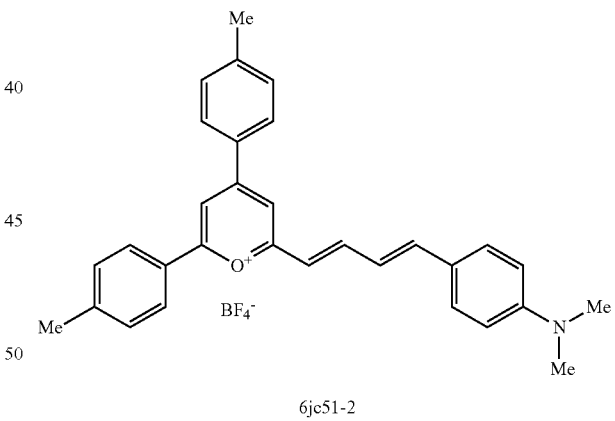

6jc51-2

Pyrylium salt 6jc50-2 (100 mg, 0.27 mmol) and p-dimethylamino cinnamaldehyde (50 mg, 0.27 mmol) in MeOH (8 mL) was stirred at room temperature overnight. The solvent was removed and the residue was suspended in ether and filtered to give blue solid. Recrystallization from EtOH gave blue solid of 58 mg.

$\delta_H$(DMSO-d$_6$, 400 MHz) 8.63 (s, 1H, Ar), 8.44 (s, 1H, Ar), 8.39 (d, 2H, J=7.6, Ar), 8.31 (d, 2H, J=7.6, Ar), 8.24 (t, 1H, HC=), 7.62 (d, 2H, J=8.8, Ar), 7.58-7.43 (m, 5H, Ar, HC=), 7.27 (t, 1H, J=14.8, HC=), 6.90-6.78 (m, 3H, Ar, HC=), 3.08 (s, 6H, NMe$_2$), 2.49 (s, 6H, 2×Me).

Example 4P: Compound 6jc53-1; (E)-2-(2-(1H-indol-3-yl)vinyl)-4,6-bis(4-chlorophenyl) pyrylium boron tetrafluoride Salt

Example 4Q: Compound 6jc53-2; (E)-2-(2-(1H-indol-3-yl)vinyl)-4,6-di-p-tolylpyrylium boron tetrafluoride Salt

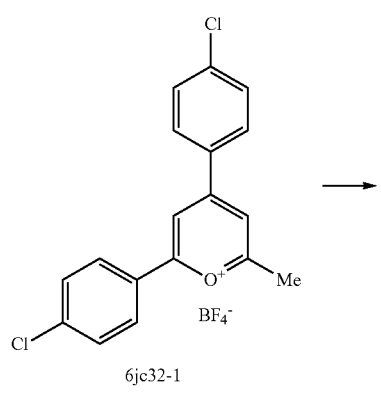

6jc32-1

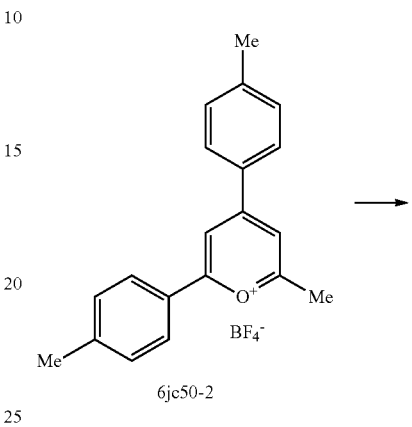

6jc50-2

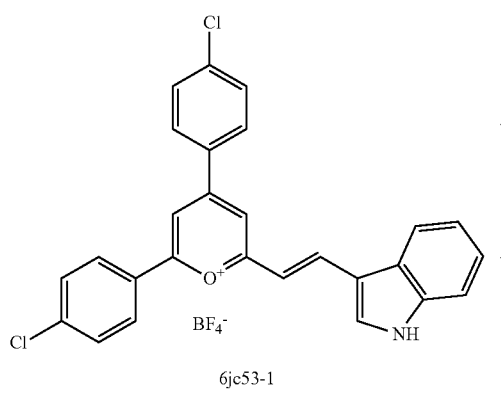

6jc53-1

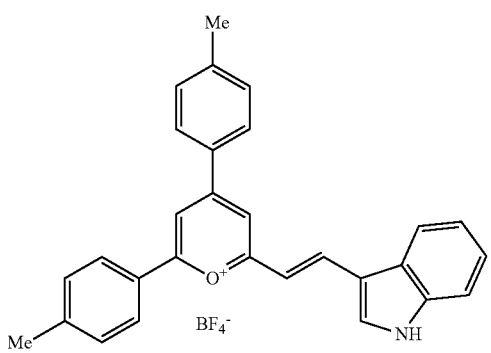

6jc53-2

Pyrylium salt 6jc32-1 (138 mg, 0.34 mmol) and indole-3-carboxaldehyde (50 mg, 0.34 mmol) in MeOH (8 mL) was stirred at room temperature overnight. The solvent was removed and the residue was suspended in ether and filtered to give blue solid. Recrystallization from EtOH gave purple solid of 53 mg.

$\delta_H$(DMSO-$d_6$, 400 MHz) 12.70 (br s, 1H, NH), 8.78 (d, 1H, J=14.8, HC=), 8.64 (s, 1H, Ar), 8.61 (s, 1H, Ar), 8.53 (d, 2H, J=8.4, Ar), 8.47 (s, 1H, Ar), 8.37 (d, 2H, J=8.8, Ar), 8.31-8.26 (m, 1H, Ar), 7.89-7.80 (m, 4H, Ar), 7.68-7.60 (m, 1H, Ar), 7.52 (d, 1H, J=14.8, HC=), 7.45-7.36 (m, 2H, Ar).

Pyrylium salt 6jc50-2 (123 mg, 0.34 mmol) and indole-3-carboxaldehyde (50 mg, 0.34 mmol) in MeOH (8 mL) was stirred at room temperature overnight. The solvent was removed and the residue was suspended in ether and filtered to give blue solid. Recrystallization from EtOH gave purple solid of 50 mg.

$\delta_H$(DMSO-$d_6$, 400 MHz) 12.55 (br s, 1H, NH), 8.68 (d, 1H, J=15.6 HC=), 8.60 (s, 1H, Ar), 8.55 (s, 1H, Ar), 8.46-8.40 (m, 3H, Ar), 8.30-8.22 (m, 3H, Ar), 7.66-7.53 (m, 5H, Ar), 7.50 (d, 1H, J=15.6, HC=), 7.43-7.35 (m, 2H, Ar), 2.50 (2×Me).

Example 4R: Compound 6jc53-3; (E)-2-(2-(1H-indol-3-yl)vinyl)-4,6-bis(4-bromophenyl) pyrylium boron tetrafluoride Salt

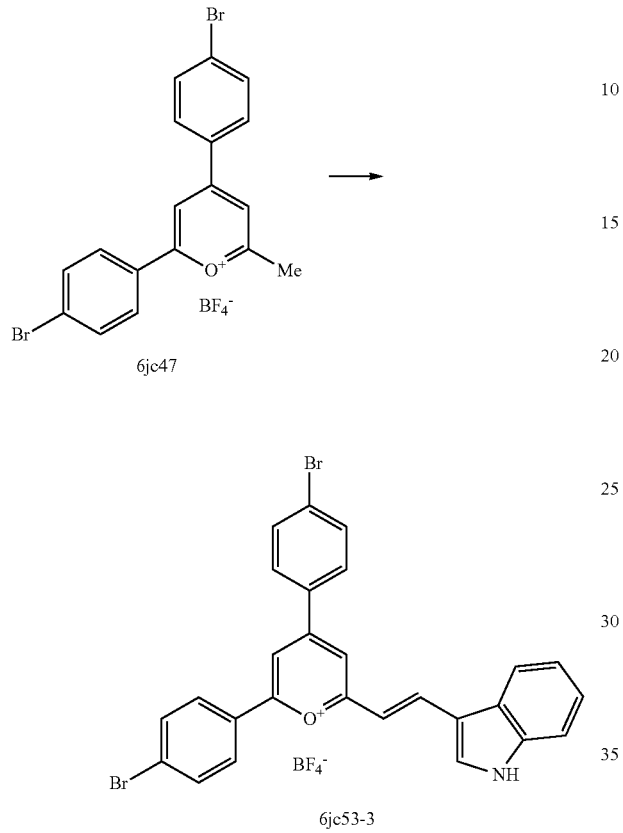

Pyrylium salt 6jc47 (169 mg, 0.34 mmol) and indole-3-carboxaldehyde (50 mg, 0.34 mmol) in MeOH (8 mL) was stirred at room temperature overnight. The solvent was removed and the residue was suspended in ether and filtered to give blue solid. Recrystallization from EtOH gave purple solid of 38 mg.

$\delta_H$(DMSO-d$_6$, 400 MHz) 12.70 (br s, 1H, NH), 8.79 (d, 1H, J=14.8, HC=), 8.64 (s, 1H, Ar), 8.62 (s, 1H, Ar), 8.50-8.42 (m, 3H, Ar), 8.43-8.24 (m, 3H, Ar), 8.04-7.92 (m, 4H, Ar), 7.66-7.60 (m, 1H, Ar), 7.52 (d, 1H, J=14.8, HC=), 7.45-7.36 (m, 2H, Ar).

Example 4S: Compound 6jc56; 2,4-bis(4-(tert-butyl)phenyl)-6-methylpyrylium boron tetrafluoride Salt

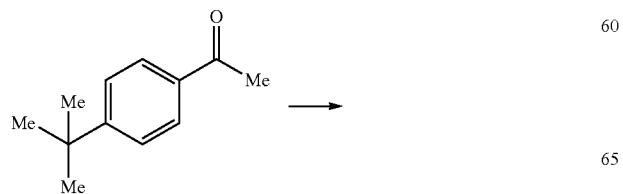

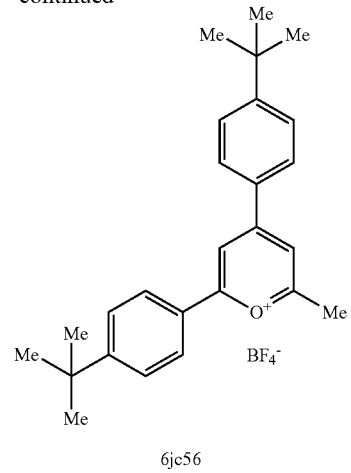

Boron trifluoride etherate (3.46 mL, 28.0 mmol) was added to p-tButyl-acetophenone (2.00 g, 11.4 mmol) and acetic anhydride (1.07 mL, 11.4 mmol) at room temperature. The reaction was heated to 135° C. for 2 hours, cooled, poured into EtOAc and the yellow solid filtered to give 494 mg.

$\delta_H$(MeOH-d$_4$, 400 MHz) 8.86 (s, 1H, Ar), 8.36-8.32 (m, 3H, Ar), 8.26 (d, 2H, J=8.8, Ar), 7.77 (d, 4H, J=7.6, Ar), 3.00 (s, 3H, Me), 1.40 (s, 18H, 2×tBu).

Example 4T: Compound 6jc57; 2,4-bis(3,4-dimethylphenyl)-6-methylpyrylium boron tetrafluoride Salt

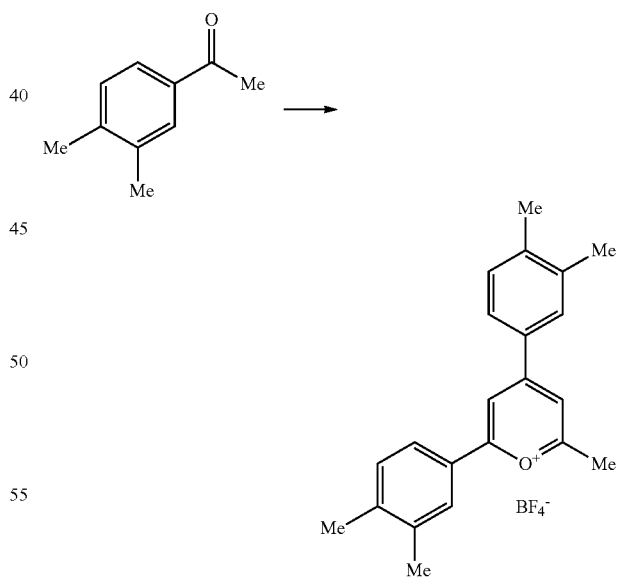

Boron trifluoride etherate (4.10 mL, 33.2 mmol) was added to 3,4-dimethyl-acetophenone (2.00 g, 13.5 mmol) and acetic anhydride (1.28 mL, 13.5 mmol) at room temperature. The reaction was heated to 135° C. for 3 hours, cooled, poured into EtOAc and the yellow solid filtered to give 417 mg.

δ$_H$(MeOH-d$_4$, 400 MHz) 8.82 (s, 1H, Ar), 8.30 (s, 1H, Ar), 8.16-8.09 (m, 2H, Ar), 8.05 (d, 1H, J=7.6, Ar), 7.48 (d, 2H, J=8.0, Ar), 2.97 (s, 3H, Me), 2.44 (s, 6H, 2×Me), 2.42 (s, 6H, 2×Me).

Example 4U: Compound 6jc58; (E)-2-(2-(1,2,3,5,6,7-hexahydropyrido[3,2,1-ij]quinolin-9-yl)vinyl)-4,6-diphenylpyrylium boron tetrafluoride Salt

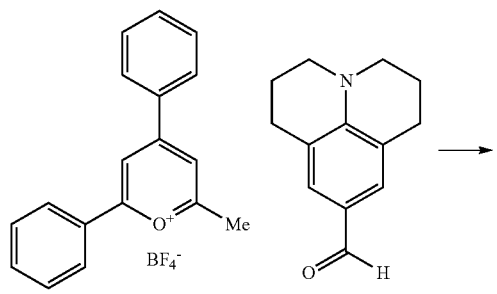

6jc26

Example 4V: Compound 6jc59-1; (E)-2-(4-(dimethylamino)styryl)-4,6-bis(3,4-dimethylphenyl)pyrylium boron tetrafluoride Salt

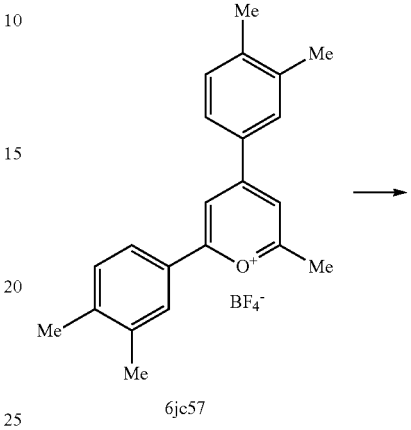

6jc57

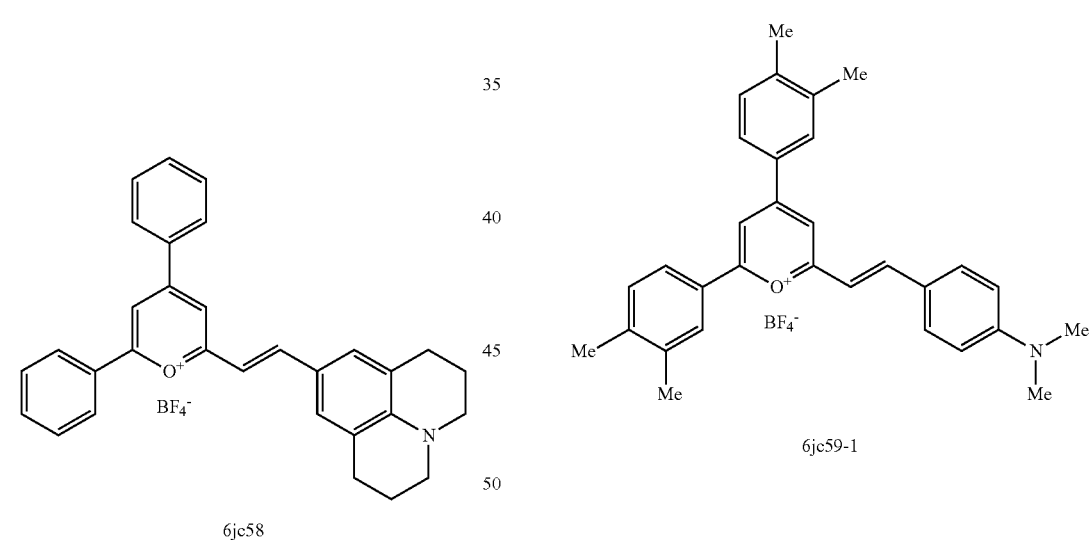

6jc58

6jc59-1

Pyrylium salt 6jc26 (120 mg, 0.37 mmol) and 9-CHO-julolidine (34 mg, 0.22 mmol) in MeOH (8 mL) was stirred at room temperature overnight. The solvent was removed and the residue suspended in ether and filtered to give solid. Recrystallization from EtOH gave purple solid of 96 mg.

δ$_H$(DMSO-d$_6$, 400 MHz) 8.44-8.14 (m, 7H, Ar, HC=), 7.75-7.60 (m, 6H, Ar), 7.47 (s, 2H, Ar), 7.22 (d, 1H, J=15.2, HC=), 3.50-3.40 (m, 4H, 2×CH$_2$), 2.78-2.70 (m, 4H, 2×CH$_2$), 2.01-1.85 (m, 4H, 2×CH$_2$).

Pyrylium salt 6jc57 (100 mg, 0.22 mmol) and p-dimethylamino benzaldehyde (34 mg, 0.22 mmol) in MeOH (8 mL) was stirred at room temperature overnight. The solvent was removed and the residue suspended in ether and filtered to give blue solid. Recrystallization from EtOH gave green solid of 79 mg.

δ$_H$(DMSO-d$_6$, 400 MHz) 8.53 (s, 1H, Ar), 8.41 (s, 1H, Ar), 8.36 (d, 1H, J=15.6, HC=), 8.26 (s, 1H, Ar), 8.23 (d, 1H, J=8.8, Ar), 8.16 (s, 1H, Ar), 8.12 (d, 1H, J=7.6, Ar 7.83 (d, 2H, J=8.8, Ar), 7.52-7.43 (m, 2H, Ar), 7.37 (d, 1H, J=15.6, HC=), 6.91 (d, 2H, J=8.8, Ar), 3.15 (s, 6H, NMe$_2$), 2.43 (s, 3H, Me), 2.42 (s, 3H, Me), 2.40 (s, 6H, 2×Me).

Example 4W: Compound 6jc59-2; 2-((1E,3E)-4-(4-(dimethylamino)phenyl)buta-1,3-dien-1-yl)-4,6-bis(3,4-dimethylphenyl)pyrylium boron tetrafluoride Salt

Example 4X: Compound 6jc59-3; (E)-2-(2-(1H-indol-3-yl)vinyl)-4,6-bis(3,4-dimethylphenyl)pyrylium boron tetrafluoride Salt

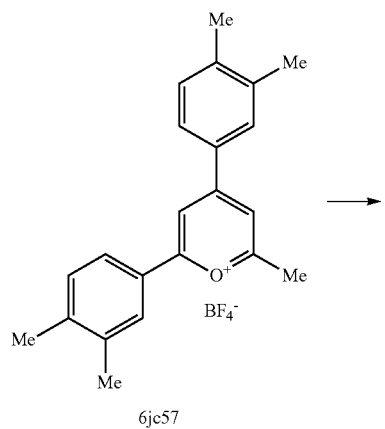

6jc57

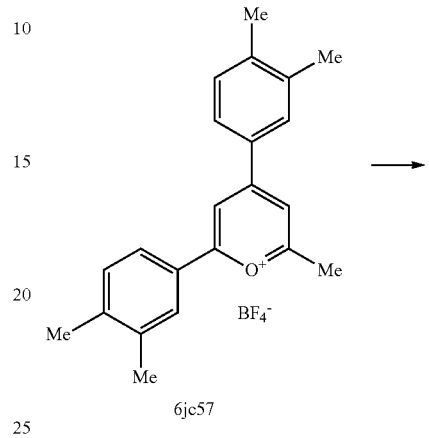

6jc57

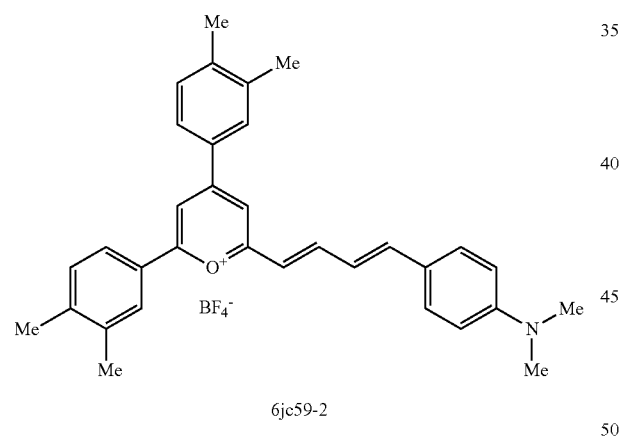

6jc59-2

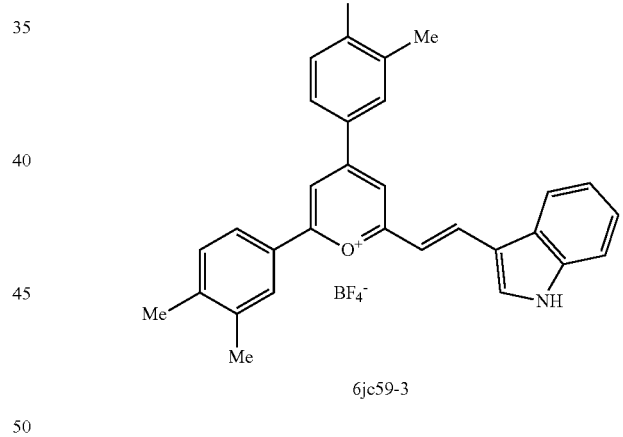

6jc59-3

Pyrylium salt 6jc57 (100 mg, 0.22 mmol) and p-dimethylamino cinnamaldehyde 39 mg, 0.22 mmol) in MeOH (8 mL) was stirred at room temperature overnight. The solvent was removed and the residue suspended in ether and filtered to give blue solid. Recrystallization from EtOH gave green solid of 70 mg.

$\delta_H$(DMSO-$d_6$, 400 MHz) 8.58 (s, 1H, Ar), 8.42 (s, 1H, Ar), 8.30-8.16 (m, 4H, Ar, HC=), 8.14 (d, 1H, J=8.0, Ar), 7.62 (d, 2H, J=8.4, Ar), 7.53-7.46 (m, 3H, Ar, HC=), 7.25 (t, 1H, J=14.0, HC=), 6.90-6.77 (m, 3H, Ar, HC=), 3.07 (s, 6H, NMe$_2$), 2.44 (s, 3H, Me), 2.41 (s, 3H, Me), 2.40 (s, 6H, 2×Me).

Pyrylium salt 6jc57 (100 mg, 0.22 mmol) and indole-3-carboxaldehyde (32 mg, 0.22 mmol) in MeOH (8 mL) was stirred at room temperature for 2 days. The solvent was removed and the residue was suspended in ether and filtered to give blue solid. Recrystallization from EtOH gave green solid of 55 mg.

$\delta_H$(DMSO-$d_6$, 400 MHz) 12.54 (br s, 1H, NH), 8.64 (d, 1H, J=15.6, HC=), 8.55 (s, 1H, Ar), 8.52 (s, 1H, Ar), 8.43 (s, 1H, Ar), 8.32-8.22 (m, 3H, Ar), 8.16 (s, 1H, Ar), 8.12 (d, 1H, J=8.4, Ar), 7.63-7.59 (m, 1H, Ar), 7.56-7.45 (m, 3H, Ar, HC=), 7.43-7.34 (m, 2H, Ar), 2.45 (s, 3H, Me), 2.43 (s, 3H, Me), 2.41 (s, 6H, 2×Me).

Example 4Y: Compound 6jc60-1; (E)-2,4-bis(4-(tert-butyl)phenyl)-6-(4-(dimethylamino)styryl)pyrylium boron tetrafluoride Salt Example 4Z: Compound 6jc60-2; 2,4-bis(4-(tert-butyl)phenyl)-6-((1E,3E)-4-(4-(dimethylamino)phenyl)buta-1,3-dien-1-yl)pyrylium boron tetrafluoride Salt

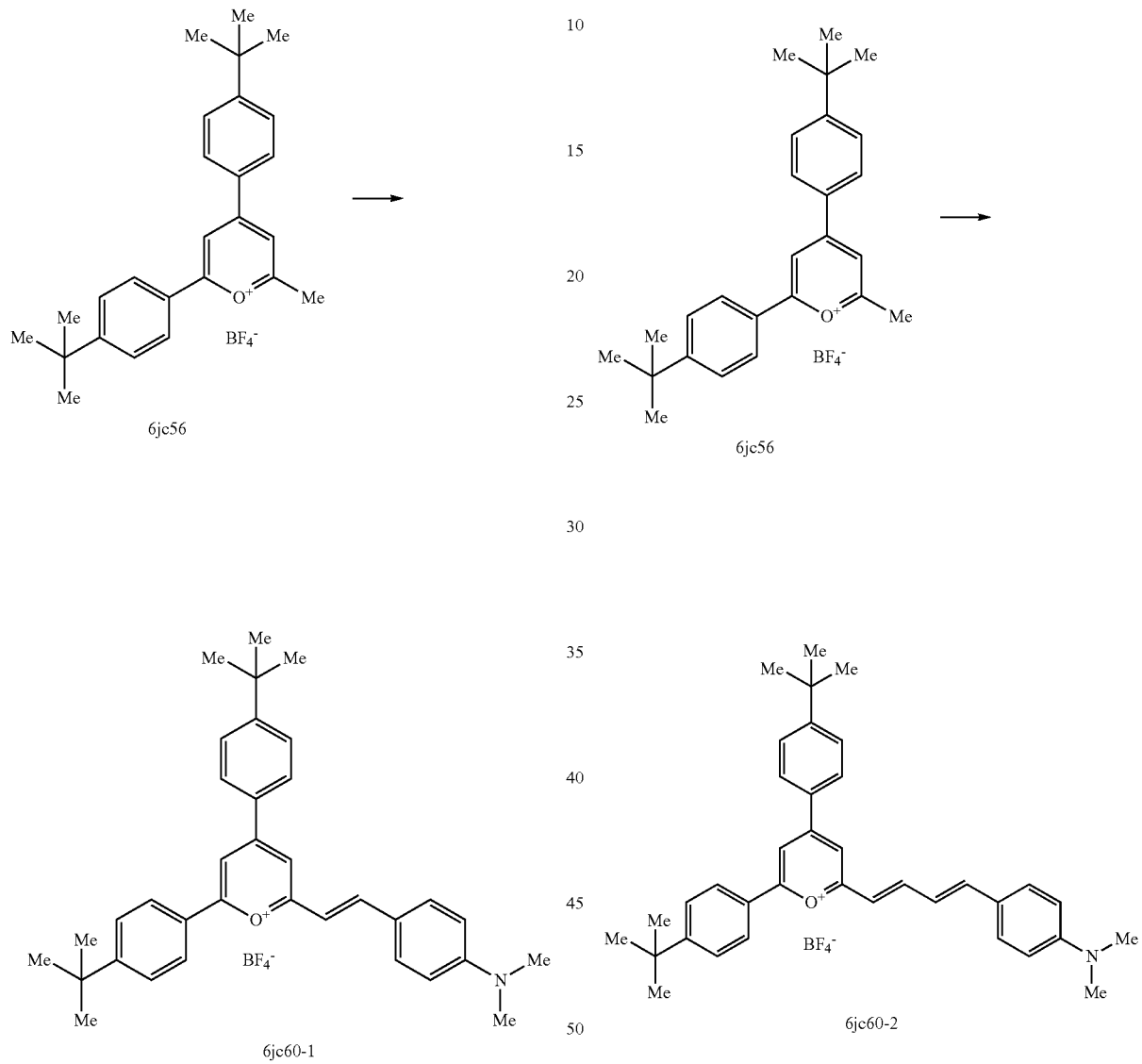

Pyrylium salt 6jc56 (100 mg, 0.22 mmol) and p-dimethylamino benzaldehyde (40 mg, 0.22 mmol) in MeOH (8 mL) were stirred at room temperature overnight. The solvent was removed and the residue suspended in ether and filtered to give solid. Recrystallization from EtOH gave green solid of 67 mg.

$\delta_H$(DMSO-d$_6$, 400 MHz) 8.56 (s, 1H, Ar), 8.41 (s, 1H, Ar), 8.40-8.33 (m, 3H, Ar, HC=), 8.26 (d, 2H, J=8.4, Ar), 7.83 (d, 2H, J=9.6, Ar), 7.78-7.71 (m, 4H, Ar), 7.37 (d, 1H, J=15.6, HC=), 6.91 (d, 2H, J=8.8, Ar), 3.15 (s, 6H, NMe$_2$), 1.39 (s, 9H, tBu), 1.38 (s, 9H, tBu).

Pyrylium salt 6jc56 (100 mg, 0.22 mmol) and p-dimethylamino cinnamaldehyde (44 mg, 0.22 mmol) in MeOH (8 mL) were stirred at room temperature overnight. The solvent was removed and the residue suspended in ether and filtered to give solid. Recrystallization from EtOH gave green solid of 50 mg.

$\delta_H$(DMSO-d$_6$, 400 MHz) 8.61 (s, 1H, Ar), 8.42-8.37 (m, 3H, Ar), 8.29 (d, 2H, J=8.8, Ar), 8.22 (t, 1H, J=14.8, HC=), 7.54 (d, 4H, J=8.0, Ar), 7.62 (d, 2H, J=9.2, Ar), 7.52 (d, 1H, J=14.8, HC=), 7.27 (t, 1H, J=15.2, HC=), 6.86 (d, 1H, J=15.2, HC=), 6.81 (d, 2H, J=8.8, Ar), 3.07 (s, 6H, NMe$_2$), 1.39 (s, 9H, tBu), 1.38 (s, 9H, tBu).

Example 4AA: Compound 6jc60-3; (E)-2-(2-(1H-indol-3-yl)vinyl)-4,6-bis(4-(tert-butyl)phenyl)pyrylium boron tetrafluoride Salt

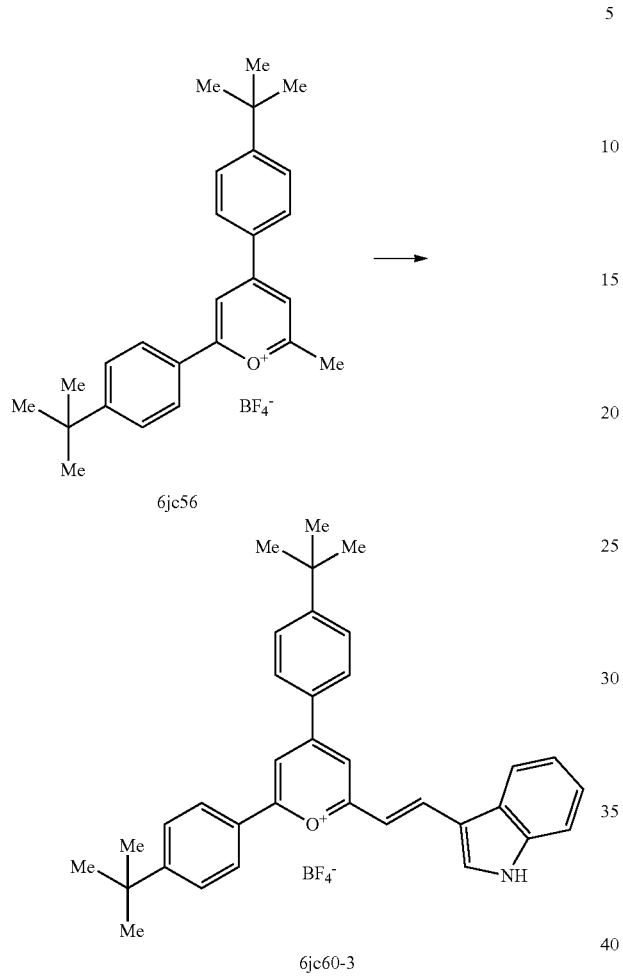

Pyrylium salt 6jc56 (100 mg, 0.22 mmol) and indole-3-carboxaldehyde (32 mg, 0.22 mmol) in MeOH (8 mL) were stirred at room temperature overnight. The solvent was removed and the residue suspended in ether and filtered to give solid. Recrystallization from EtOH gave green solid of 50 mg.

$\delta_H$(DMSO-d$_6$, 400 MHz) 12.56 (br s, 1H, NH), 8.67 (d, 1H, J=15.6, HC=), 8.58 (s, 1H, Ar), 8.52 (s, 1H, Ar), 8.46-8.40 (m, 3H, Ar), 8.32-8.24 (m, 3H, Ar), 7.80-7.72 (m, 4H, Ar), 7.66-7.59 (m, 1H, Ar), 7.51 (d, 1H, J=15.6, HC=), 7.43-7.35 (m, 2H, Ar), 1.39 (s, 18H, 2×tBu).

Example 4BB: Compound 6jc61; 2,4-bis(4-ethylphenyl)-6-methylpyrylium boron tetrafluoride Salt

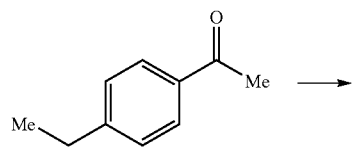

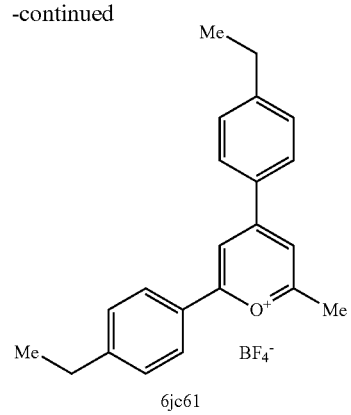

Boron trifluoride etherate (4.17 mL, 33.8 mmol) was added to p-ethyl-acetophenone (2.00 g, 13.51 mmol) and acetic anhydride (1.28 mL, 13.51 mmol) at room temperature. The reaction was heated to 135° C. for 3 hours, cooled, poured into EtOAc and the yellow solid filtered to give 214 mg solid product.

$\delta_H$(MeOH-d$_4$, 400 MHz) 8.85 (s, 1H, Ar), 8.35-8.30 (m, 3H, Ar), 8.24 (d, 2H, J=8.4, Ar), 7.57 (d, 4H, J=8.0, Ar), 2.99 (s, 3H, Me), 2.81 (q, 4H, J=8.0, 2×CH$_2$), 1.30 (t, 6H, J=8.0, 2×CH$_3$).

Example 4CC: Compound 6jc64-1

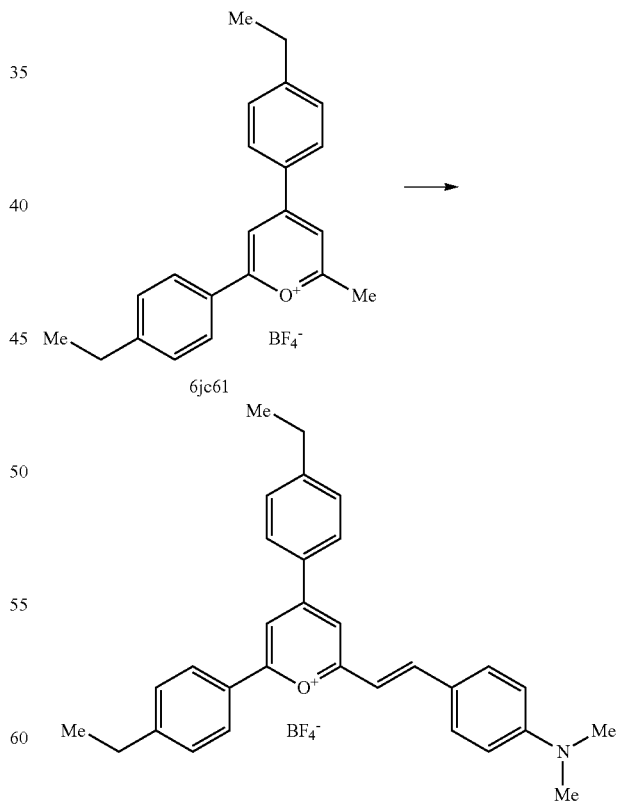

Pyrylium salt 6jc61 (50 mg, 0.13 mmol) and p-dimethylamino benzaldehyde (20 mg, 0.13 mmol) in MeOH (8 mL)

were stirred at room temperature overnight. The solvent was removed and the residue suspended in ether and filtered to give blue solid. Recrystallization from EtOH gave brown solid of 41 mg.

$\delta_H$(DMSO-d$_6$, 400 MHz) 8.56 (s, 1H, Ar), 8.46-8.33 (m, 4H, Ar, HC═), 8.29 (d, 2H, J=8.0, Ar), 7.84 (d, 2H, J=8.4, Ar), 7.62-7.54 (m, 4H, Ar), 7.38 (d, 1H, J=16.4, HC═), 6.92 (d, 2H, J=8.4, Ar), 3.15 (s, 6H, NMe$_2$), 2.79 (q, 4H, J=7.2, 2×CH$_2$), 1.28 (t, 6H, J=7.2, 2×CH$_3$).

Example 4DD: Compound 6jc64-2; 2-((1E,3E)-4-(4-(dimethylamino)phenyl)buta-1,3-dien-1-yl)-4,6-bis(4-ethylphenyl)pyrylium boron tetrafluoride Salt

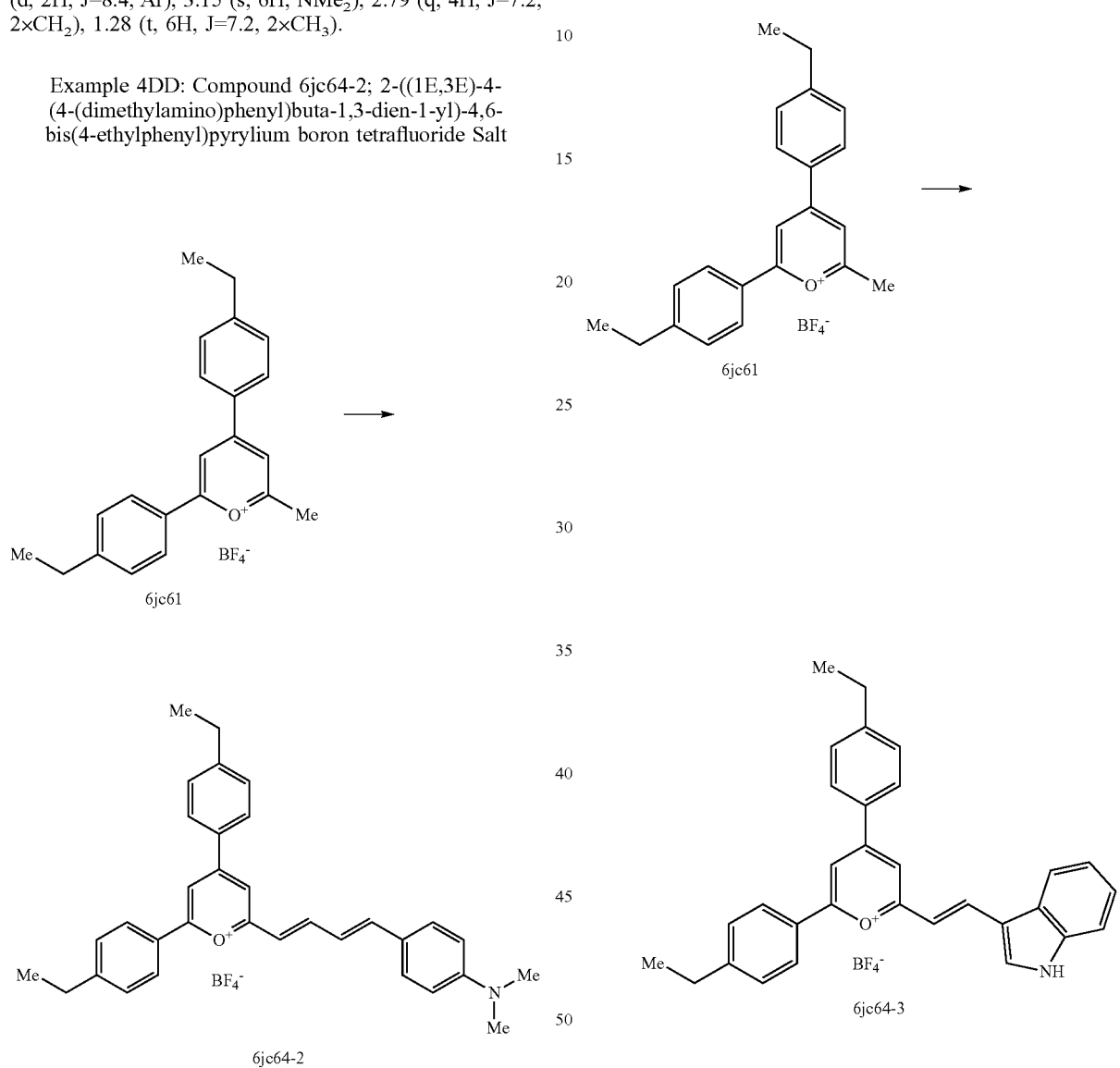

Example 4EE: Compound 6jc64-3; (E)-2-(2-(1H-indol-3-yl)vinyl)-4,6-bis(4-ethylphenyl)pyrylium boron tetrafluoride Salt

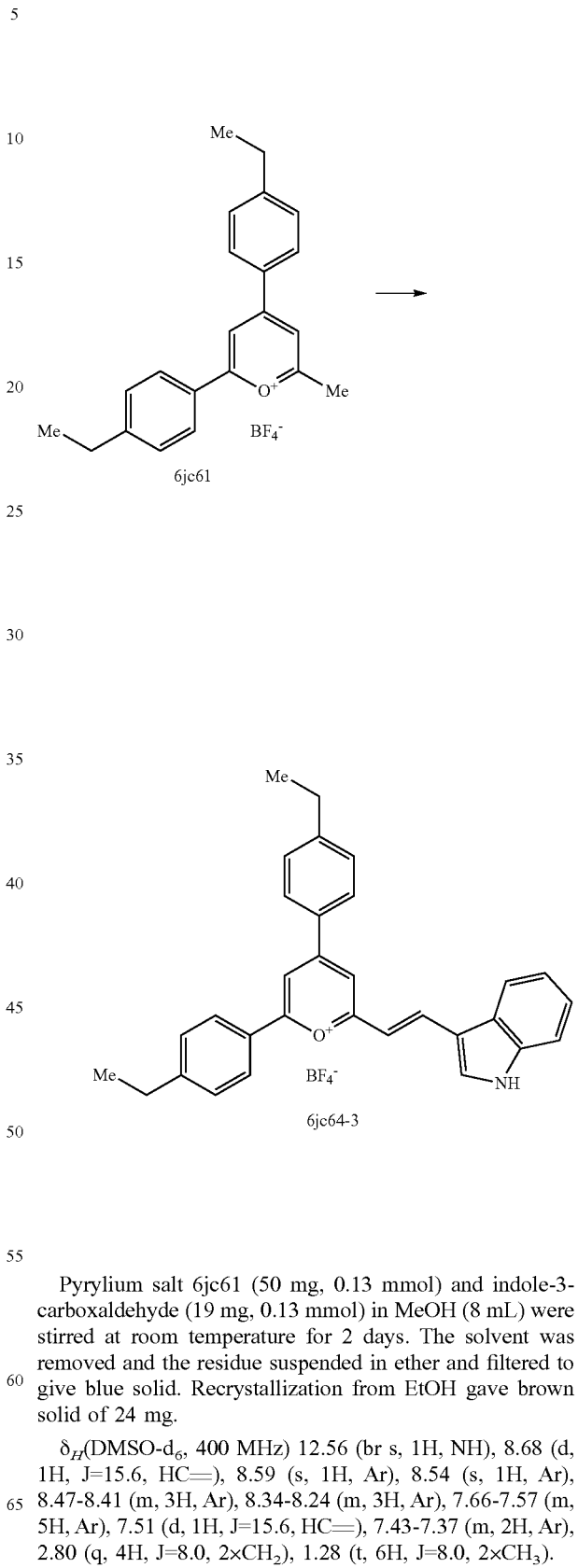

Pyrylium salt 6jc61 (50 mg, 0.13 mmol) and p-dimethylamino cinnamaldehyde (23 mg, 0.13 mmol) in MeOH (8 mL) were stirred at room temperature overnight. The solvent was removed and the residue suspended in ether and filtered to give blue solid. Recrystallization from EtOH gave brown solid of 31 mg.

$\delta_H$(DMSO-d$_6$, 400 MHz) 8.63 (s, 1H, Ar), 8.43 (s, 1H, Ar), 8.40 (d, 2H, J=7.6, Ar), 8.32 (d, 2H, J=7.6, Ar), 8.24 (t, 1H, J=14.0, HC═), 7.67-7.56 (m, 6H, Ar), 7.52 (d, 1H, J=14.8, HC═), 7.27 (t, 1H, J=14.8, HC═), 6.86 (d, 1H, J=16.0, HC═), 6.81 (d, 2H, J=8.8, Ar), 3.08 (s, 6H, NMe$_2$), 2.79 (q, 4H, J=7.2, 2×CH$_2$), 1.27 (t, 6H, J=7.2, 2×CH$_3$).

Pyrylium salt 6jc61 (50 mg, 0.13 mmol) and indole-3-carboxaldehyde (19 mg, 0.13 mmol) in MeOH (8 mL) were stirred at room temperature for 2 days. The solvent was removed and the residue suspended in ether and filtered to give blue solid. Recrystallization from EtOH gave brown solid of 24 mg.

$\delta_H$(DMSO-d$_6$, 400 MHz) 12.56 (br s, 1H, NH), 8.68 (d, 1H, J=15.6, HC═), 8.59 (s, 1H, Ar), 8.54 (s, 1H, Ar), 8.47-8.41 (m, 3H, Ar), 8.34-8.24 (m, 3H, Ar), 7.66-7.57 (m, 5H, Ar), 7.51 (d, 1H, J=15.6, HC═), 7.43-7.37 (m, 2H, Ar), 2.80 (q, 4H, J=8.0, 2×CH$_2$), 1.28 (t, 6H, J=8.0, 2×CH$_3$).

Example 4FF: Compound 6jc65-1; (E)-2-(2-(1,2,3,5,6,7-hexahydropyrido[3,2,1-ij]quinolin-9-yl)vinyl)-4,6-di-p-tolylpyrylium boron tetrafluoride Salt Example 4GG: Compound 6jc65-2; (E)-2-(2-(1-methyl-1H-indol-3-yl)vinyl)-4,6-di-p-tolylpyrylium boron tetrafluoride Salt

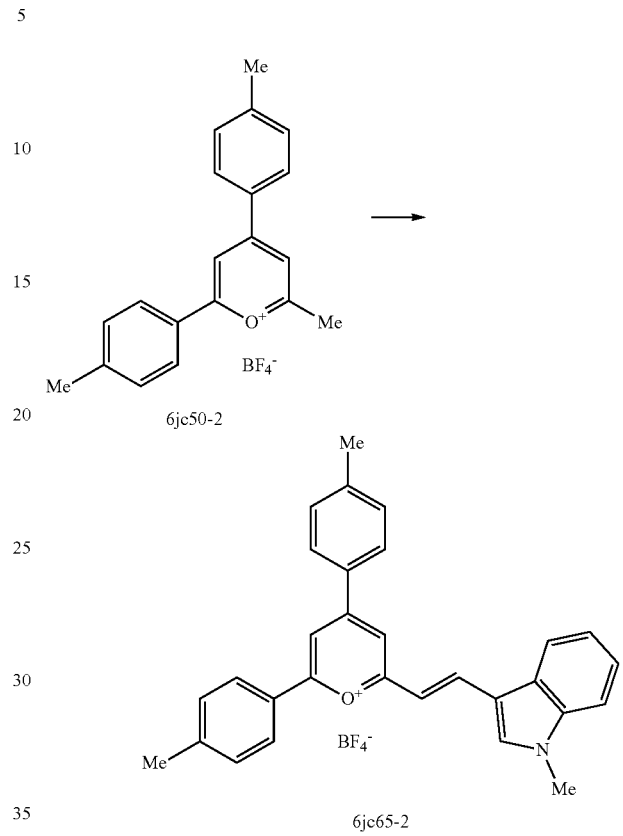

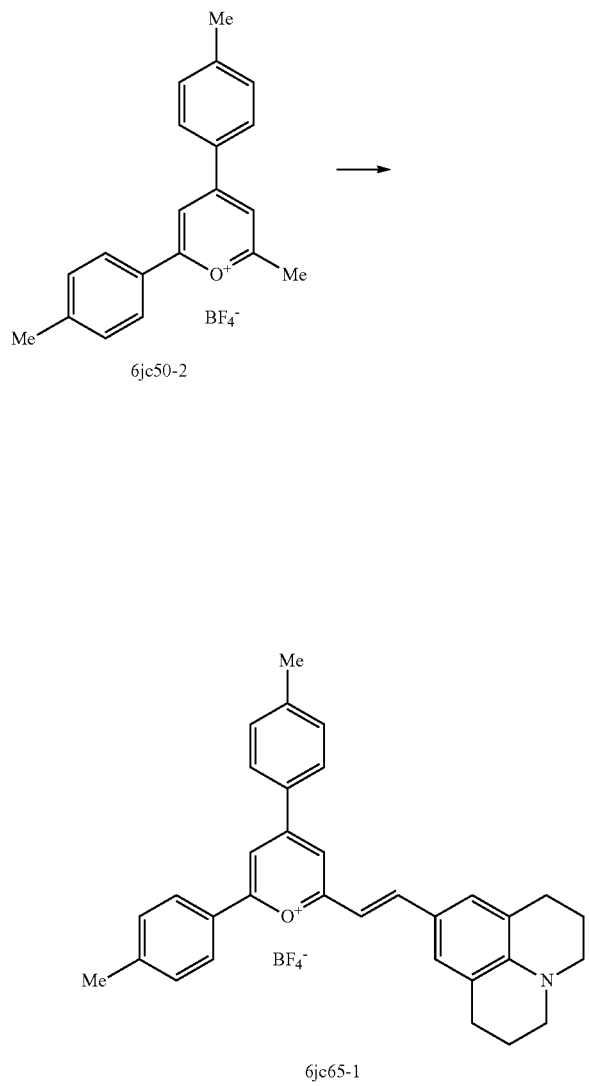

Pyrylium salt 6jc50-2 (50 mg, 0.14 mmol) and N-methyl-indole-3-carboxaldehyde (23 mg, 0.14 mmol) in MeOH (8 mL) was stirred at room temperature for 2 days. The solvent was removed and the residue suspended in ether and filtered to give blue solid. Recrystallization from EtOH gave purple solid of 40 mg.

$\delta_H$(DMSO-$d_6$, 400 MHz) 8.64 (d, 1H, J=15.6, HC=), 8.57 (s, 1H, Ar), 8.53 (s, 1H, Ar), 8.45-8.37 (m, 3H, Ar), 8.32-8.23 (m, 3H, Ar), 7.70 (d, 1H, J=6.8, Ar), 7.56 (t, 4H, J=6.8, Ar), (m, 5H, Ar), 7.50-7.40 (m, 3H, Ar, HC=), 3.97 (s, 3H, NMe), 2.50 (s, 6H, 2×CH$_3$).

Example 4HH: Compound 6jc66-1; (E)-2-(2-(1-methyl-1H-indol-3-yl)vinyl)-4,6-diphenylpyrylium boron tetrafluoride Salt Pyrylium salt 6jc50-2 (50 mg, 0.14 mmol) and 9-CHO-julolidine (28 mg, 0.14 mmol) in MeOH (8 mL) were stirred at room temperature overnight. The solvent was removed and the residue suspended in ether and filtered to give solid. Recrystallization from EtOH gave red solid of 48 mg.

$\delta_H$(DMSO-$d_6$, 400 MHz) 8.37-8.27 (m, 3H, Ar, HC=), 8.21-8.15 (m, 4H, Ar), 7.54-7.46 (m, 4H, Ar), 7.41 (s, 2H, Ar), 7.17 (d, 1H, J=15.6, HC=), 3.43-3.3.38 (m, 4H, 2×CH$_2$), 2.79-2.70 (m, 4H, 2×CH$_2$), 1.96-1.86 (m, 4H, 2×CH$_2$).

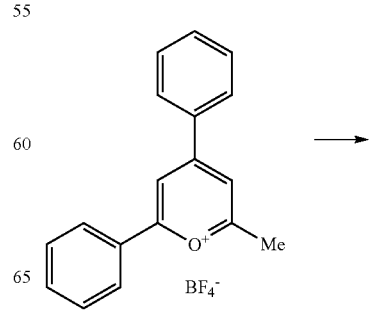

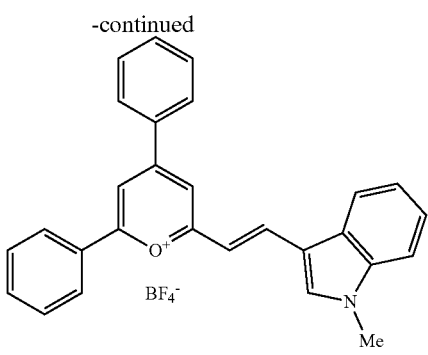

6jc66-1

Pyrylium salt 6jc26 (53 mg, 0.16 mmol) and N-methyl-indole-3-carboxaldehyde (25 mg, 0.16 mmol) in MeOH (8 mL) were stirred at room temperature for 2 days. The solvent was removed and the residue suspended in ether and filtered to give blue solid. Recrystallization from EtOH gave purple solid of 34 mg.

$\delta_H$(DMSO-$d_6$, 400 MHz) 8.72 (d, 1H, J=15.6, HC=), 8.63 (s, 1H, Ar), 8.59 (s, 1H, Ar), 8.53 (d, 2H, J=7.6, Ar), 8.45 (s, 1H, Ar), 8.38-8.29 (m, 3H, Ar), 7.84-7.70 (m, 7H, Ar), 7.52 (d, 1H, J=15.6, HC=), 7.49-7.43 (m, 2H, Ar), 3.99 (s, 3H, NMe).

Example 4II: Compound 6jc66-2; (E)-2,4-bis(4-ethylphenyl)-6-(2-(1-methyl-1H-indol-3-yl)vinyl) pyrylium boron tetrafluoride Salt

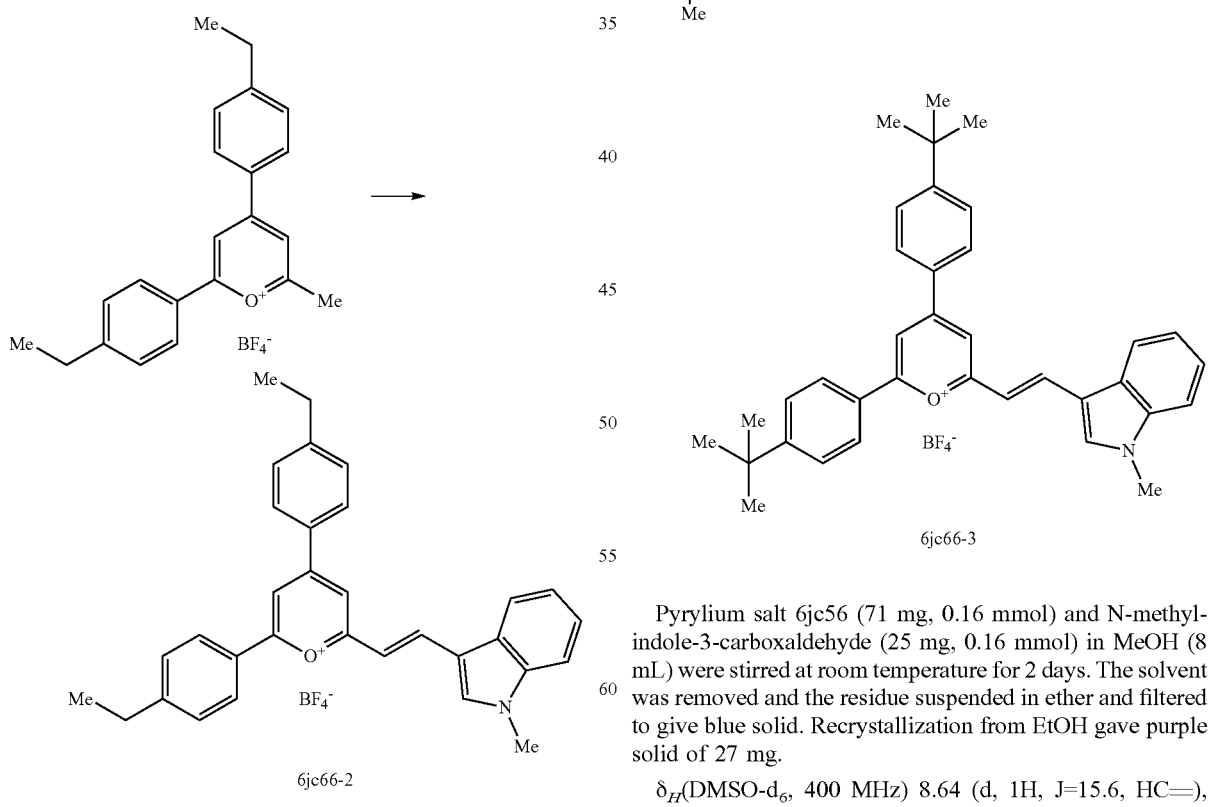

6jc66-2

Pyrylium salt 6jc61 (62 mg, 0.16 mmol) and N-methyl-indole-3-carboxaldehyde (25 mg, 0.16 mmol) in MeOH (8 mL) were stirred at room temperature for 2 days. The solvent was removed and the residue was suspended in ether and filtered to give blue solid. Recrystallization from EtOH gave purple solid of 13 mg.

$\delta_H$(DMSO-$d_6$, 400 MHz) 8.65 (d, 1H, J=15.6, HC=), 8.59 (s, 1H, Ar), 8.54 (s, 1H, Ar), 8.45 (d, 2H, J=7.6, Ar), 8.41 (s, 1H, Ar), 8.34-8.26 (m, 3H, Ar), 7.74-7.68 (m, 1H, Ar), 7.64-7.56 (m, 4H, Ar), 7.52-7.42 (m, 3H, Ar), 3.98 (s, 3H, NMe), 3.00-2.75 (m, 4H, 2×CH$_2$), 1.29 (t, 6H, J=7.2, 2×CH$_3$).

Example 4JJ: Compound 6jc66-3; (E)-2,4-bis(4-(tert-butyl)phenyl)-6-(2-(1-methyl-1H-indol-3-yl) vinyl)pyrylium boron tetrafluoride Salt 6jc66-3

Pyrylium salt 6jc56 (71 mg, 0.16 mmol) and N-methyl-indole-3-carboxaldehyde (25 mg, 0.16 mmol) in MeOH (8 mL) were stirred at room temperature for 2 days. The solvent was removed and the residue suspended in ether and filtered to give blue solid. Recrystallization from EtOH gave purple solid of 27 mg.

$\delta_H$(DMSO-$d_6$, 400 MHz) 8.64 (d, 1H, J=15.6, HC=), 8.58 (s, 1H, Ar), 8.52 (s, 1H, Ar), 8.47-8.40 (m, 3H, Ar), 8.32-8.24 (m, 3H, Ar), 7.81-7.68 (m, 5H, Ar), 7.53-7.42 (m, 3H, Ar, HC=), 3.99 (s, 3H, NMe), 1.40 (s, 18H, 6×CH$_3$).

Example 4KK: Compound 6jc66-4; (E)-2,4-bis(3,4-dimethylphenyl)-6-(2-(1-methyl-1H-indol-3-yl)vinyl)pyrylium boron tetrafluoride Salt

Example 4LL: Compound 6jc67; 2,4-diphenyl-6-((1E,3E)-3-(1,3,3-trimethylindolin-2-ylidene)prop-1-en-1-yl)pyrylium boron tetrafluoride Salt Pyrylium salt 6jc26 (50 mg, 0.14 mmol) and 2-(1,3,3-Trimethylindolin-2-ylidene)acetaldehyde

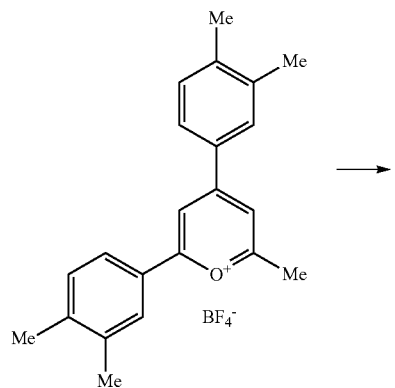

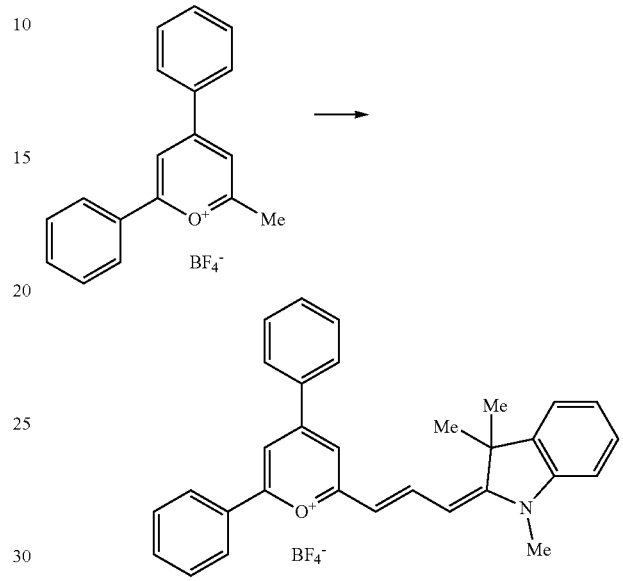

6jc67

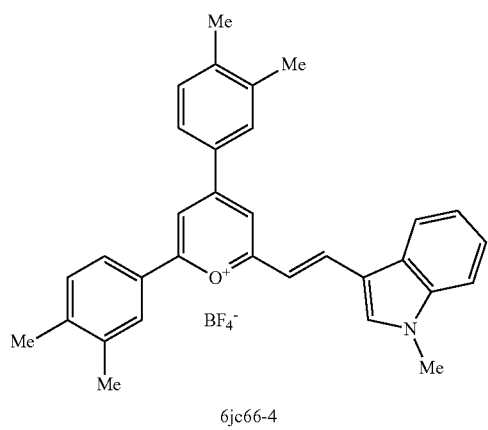

6jc66-4

(28 mg, 0.14 mmol) in acetic anhydride (2 mL) were stirred at reflux for 1 hour. The reaction was cooled and co-evaporated with toluene (×3), washed with ether and decanted (×2). The residue was purified by column chromatography DCM/MeOH and transferred to a vial to give a blue solid 69 mg.

$\delta_H$(DMSO-$d_6$, 400 MHz) 8.47 (t, 1H, J=13.2, HC=), 8.26-8.10 (m, 4H, Ar), 7.95 (s, 1H, Ar), 7.90-7.59 (m, 8H, Ar), 7.53-7.44 (m, 2H, Ar), 7.35 (t, 1H, J=7.6, Ar), 6.58 (d, 1H, J=13.2, HC=), 6.39 (br s, 1H, HC=), 3.73 (s, 3H, NMe), 1.74 (s, 6H, 2×CH$_3$).

Example 4MM: Compound 6jc67-A; 2,4-di-p-tolyl-6-((1E,3E)-3-(1,3,3-trimethylindolin-2-ylidene)prop-1-en-1-yl)pyrylium boron tetrafluoride Salt Pyrylium salt 6jc57 (67 mg, 0.16 mmol) and N-methylindole-3-carboxaldehyde (25 mg, 0.16 mmol) in MeOH (8 mL) were stirred at room temperature for 2 days. The solvent was removed and the residue suspended in ether and filtered to give blue solid. Recrystallization from EtOH gave green solid of 38 mg.

$\delta_H$(DMSO-$d_6$, 400 MHz) 8.61 (d, 1H, J=16.0, HC=), 8.54 (s, 1H, Ar), 8.51 (s, 1H, Ar), 8.40 (s, 1H, Ar), 8.34-8.8.22 (m, 3H, Ar), 8.19-8.8.06 (m, 2H, Ar), 7.70 (d, 1H, J=6.8, Ar), 7.58-7.40 (m, 5H, Ar, HC=), 3.97 (s, 3H, NMe), 2.45 (s, 3H, CH$_3$), 2.43 (s, 3H, CH$_3$), 2.41 (s, 6H, 2×CH$_3$).

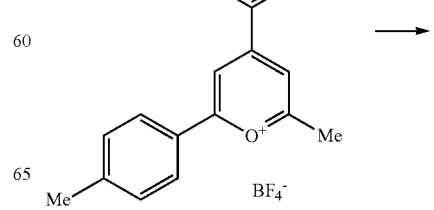

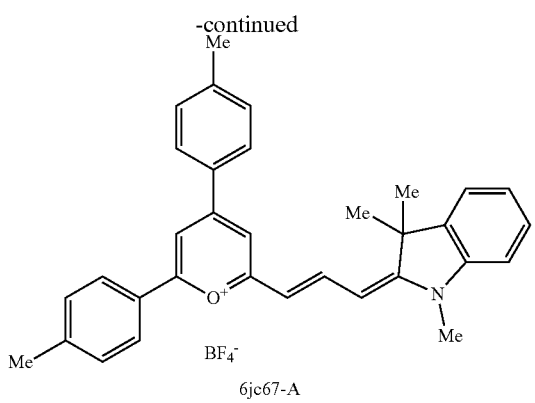

6jc67-A

Pyrylium salt 6jc50-2 (50 mg, 0.14 mmol) and 2-(1,3,3-Trimethylindolin-2-ylidene)acetaldehyde (28 mg, 0.14 mmol) in acetic anhydride (2 mL) were stirred at reflux for 30 minutes. The reaction was cooled and co-evaporated with toluene (×3), washed with ether and decanted (×2). The blue solid was transferred to a vial to give 71 mg.

$\delta_H$(DMSO-d$_6$, 400 MHz) 8.41 (t, 1H, J=14.0, HC=), 8.09 (d, 1H, J=8.0, Ar), 8.05 (d, 1H, J=8.0, Ar), 7.91 (s, 1H, Ar), 7.88-7.72 (m, 1H, Ar), 7.62 (d, 1H, J=8.0, Ar), 7.51-7.37 (m, 6H, Ar), 7.30-7.24 (m, 1H, Ar), 6.45 (d, 1H, J=14.0, HC=), 6.35 (br s, 1H, HC=), 3.65 (s, 3H, NMe), 2.43 (s, 3H, ArCH$_3$), 2.40 (s, 3H, ArCH$_3$), 1.69 (s, 6H, 2×CH$_3$).

Example 4NN: Compound 6jc68-1; (E)-2,4-bis(4-chlorophenyl)-6-(2-(1-methyl-1H-indol-3-yl)vinyl) pyrylium boron tetrafluoride Salt

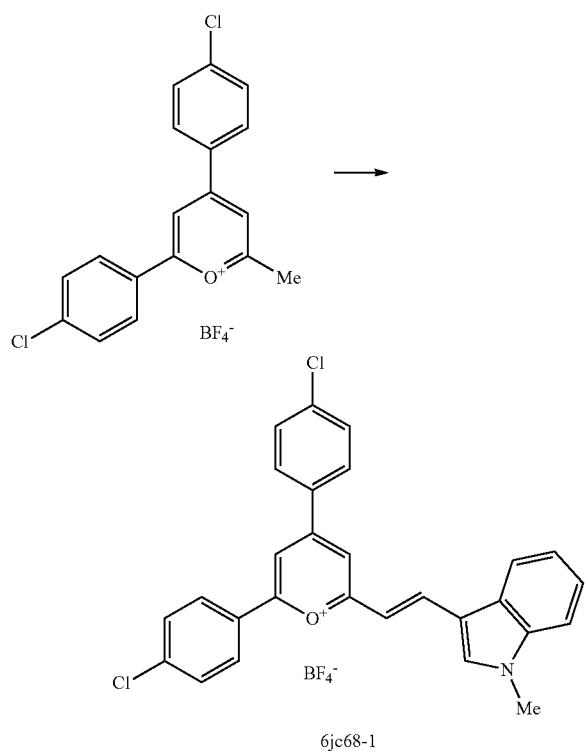

6jc68-1

Pyrylium salt 6jc32-1 (52 mg, 0.14 mmol) and N-methyl-indole-3-carboxaldehyde (23 mg, 0.14 mmol) in MeOH (8 mL) were stirred at room temperature for 2 days. The solvent was removed and the residue was suspended in ether and filtered to give blue solid. Recrystallization from EtOH gave purple solid of 27 mg.

$\delta_H$(DMSO-d$_6$, 400 MHz) 8.75 (d, 1H, J=16.0, HC=), 8.63 (s, 1H, Ar), 8.60 (s, 1H, Ar), 8.54 (d, 2H, J=8.4, Ar), 8.45 (s, 1H, Ar), 8.40-8.28 (m, 3H, Ar), 7.88-7.80 (m, 4H, Ar), 7.76-7.01 (m, 1H, Ar), 7.55-7.43 (m, 3H, Ar, HC=), 4.00 (s, 3H, NMe).

Example 4OO: Compound 6jc68-2; (E)-2,4-bis(4-bromophenyl)-6-(2-(1-methyl-1H-indol-3-yl)vinyl) pyrylium boron tetrafluoride Salt

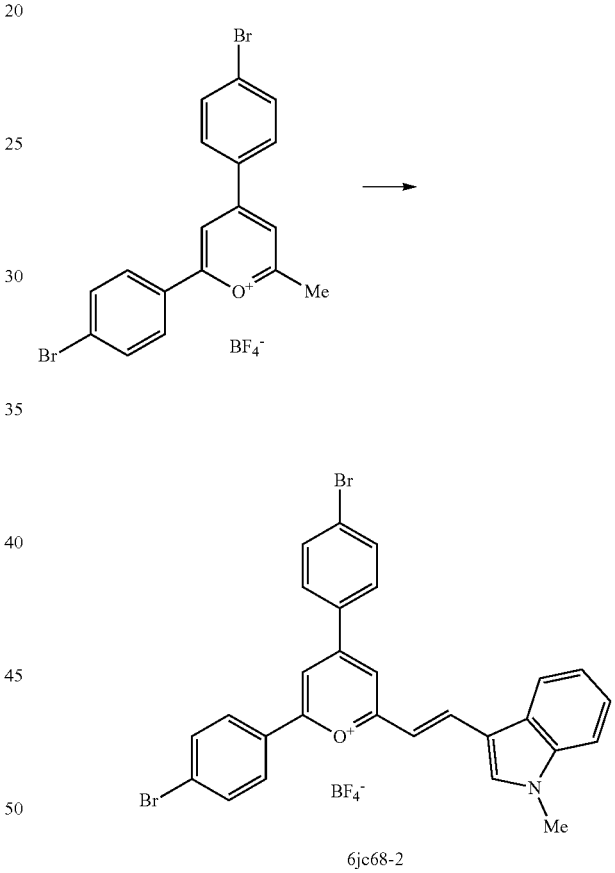

6jc68-2

Pyrylium salt 6jc47 (63 mg, 0.14 mmol) and N-methyl-indole-3-carboxaldehyde (23 mg, 0.14 mmol) in MeOH (8 mL) were stirred at room temperature for 2 days. The solvent was removed and the residue suspended in ether and filtered to give blue solid. Recrystallization from EtOH gave purple solid of 20 mg.

$\delta_H$(DMSO-d$_6$, 400 MHz) 8.74 (d, 1H, J=16.0, HC=), 8.62 (s, 1H, Ar), 8.61 (s, 1H, Ar), 8.48-8.42 (m, 3H, Ar), 8.32-8.23 (m, 3H, Ar), 8.06-7.92 (m, 4H, Ar), 7.76-7.00 (m, 1H, Ar), 7.54-7.42 (m, 3H, Ar, HC=), 4.00 (s, 3H, NMe).

Example 4PP: Compound 6jc69-1; (E)-2,4-bis(4-ethylphenyl)-6-(2-(1,2,3,5,6,7-hexahydropyrido[3,2,1-ij]quinolin-9-yl)vinyl)pyrylium boron tetrafluoride Salt Example 4QQ: Compound 6jc69-2; (E)-2,4-bis(4-(tert-butyl)phenyl)-6-(2-(1,2,3,5,6,7-hexahydropyrido[3,2,1-ij]quinolin-9-yl)vinyl)pyrylium boron tetrafluoride Salt

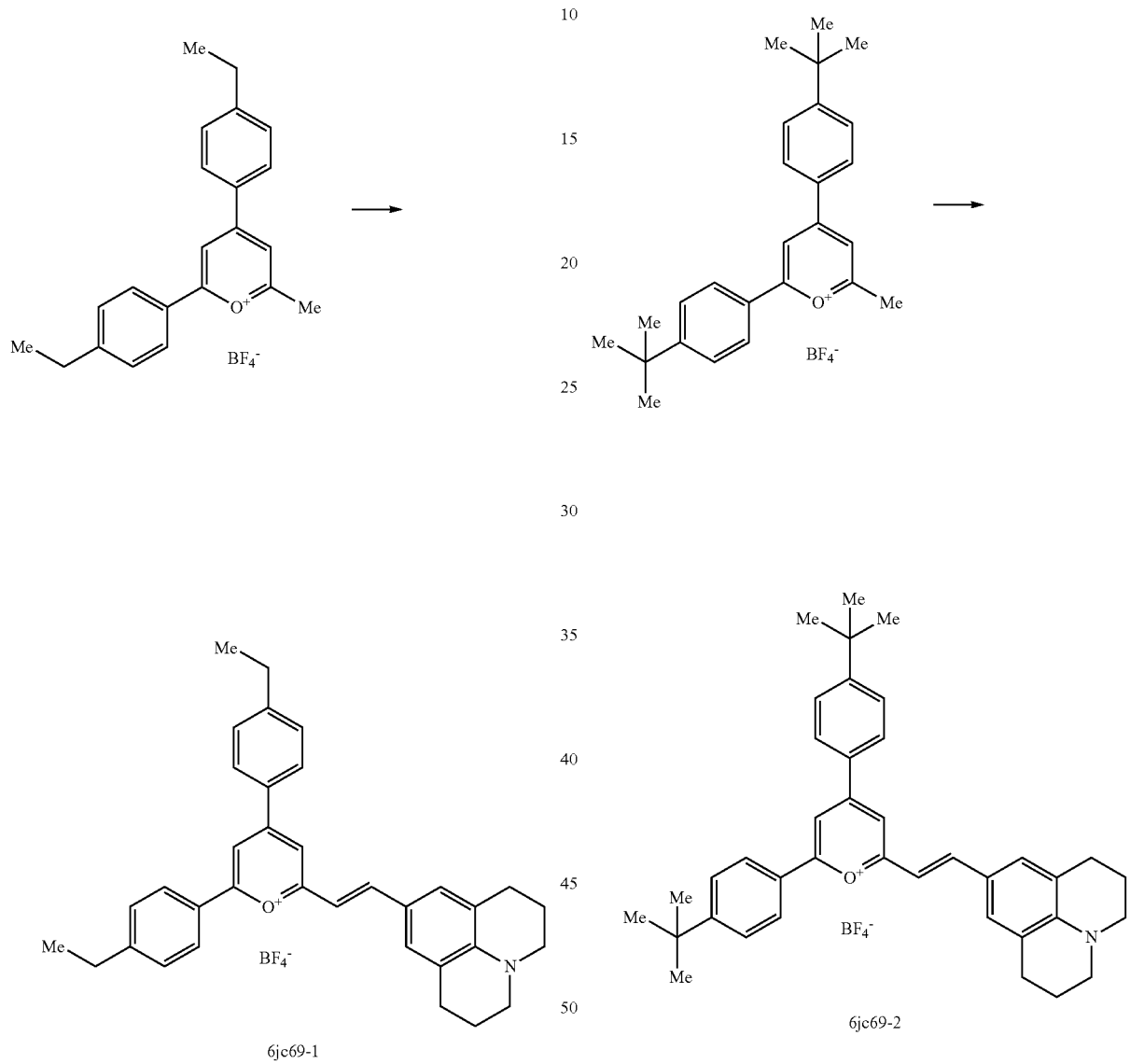

6jc69-1

6jc69-2

Pyrylium salt 6jc61 (46 mg, 0.12 mmol) and 9-CHO-julolidine (25 mg, 0.12 mmol) in MeOH (8 mL) were stirred at room temperature overnight. The solvent was removed and the residue suspended in ether and filtered to give solid. Recrystallization from EtOH gave purple solid of 44 mg.

$\delta_H$(DMSO-$d_6$, 400 MHz) 8.40-8.32 (m, 3H, Ar, HC=), 8.27-8.18 (m, 4H, Ar), 7.60-7.52 (m, 4H, Ar), 7.45 (s, 2H, Ar), 7.21 (d, 1H, J=15.6, HC=), 3.50-3.40 (m, 4H, 2×CH$_2$), 2.83-2.70 (m, 8H, 4×CH$_2$), 1.99-1.87 (m, 4H, 2×CH$_2$), 1.27 (t, 6H, J=7.2, 2×CH$_3$).

Pyrylium salt 6jc56 (53 mg, 0.12 mmol) and 9-CHO-julolidine (25 mg, 0.12 mmol) in MeOH (8 mL) was stirred at room temperature overnight. The solvent was removed and the residue was suspended in ether and filtered to give solid. Recrystallization from EtOH gave purple solid of 74 mg.

$\delta_H$(DMSO-$d_6$, 400 MHz) 8.38-8.31 (m, 3H, Ar, HC=), 8.24-8.15 (m, 4H, Ar), 7.78-7.67 (m, 4H, Ar), 7.45 (s, 2H, Ar), 7.19 (d, 1H, J=15.6, HC=), 3.49-3.40 (m, 4H, 2×CH$_2$), 2.80-2.72 (m, 4H, 2×CH$_2$), 1.97-1.88 (m, 4H, 2×CH$_2$), 1.38 (s, 18H, 9×CH$_3$).

Example 4RR: Compound 6jc69-3; (E)-2,4-bis(3,4-dimethylphenyl)-6-(2-(1,2,3,5,6,7-hexahydropyrido[3,2,1-ij]quinolin-9-yl)vinyl)pyrylium boron tetrafluoride Salt Example 4SS: Compound 6jc69-4; (E)-2,4-bis(4-chlorophenyl)-6-(2-(1,2,3,5,6,7-hexahydropyrido[3,2,1-ij]quinolin-9-yl)vinyl)pyrylium boron tetrafluoride Salt

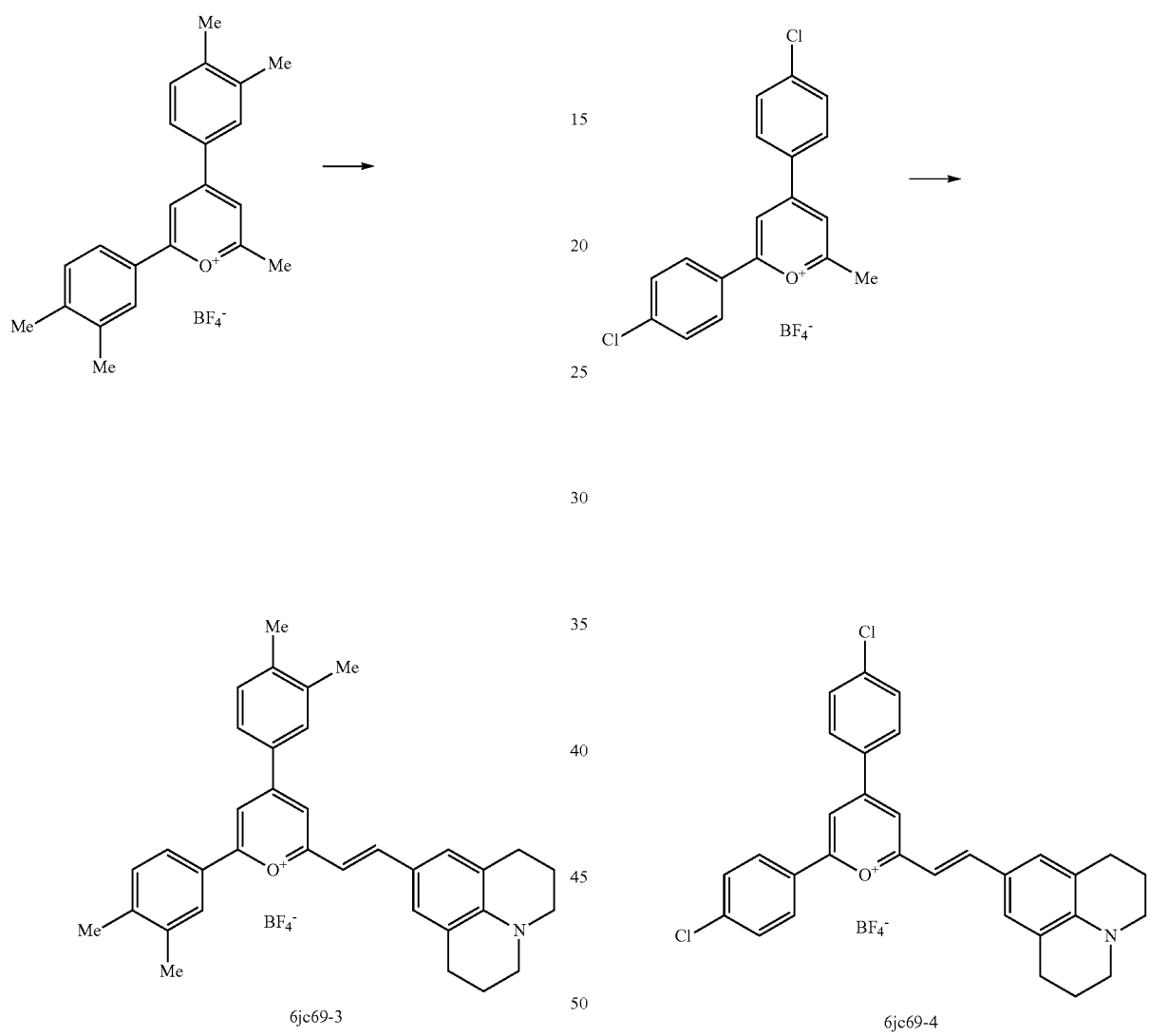

Pyrylium salt 6jc57 (50 mg, 0.12 mmol) and 9-CHO-julolidine (25 mg, 0.12 mmol) in MeOH (8 mL) were stirred at room temperature overnight. The solvent was removed and the residue were suspended in ether and filtered to give solid. Recrystallization from EtOH gave green solid of 64 mg.

$\delta_H$(DMSO-$d_6$, 400 MHz) 8.33 (s, 1H, Ar), 8.25-8.10 (m, 4H, Ar, HC=), 8.08 (s, 1H, Ar), 8.04 (d, 1H, J=7.6, Ar), 7.50-7.43 (m, 2H, Ar), 7.42 (s, 2H, Ar), 7.18 (d, 1H, J=16.0, HC=), 3.48-3.40 (m, 4H, 2×CH$_2$), 2.79-2.70 (m, 4H, 2×CH$_2$), 2.42 (s, 3H, CH$_3$), 2.40 (s, 3H, CH$_3$), 2.38 (s, 6H, 2×CH$_3$), 1.99-1.88 (m, 4H, 2×CH$_2$).

Pyrylium salt 6jc32-1 (48 mg, 0.12 mmol) and 9-CHO-julolidine (25 mg, 0.12 mmol) in MeOH (8 mL) were stirred at room temperature overnight. The solvent was removed and the residue suspended in ether and filtered to give solid. Recrystallization from EtOH gave purple solid of 39 mg.

$\delta_H$(DMSO-$d_6$, 400 MHz) 8.40 (d, 2H, J=8.4, Ar), 8.32 (s, 1H, Ar), 8.30-8.17 (m, 4H, Ar, HC=), 7.83-7.51 (m, 4H, Ar), 7.45 (s, 2H, Ar), 7.18 (d, 1H, J=15.2, HC=), 3.52-3.42 (m, 4H, 2×CH$_2$), 2.81-2.70 (m, 4H, 2×CH$_2$), 1.99-1.86 (m, 4H, 2×CH$_2$).

Example 4TT: Compound 6jc69-5; (E)-2,4-bis(4-bromophenyl)-6-(2-(1,2,3,5,6,7-hexahydropyrido[3,2,1-ij]quinolin-9-yl)vinyl)pyrylium boron tetrafluoride Salt

Example 4UU: Compound 6jc76-1; 2,4-bis(4-ethylphenyl)-6-((1E,3E)-3-(1,3,3-trimethylindolin-2-ylidene)prop-1-en-1-yl)pyrylium boron tetrafluoride Salt

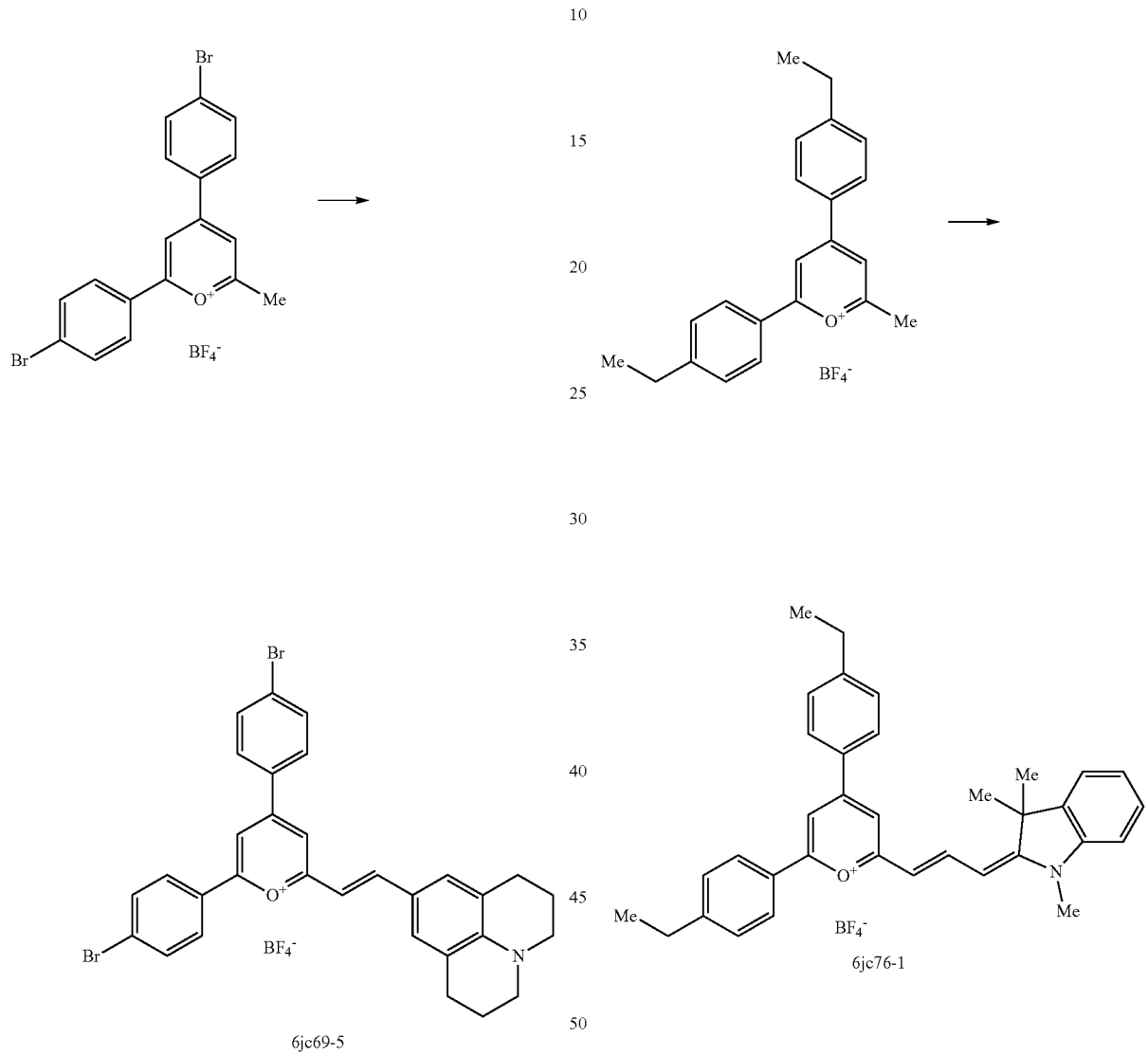

Pyrylium salt 6jc47 (59 mg, 0.12 mmol) and 9-CHO-julolidine (25 mg, 0.12 mmol) in MeOH (8 mL) were stirred at room temperature overnight. The solvent was removed and the residue was suspended in ether and filtered to give solid. Recrystallization from EtOH gave green solid of 47 mg.

$\delta_H$(DMSO-d$_6$, 400 MHz) 8.36-8.13 (m, 7H, Ar, HC=), 7.94-7.85 (m, 4H, Ar), 7.45 (s, 2H, Ar), 7.18 (d, 1H, J=14.8, HC=), 3.52-3.43 (m, 4H, 2×CH$_2$), 2.82-2.71 (m, 4H, 2×CH$_2$), 1.98-1.88 (m, 4H, 2×CH$_2$).

Pyrylium salt 6jc61 (50 mg, 0.13 mmol) and 2-(1,3,3-trimethylindolin-2-ylidene)acetealdehyde (26 mg, 013 mmol) in acetic anhydride (2 mL) was stirred at reflux for 30 minutes. The reaction was cooled and co-evaporated with toluene (×3), washed with ether and decanted (×2). The blue solid was transferred to a vial and lyophilized to give 90 mg.

$\delta_H$(DMSO-d$_6$, 400 MHz) 8.45 (t, 1H, J=14.0, HC=), 8.15 (d, 1H, J=8.0, Ar), 8.11 (d, 1H, J=8.0, Ar), 7.95 (s, 1H, Ar), 7.92-7.78 (m, 1H, Ar), 7.67 (d, 1H, J=6.8, Ar), 7.60-7.42 (m, 6H, Ar), 7.36-7.28 (m, 1H, Ar), 6.50 (d, 1H, J=14.0, HC=), 6.40 (br s, 1H, HC=), 3.69 (s, 3H, NMe), 2.81-2.69 (m, 4H, 2×CH$_2$), 2×CH$_2$), 1.74 (s, 6H, 2×CH$_3$), 1.32-1.20 (m, 6H, 2×CH$_3$).

Example 4VV: Compound 6jc76-2; 2,4-bis(4-tert-butyl)phenyl)-6-((1E,3E)-3-(1,3,3-trimethylindolin-2-ylidene)prop-1-en-1-yl)pyrylium boron tetrafluoride Salt

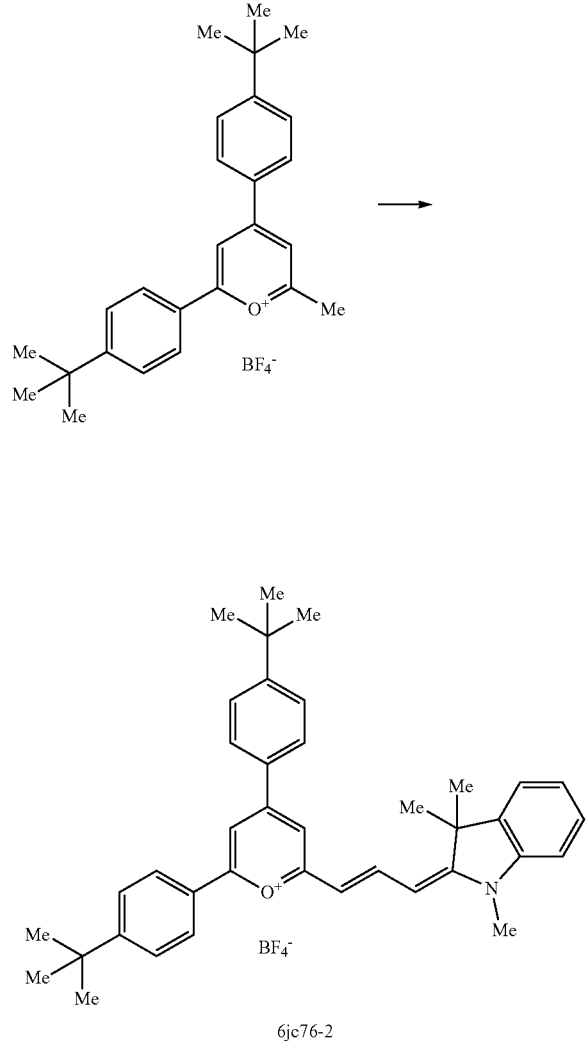

6jc76-2

Pyrylium salt 6jc56 (50 mg, 0.11 mmol) and 2-(1,2,3-trimethylindolin-2-ylidene)acetaldehyde (23 mg, 0.11 mmol) in acetic anhydride (2 mL) were stirred at reflux for 30 minutes. The reaction was cooled and co-evaporated with toluene (×3), washed with ether and decanted (×2). The resulting blue solid was transferred to a vial and lyophilized to give 78 mg.

$\delta_H$(DMSO-d$_6$, 400 MHz) 8.45 (t, 1H, J=13.2, HC=), 8.14 (d, 1H, J=8.0, Ar), 8.09 (d, 1H, J=8.0, Ar), 7.93 (s, 1H, Ar), 7.90-7.78 (m, 1H, Ar), 7.76-7.62 (m, 5H, Ar), 7.54-7.40 (m, 2H, Ar), 7.38-7.29 (m, 1H, Ar), 6.51 (d, 1H, J=13.2, HC=), 6.42 (br s, 1H, HC=), 3.70 (s, 3H, NMe), 1.74 (s, 6H, 2×CH$_3$), 1.38 (s, 9H, 3×CH$_3$), 1.36 (s, 9H, 3×CH$_3$).

Example 4WW: Compound 6jc77-1; 2,4-bis(4-chlorophenyl)-6-((1E,3E)-3-(1,3,3-trimethylindolin-2-ylidene)prop-1-en-1-yl)pyrylium boron tetrafluoride Salt

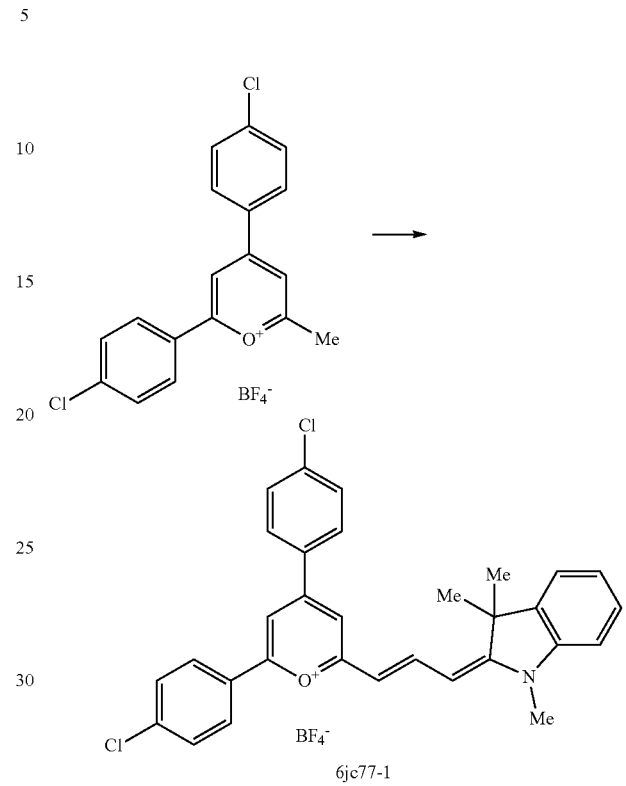

6jc77-1

Pyrylium salt 6jc32-1 (50 mg, 0.12 mmol) and 2-(1,3,3-trimethylindolin-2-ylidene)acetaldehyde (25 mg, 0.12 mmol) in acetic acid (2 mL) were stirred at reflux for 30 minutes. The reaction was cooled and co-evaporated with toluene (×3), washed with ether and decanted (×2). The blue solid was transferred to a vial and lyophilized to give 73 mg. 1H NMR shows desired product but spectrum not clean.

$\delta_H$(DMSO-d$_6$, 400 MHz) 8.44 (t, 1H, J=13.2, HC=), 8.27-8.10 (m, 4H, Ar), 7.92 (s, 1H, Ar), 7.88-7.64 (m, 6H, Ar), 7.60-7.32 (m, 3H, Ar), 6.72-6.55 (m, 2H, 2x HC=), 3.79 (s, 3H, NMe), 1.74 (s, 6H, 2×CH$_3$).

Example 4XX: Compound 6jc77-2; 2,4-bis(4-bromophenyl)-6-((1E,3E)-3-(1,3,3-trimethylindolin-2-ylidene)prop-1-en-1-yl)pyrylium boron tetrafluoride Salt

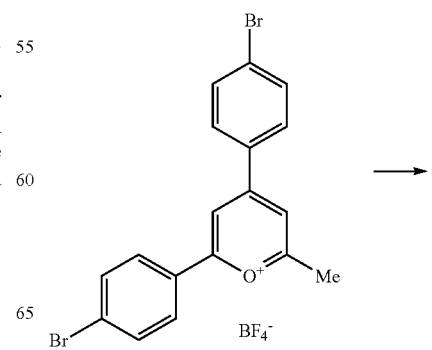

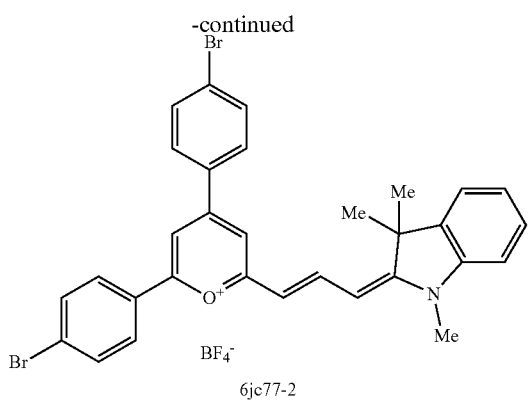

6jc77-2

Pyrylium salt (50 mg, 0.10 mmol) and 2-(1,3,3-trimethylindolin-2-ylidene)acetaldehyde (20 mg, 0.10 mmol) in acetic anhydride (2 mL) was stirred at reflux for 30 minutes. The reaction was cooled and co evaporated with toluene (×3), washed with ether and decanted (×2). The blue solid was transferred to a vial and lyophilized to give 71 mg. 1H NMR shows desired product but spectrum not entirely clean.

$\delta_H$(DMSO-d$_6$, 400 MHz) 8.50-8.38 (m, 1H, HC=), 8.20-8.00 (m, 4H, Ar), 7.96-7.79 (m, 6H, Ar), 7.68 (d, 1H, J=8.0. Ar), 7.60-7.32 (m, 3H, Ar), 6.72-6.55 (m, 2H, 2x HC=), 3.78 (s, 3H, NMe), 1.74 (s, 6H, 2×CH$_3$).

Example 5: X-Ray Based High Ambiguity Driven Protein-Protein Docking (HADDOCK) Model Of Human Defensin Peptide 1 (HNP1)

Figure 3:
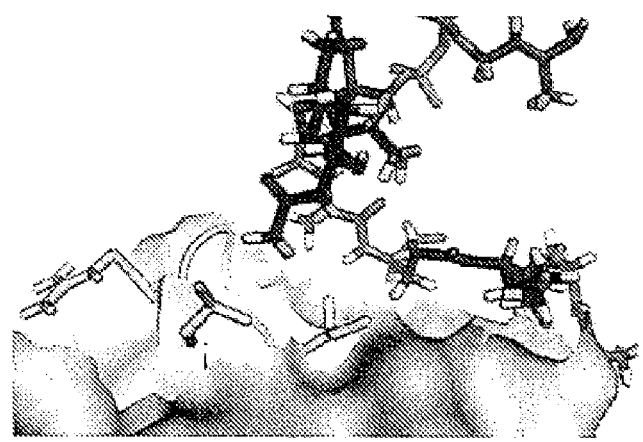
FIG. 3 is an X-ray-based, computer-generated HAD-DOCK model of human defensin peptide 1 (HNP1) with LII.
Figure 4:
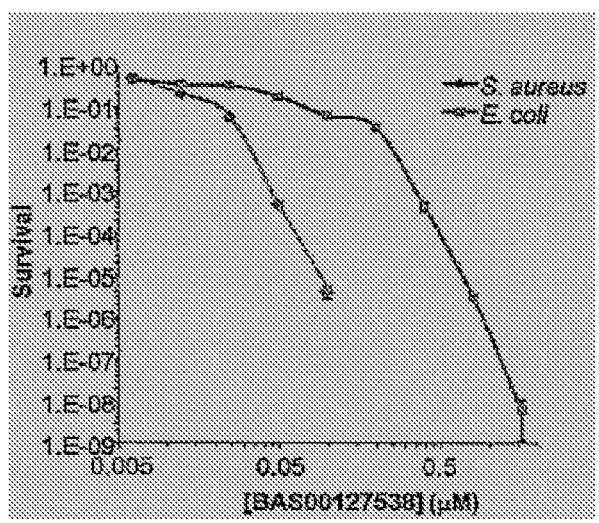
FIG. 4 shows survival data for *Staphylococcus aureus* and *Escherichia coli* (bacteria killing) in vitro, after treatment with BAS00127538.
Figure 5:
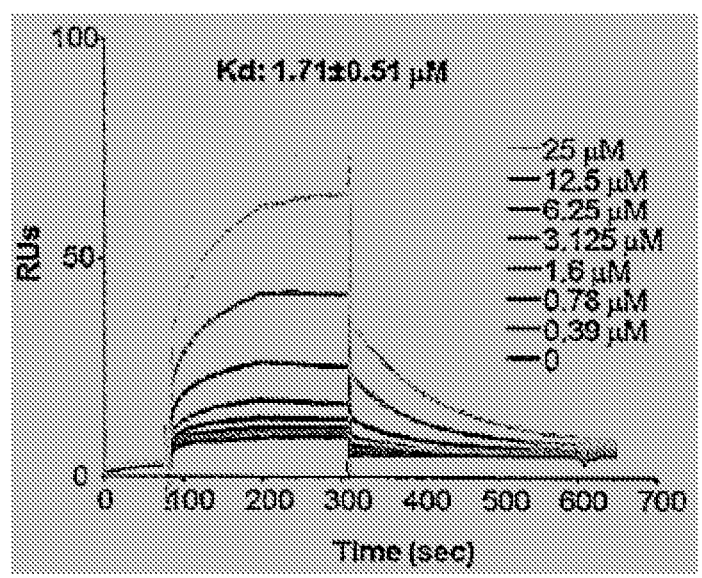
FIG. 5 shows the binding kinetics of BAS00127538 to 3-LII as determined by surface plasmon resonance.
Figure 6A:
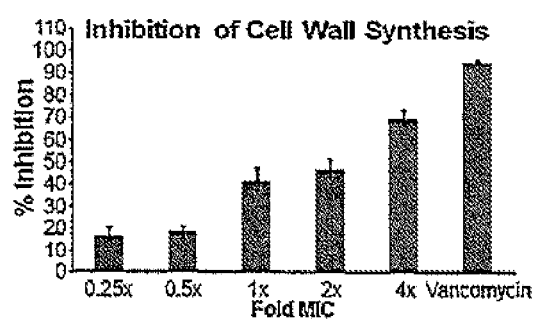
FIG. 6A, FIG. 6B, FIG. 6C, and FIG. 6D show data on the mechanism of action of BAS00127538.
Figure 6B:
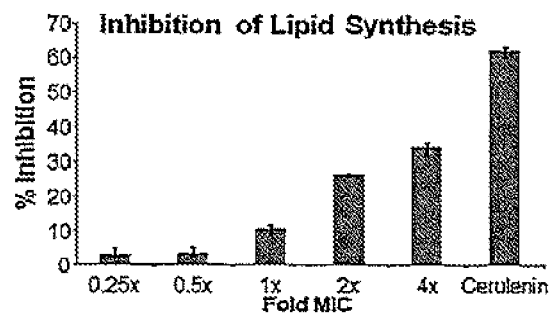
Figure 6C:
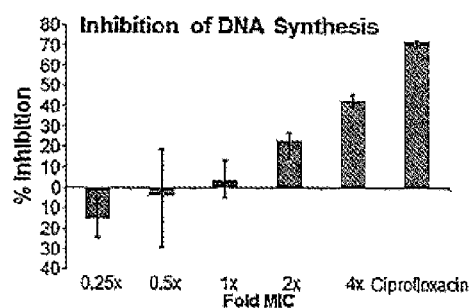
Figure 6D:
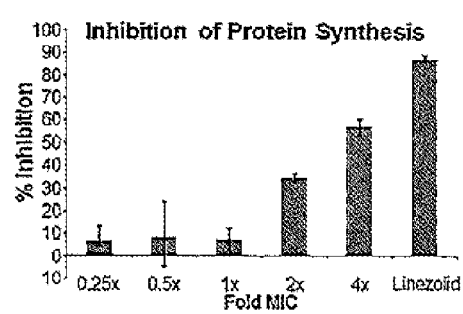

A 3D pharmacophore fingerprinting typed atom triangles (TAT) search was performed to represent specific side-chain structures and properties. See the model pictured in FIG. 3. Approximately 100 compounds of interest were found out of 1.5 million screened. Compound BAS00127538 was tested for survival in vivo against *Staphylococcus aureus* and *Escherichia coli* (FIG. 4) and to determine binding Kd (FIG. 5).

In addition, BAS00127538 and two other compounds were tested for activity against bacterial strains. See results in Table 3, below.

TABLE 3

Antibacterial activity of small molecule LII inhibitors.

| Organism | MMX#-ATCC# | BAS00127538 | 1499-1221 | 1611-0203 | Cipro | Linezolid |
|---|---|---|---|---|---|---|
| *Bacillus anthracis Sterne* | 109-NA | 0.5 | 0.5 | 1 | 0.5 | NA |
| *Bacillus anthracis** | Ames | 0.5 | 1 | 0.5 | 0.12 | NA |
| *Bacillus anthracis* (spores)* | Ames | 0.5 | 1 | 1 | 0.06 | NA |
| *Yersinia pestis** | CO92 | 8 | >64 | >64 | <0.06 | NA |
| *Burkholderia mallei** | 23344 | >64 | >64 | >64 | 2 | NA |
| *Burkholderia pseudomallei** | K96243 | 64 | >64 | >64 | 2 | NA |
| *Staphylococcus aureus* | 100-29213 | 0.5 | 0.25 | 2 | 0.5 | 4 |
| *Staphylococcus aureus* (MRSA) | 757-NA | 0.5 | 0.5 | 2 | >2 | 4 |
| *Enterococcus faecalis* | 101-29212 | 1 | 2 | 1 | 1 | 2 |
| *Enterococcus faecalis* (VRE) | 848-NA | 1 | 2 | 1 | >2 | 2 |
| *Streptococcus pneumoniae* | 1195-49619 | 8 | >8 | >16 | 1 | 2 |
| *Streptococcus pneumoniae* (PRSP) | 884-NA | 8 | >8 | >16 | 2 | 2 |
| *Escherichia coli* | 102.25922 | 4 | >16 | >4 | 0.008 | >64 |
| *Pseudomonas aeruginosa* | 103-27853 | >8 | >16 | >4 | 0.25 | >64 |

Reported MICs were adjusted to reflect instances where drug precipitation obscured the interpretation of the endpoint.

NA—not applicable,

MRSA—methicillin-resistant *S. aureus*,

VRE—vancomycin-resistant *enterococci*,

PRSP—penicillin-resistant *S. pneumoniae*,

Cipro—ciprofloxacin.

*Carried out according to DOD guidelines.

In order to investigate the mechanism of action of BAS00127538, exponentially growing S. aureus 29213 cells were exposed to the compounds compound and comparators in triplicate using 2.5% DMSO as "no drug" control. Cells were added to Mueller-Hinton broth or M9 medium for protein synthesis and further incubated in the presence of [$^{14}$C]N-acetyl glucosamine (cell wall), [$^{3}$H]glycerol (lipid), [$^{3}$H]thymidine (DNA), or [$^{3}$H] leucine (protein). Following incubation, reactions were stopped by addition of TCA (DNA, protein), 8% SDS (cell wall), or chloroform/methanol (lipid) and analyzed by scintillation counting. See FIG. 6, which shows data on the effects of the BAS00127583 compound on four bacterial parameters, inhibition of cell wall synthesis, lipid synthesis, DNA synthesis, and protein synthesis.

Figure 7A:
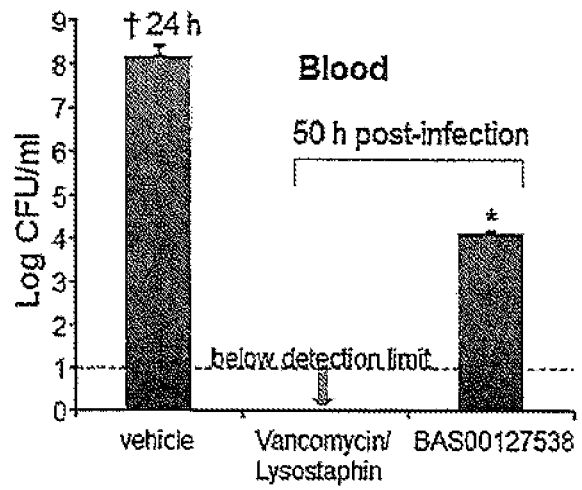
FIG. 7A and FIG. 7B present data on the bacteria present in spleen (FIG. 7A) and in blood (FIG. 7B), showing the efficacy of BAS00127538 in vivo.
Figure 7B:
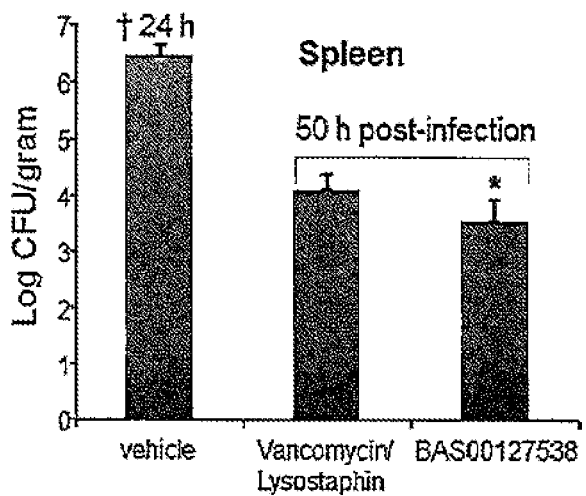

To determine the efficacy of BAS00127583 in vivo, samples were collected from vehicle-treated animals at 20 hours or at 50 hours post-infection from vancomycin- and BAS-treated animals. One animal treated with BAS did not survive beyond 28 hours. Results are presented in FIG. 7A and FIG. 7B.

Example 6: Plasma Stability and Pharmacokinetic Study of Compound 6jc48-1

A 2.5 mg/ml solution of compound 6jc48-1 was prepared in 10% DMSO, 50% PEG in PBS and administered at 2.5 mg/kg intravenous (tail vein) to male CD1 mice (N=3 per group). About 0.02 mL of blood was collected at 5 minutes, 15 minutes, 30 minutes, 1 hour, 2 hours, 4 hours, 6 hours, 8 hours and 14 hours post-treatment in centrifuge tubes containing 2 μL heparin (1,000 units). Compound 6jc48-1 was quantitated by LC/MS/MS using working solutions of 10, 20, 50, 100, 500, 1,000, 5,000 and 10,000 ng/mL compound 6jc48-1 prepared in blank CD1 mouse plasma as internal standards. No adverse clinical observations were observed for the duration of the experiment. For plasma stability measurements, compound 6jc48-1 (10 μg/mL) was incubated for 24 hours in the presence of serum (50%). Samples were taken after 2 minutes, 5 minutes, 15 minutes, 30 minutes, 1 hour, 2 hours and 19 hours. Stability of the compound was determined by LC/MS/MS.

Figure 8:
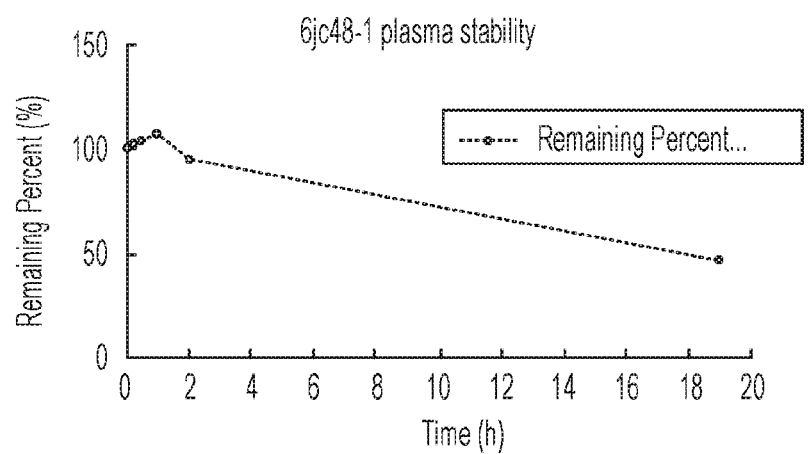
FIG. 8 is a graph showing the plasma stability of compound 6jc48-1 plasma stability, as tested by LC/MS/MS after 2 minutes, 5 minutes, 15 minutes, 30 minutes, 1 hour, 2 hours, and 19 hours in the presence of 50% serum.

The chemical stability of compound 6jc48-1 was tested directly in vivo by determining its stability in plasma as well as its pharmacokinetic profile. Test samples and standard samples (dexamethasone) were prepared and processed simultaneously and analyze under identical conditions. The results indicate that all test samples and standard samples passed acceptance criteria and could be detected by LC/MS/MS with confirmation of correct mass. Compound plasma stability was tested by LC/MS/MS after 2 minutes, 5 minutes, 15 minutes, 30 minutes, 1 hour, 2 hours and 19 hours. The data presented in FIG. 8 show that compound 6jc48-1 was stable after 2 hours in serum; after 19 hours, 46% of compound remained. This indicates that plasma stability is long lasting.

Figure 9:
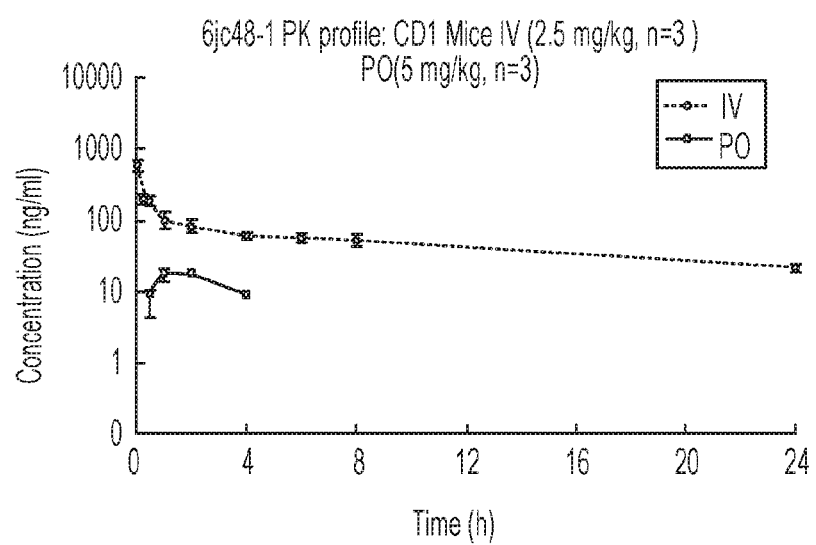
FIG. 9 is a graph showing the pharmacokinetic profile of compound 6jc48-1 in vivo.

Next, the pharmacokinetic (PK) profile of compound 6jc48-1 was compared to the parent compound BAS00127538. To determine the PK parameters, compounds were administered as a single dose of 2.5 mg/kg by intravenous injection (IV) or as a single oral dose (PO) of 5 mg/kg in 10% DMSO and 50% PEG400 in PBS, to mice (n=3), and the plasma concentration over time was determined by LC/MS/MS. Upon intravenous administration, compound 6jc48-1 was very stable in vivo and could be readily detected after 4 hours (PO) or 24 hours (IV). Half-life was determined by measuring the plasma concentration of compound by LC/MS/MS at the time points indicated in the figure. Compound 6jc48-1 had an in vivo half-life of 13.3 hours. See FIG. 8 and FIG. 9.

Based on these observations, the PK parameters were calculated for both compounds, and are presented in Table 4, below ($T_{1/2}$: half-life; $C_{max}$: maximum observed concentration; AUC: area under the curve; D: dose; Vss: volume of distribution; Cl: clearance; MRT: mean residence time; $F_{last}$ (bioavailability at last time point); $F_{inf}$ (inferred bioavailability)). The observed maximum plasma concentration was 1039 ng/mL and decreased slowly over time. The mean residence time (MRT) of the unchanged drug in circulation was 7.29 hours, with an area under the curve (AUCinf of 1769 h·ng·mL per hour. See FIG. 9 and Table 5-4, below. Volume of distribution at equilibrium (Vs) was 22.8 L·kg with total plasma clearance (CL) of 23.6 mL·min·kg. Compared to BAS00127538, compound 6jc48-1 showed markedly improved half-life (>13 hours vs. 0.22 hours), improved maximum concentration (1039 ng/mL vs. 101 ng/mL), increased volume of distribution (about 23 L/kg vs. 12.2 L/kg) and decreased clearance (23.6 mL/min/kg vs. 711 mL/min/kg). Upon oral administration, compound 6jc48-1 had a half-life of about 3 hours, with a calculated bioavailability of about 2.5%, whereas compound BAS00127538 could not be detected.

TABLE 4

Pharmacokinetic Properties of Compound 6jc48-1 and BAS00127538.

| Pharmacokinetic Parameter | BAS00127538 (IV administration) | Compound 6jc48-1 (IV administration) | Compound 6jc48-1 (PO administration) |
| --- | --- | --- | --- |
| $T_{1/2}$ (hours) | 0.227 | 13.3 ± 1.8 | 2.78 |
| $C_{max}$ (ng/mL) | 101 | 1039 ± 323 | 19.1 |
| $AUC_{last}$ (h*ng/mL) | 26.9 | 1340 ± 117 | 46.9 |
| $AUC_{Inf}$ (h*ng/mL) | 27.9 | 1769 ± 120 | 90 |
| $AUC_{Extrap}$ (%) | 4.38 | 24.3 ± 3.1 | 48.6 |
| $AUC_{last}/D$ (h*mg/mL) | 26.9 | 536 ± 47 | 9.4 |
| Vss_obs (L/kg) | 12.2 | 22.8 ± 2.9 | 1.75 |
| Cl_obs (mL/min/kg) | 711 | 23.6 ± 1.7 | NA |
| MRT (hours) | 0.226 | 7.29 ± 0.27 | NA |
| $F_{last}$ (%) | NA | NA | 1.9 |
| $F_{inf}$ (%) | NA | NA | 2.54 |

Example 7: Functional Characterization of Chemically Modified Compounds

The functional consequences of chemical modifications of the substituents around the diphenyl pyrylium core initially were evaluated in two functional assays: (1) antibacterial activity and (2) Lipid II binding as assayed by Surface Plasmon Resonance. See the results in Table 5, below, which provides a chemical and functional overview of the compounds generated for this study. In Table 5, a determination of "yes" for Lipid II binding indicates significant binding (binding more than 10 resonance units as determined by SPR), as discussed in Example 1E, above. ND indicates not done.

TABLE 5

Compound Structure and Function.

| Structural Formula and Compound Name | Chemical Formula | MW (g/mol) | IUPAC Name | Lipid II Binding | S. aureus Killing |
|---|---|---|---|---|---|
| 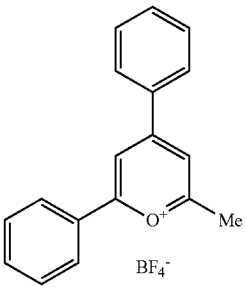 6jc26 | $C_{18}H_{15}BF_4O$ | 334.12 | 2-methyl-4,6-diphenylpyrylium boron tetrafluoride salt | no | >64 |
| 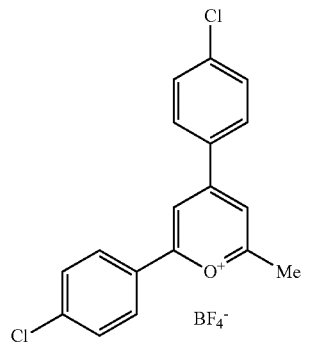 6jc32-1 | $C_{18}H_{13}BCl_2F_4O$ | 403.01 | 2,4-bis(4-chlorophenyl)-6-methylpyrylium boron tetrafluoride salt | no | >64 |
| 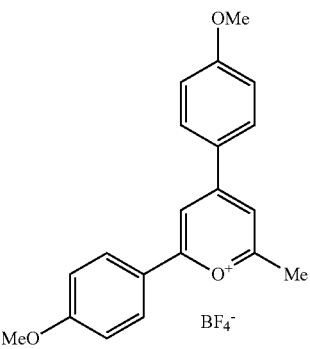 6jc32-2 | $C_{20}H_{19}BF_4O_3$ | 394.17 | 2,4-bis(4-methoxyphenyl)-6-methylpyrylium boron tetrafluoride salt | no | >64 |
| 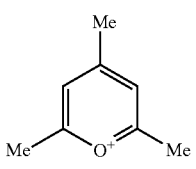 6jc36 | $C_8H_{11}BF_4O$ | 209.98 | 2,4,6-trimethylpyrylium boron tetrafluoride salt | no | >64 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 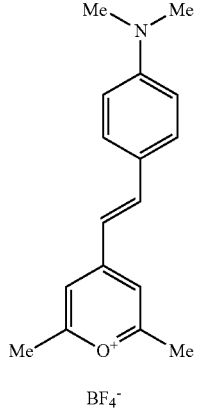 6jc37 | $C_{17}H_{20}BF_4NO$ | 341.15 | (E)-4-(4-(dimethylamino)styryl)-2,6-dimethylpyrylium boron tetrafluoride salt | no | 16 |
| 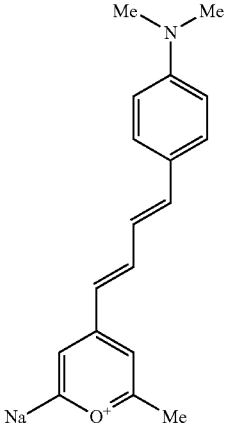 6jc38 | $C_{19}H_{22}BF_4NO$ | 367.19 | 4-((1E,3E)-4-(4-(dimethylamino)phenyl)buta-1,3-dien-1-yl)-2,6-dimethylpyrylium boron tetrafluoride salt | no | 32 |
| 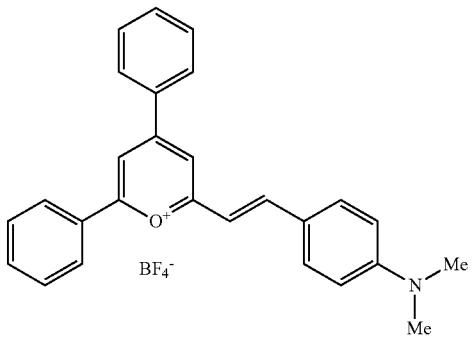 6jc39 | $C_{27}H_{24}BF_4NO$ | 465.29 | (E)-2-(4-(dimethylamino)styryl)-4,6-diphenylpyrylium boron tetrafluoride salt | yes | 2 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 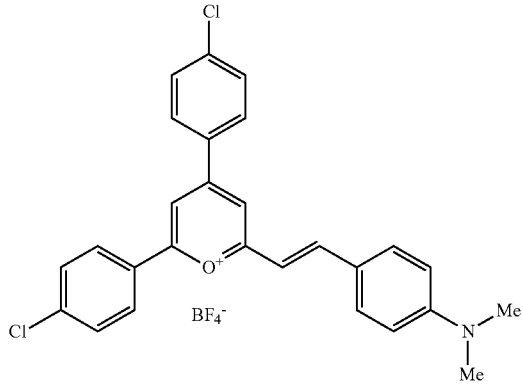 6jc41-1 | $C_{27}H_{22}Cl_2NO$ | 534.18 | (E)-2,4-bis(4-chlorophenyl)-6-(4-(dimethylamino)styryl)pyrylium boron tetrafluoride salt | yes | 32 |
| 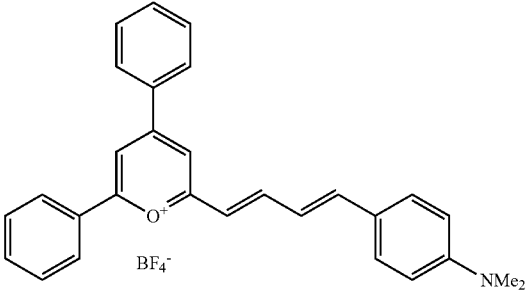 6jc43-1 | $C_{29}H_{26}BF_4NO$ | 491.33 | 2-((1E,3E)-4-(4-(dimethylamino)phenyl)buta-1,3-dien-1-yl)-4,6-diphenyl pyrylium boron tetrafluoride salt | yes | 4 |
| 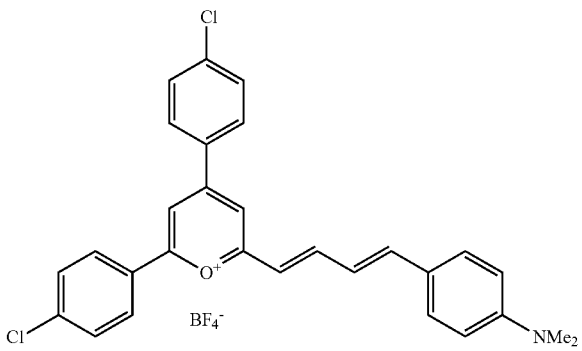 6jc43-2 | $C_{29}H_{24}BCl_2F_4NO$ | 560.22 | 2,4-bis(4-chlorophenyl)-6-((1E,3E)-4-(4-(dimethylamino)phenyl)buta-1,3-dien-1-yl)pyrylium boron tetrafluoride salt | ND | >64 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 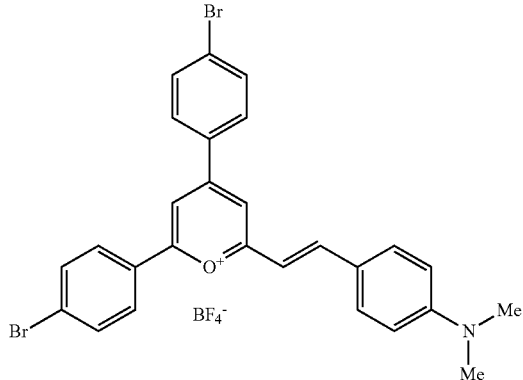 6jc48-1 | C$_{27}$H$_{22}$BBr$_2$F$_4$NO | 623.08 | (E)-2,4-bis(4-bromophenyl)-6-(4-(dimethylamino)styryl)pyrylium boron tetrafluoride salt | yes | 32 |
| 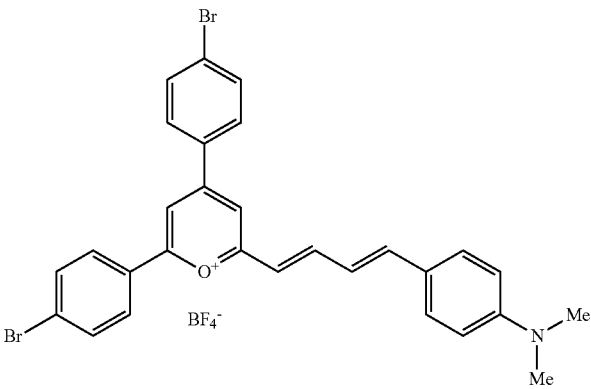 6jc48-2 | C$_{29}$H$_{24}$BBr$_2$F$_4$NO | 649.12 | 2,4-bis(4-bromophenyl)-6-((1E,3E)-4-(4-(dimethylamino)phenyl)buta-1,3-dien-1-yl)pyrylium boron tetrafluoride salt | yes | >64 |
| 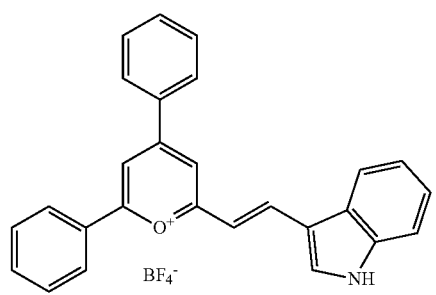 6jc49-1 | C$_{27}$H$_{20}$BF$_4$NO | 461.26 | (E)-2-(2-(1H-indol-3-yl)vinyl)-4,6-diphenylpyrylium boron tetrafluoride salt | yes | 1 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 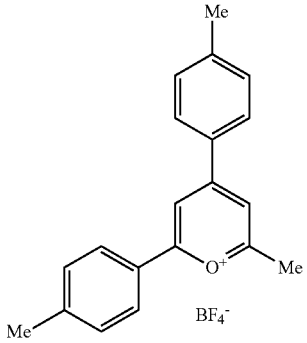 6jc50-2 | $C_{20}H_{19}BF_4O$ | 362.17 | 2-methyl-4,6-di-p-tolylpyrylium boron tetrafluoride salt | no | >64 |
| 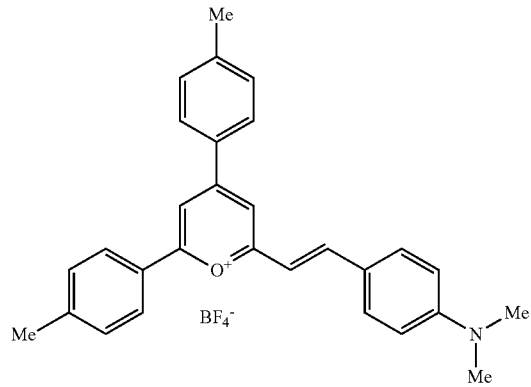 6jc51-1 | $C_{29}H_{28}BF_4NO$ | 493.34 | (E)-2-(4-(dimethylamino)styryl)-4,6-di-p-tolylpyrylium boron tetrafluoride salt | yes | 0.5 |
| 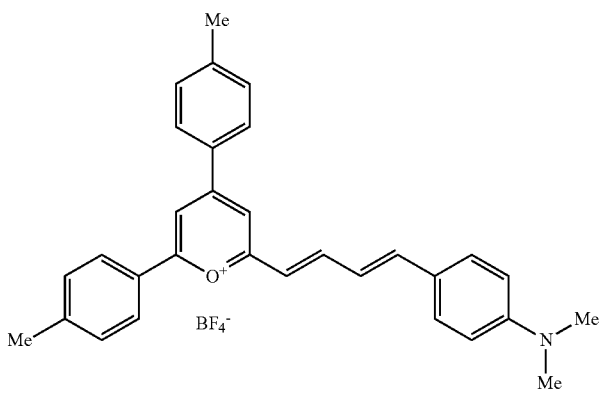 6jc51-2 | $C_{31}H_{30}BF_4NO$ | 519.38 | 2-((1E,3E)-4-(4-(dimethylamino)phenyl)buta-1,3-dien-1-yl)-4,6-di-p-tolylpyrylium boron tetrafluoride salt | yes | 2 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 6jc53-1 | C$_{27}$H$_{18}$BCl$_2$F$_4$NO | 530.15 | (E)-2-(2-(1H-indol-3-yl)vinyl)-4,6-bis(4-chlorophenyl) pyrylium boron tetrafluoride salt | yes | 16 |
| 6jc53-2 | C$_{29}$H$_{24}$BF$_4$NO | 489.31 | (E)-2-(2-(1H-indol-3-yl)vinyl)-4,6-di-p-tolylpyrylium boron tetrafluoride salt | yes | 4 |
| 6jc53-3 | C$_{27}$H$_{18}$BBr$_2$F$_4$NO | 619.05 | (E)-2-(2-(1H-indol-3-yl)vinyl)-4,6-bis(4-bromophenyl) pyrylium boron tetrafluoride salt | yes | >64 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 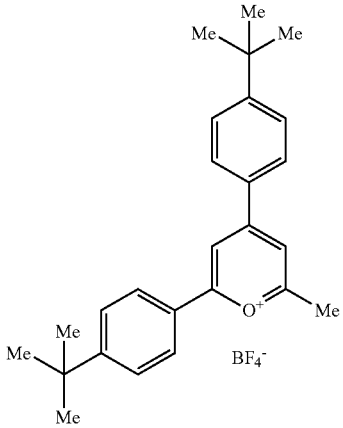 6jc56 | $C_{26}H_{32}BF_4O$ | 446.33 | 2,4-bis(4-(tert-butyl)phenyl)-6-methylpyrylium boron tetrafluoride salt | no | >64 |
| 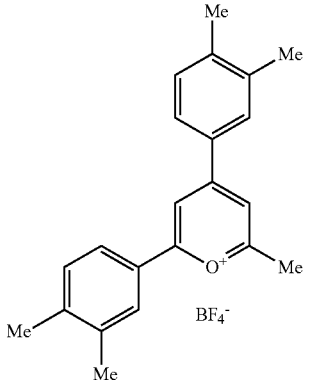 6jc57 | $C_{22}H_{23}BF_4NO$ | 390.22 | 2,4-bis(3,4-dimethylphenyl)-6-methylpyrylium boron tetrafluoride salt | no | >64 |
| 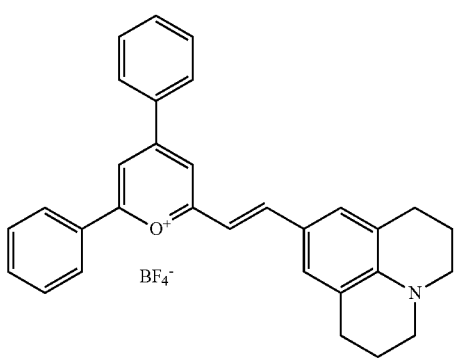 6jc58 | $C_{31}H_{28}BF_4NO$ | 517.36 | (E)-2-(2-(1,2,3,5,6,7-hexahydropyrido[3,2,1-ij]quinolin-9-yl)vinyl)-4,6-diphenylpyrylium boron tetrafluoride salt | yes | 1 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 6jc59-1 | $C_{31}H_{32}BF_4NO$ | 521.40 | (E)-2-(4-(dimethylamino)styryl)-4,6-bis(3,4-dimethylphenyl)pyrylium boron tetrafluoride salt | yes | 2 |
| 6jc59-2 | $C_{31}H_{28}BF_4NO$ | 547.43 | 2-((1E,3E)-4-(4-(dimethylamino)phenyl)buta-1,3-dien-1-yl)-4,6-bis(3,4-dimethylphenyl)pyrylium boron tetrafluoride salt | yes | 32 |
| 6jc59-3 | $C_{33}H_{34}BF_4NO$ | 517.36 | (E)-2-(2-(1H-indol-3-yl)vinyl)-4,6-bis(3,4-dimethylphenyl)pyrylium boron tetrafluoride salt | yes | 4 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 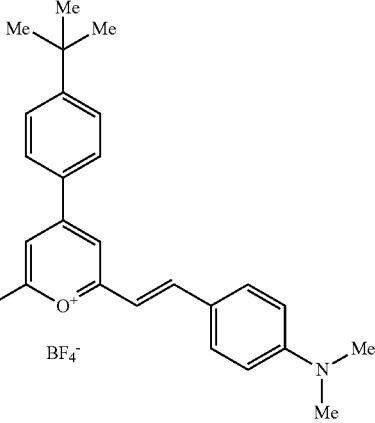 6jc60-1 | $C_{35}H_{40}BF_4NO$ | 577.50 | (E)-2,4-bis(4-(tert-butyl)phenyl)-6-(4-(dimethylamino)styryl)pyrylium boron tetrafluoride salt | yes | 8 |
| 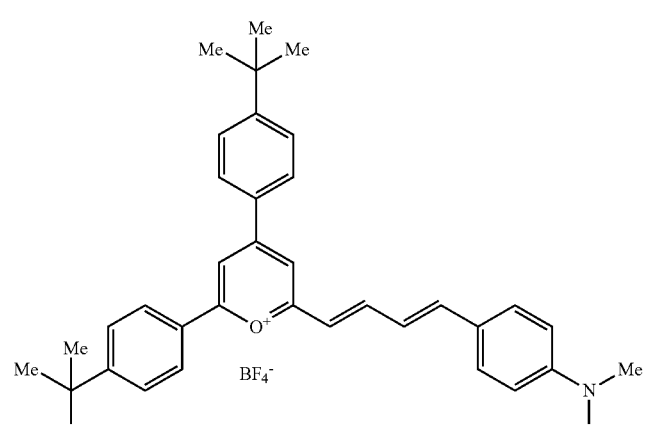 6jc60-2 | $C_{37}H_{42}BF_4NO$ | 603.54 | 2,4-bis(4-(tert-butyl)phenyl)-6-((1E,3E)-4-(4-(dimethylamino)phenyl)buta-1,3-dien-1-yl)pyrylium boron tetrafluoride salt | yes | 64 |
| 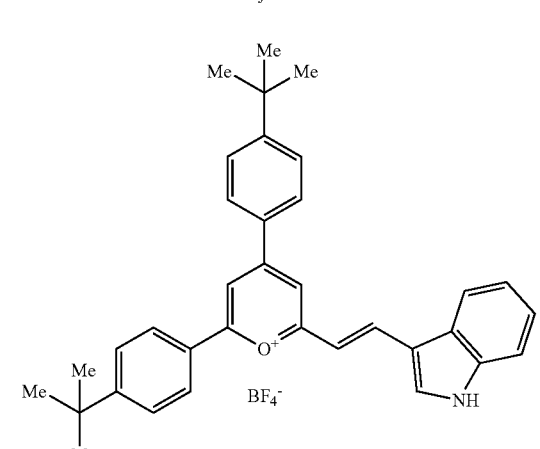 6jc60-3 | $C_{35}H_{36}BF_4NO$ | 573.47 | (E)-2-(2-(1H-indol-3-yl)vinyl)-4,6-bis(4-(tert-butyl)phenyl)pyrylium boron tetrafluoride salt | yes | 32 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 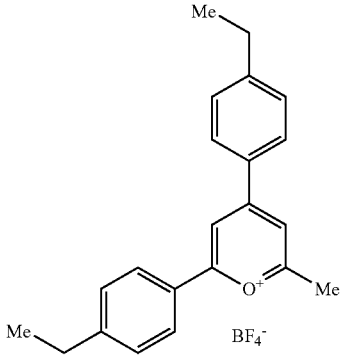 6jc61 | $C_{22}H_{23}BF_4O$ | 390.22 | 2,4-bis(4-ethylphenyl)-6-methylpyrylium boron tetrafluoride salt | no | >64 |
| 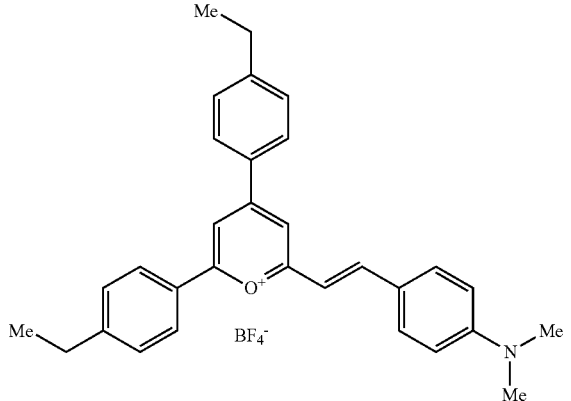 6jc64-1 | $C_{31}H_{32}BF_4NO$ | 521.40 | (E)-2-(4-(dimethylamino)styryl)-4,6-bis(4-ethylphenyl)pyrylium boron tetrafluoride salt | yes | 1 |
| 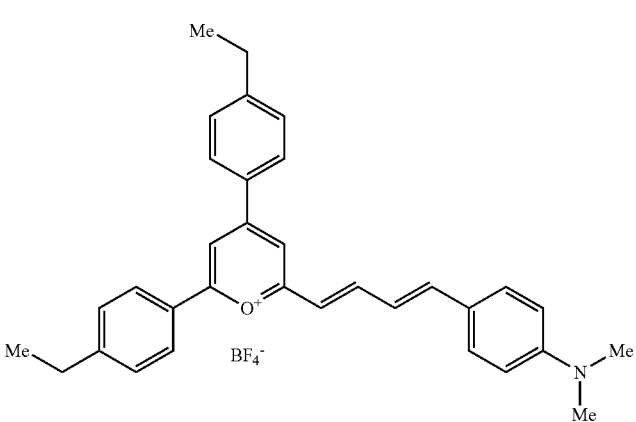 6jc64-2 | $C_{33}H_{34}BF_4NO$ | 547.43 | 2-((1E,3E)-4-(4-(dimethylamino)phenyl)buta-1,3-dien-1-yl)-4,6-bis(4-ethylphenyl)pyrylium boron tetrafluoride salt | yes | 8 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 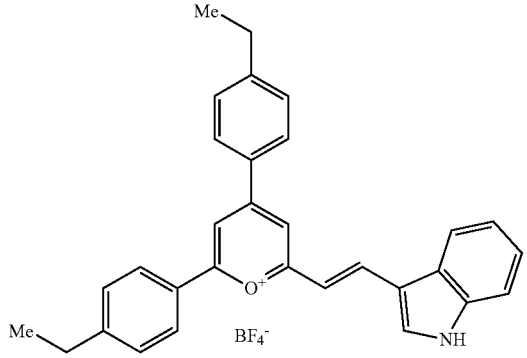<br>6jc64-3 | $C_{31}H_{28}BF_4NO$ | 517.36 | (E)-2-(2-(1H-indol-3-yl)vinyl)-4,6-bis(4-ethylphenyl)pyrylium boron tetrafluoride salt | yes | 4 |
| 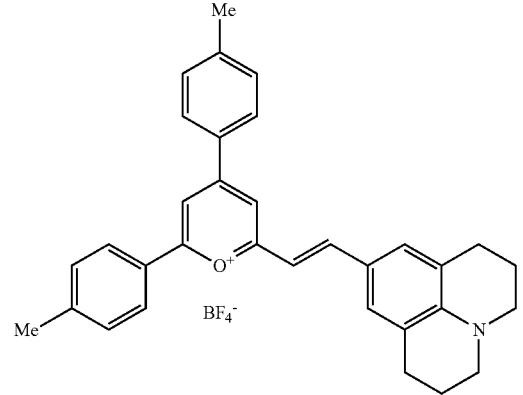<br>6jc65-1 | $C_{33}H_{32}BF_4NO$ | 545.42 | (E)-2-(2-(1,2,3,5,6,7-hexahydropyrido[3,2,1-ij]quinolin-9-yl)vinyl)-4,6-di-p-tolylpyrylium boron tetrafluoride salt | yes | 1 |
| 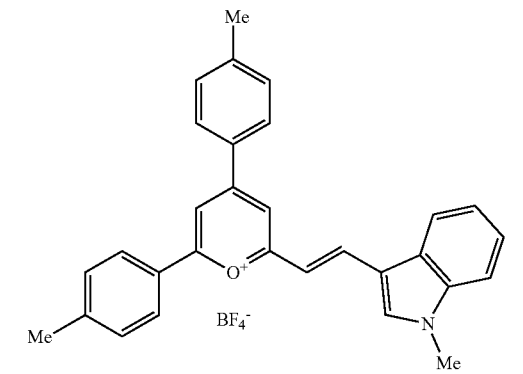<br>6jc65-2 | $C_{30}H_{26}BF_4NO$ | 503.34 | (E)-2-(2-(1-methyl-1H-indol-3-yl)vinyl)-4,6-di-p-tolylpyrylium boron tetrafluoride salt | yes | 0.5 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 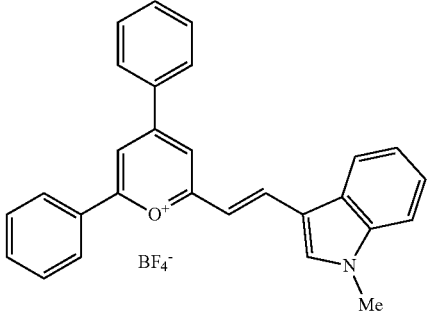 6jc66-1 | $C_{28}H_{22}BF_4NO$ | 475.28 | (E)-2-(2-(1-methyl-1H-indol-3-yl)vinyl)-4,6-diphenylpyrylium boron tetrafluoride salt | yes | 0.5 |
| 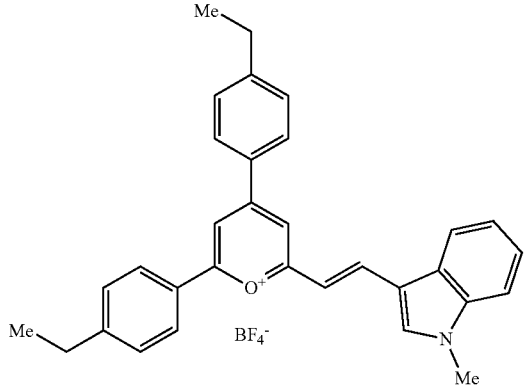 6jc66-2 | $C_{32}H_{30}BF_4NO$ | 531.39 | (E)-2,4-bis(4-ethylphenyl)-6-(2-(1-methyl-1H-indol-3-yl)vinyl)pyrylium boron tetrafluoride salt | yes | 1 |
| 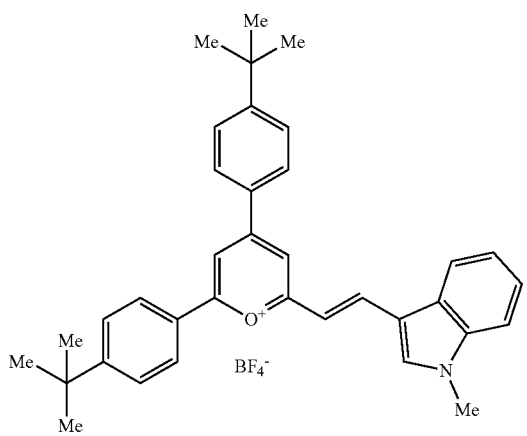 6jc66-3 | $C_{36}H_{38}BF_4NO$ | 587.50 | (E)-2,4-bis(4-(tert-butyl)phenyl)-6-(2-(1-methyl-1H-indol-3-yl)vinyl)pyrylium boron tetrafluoride salt | yes | 16 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 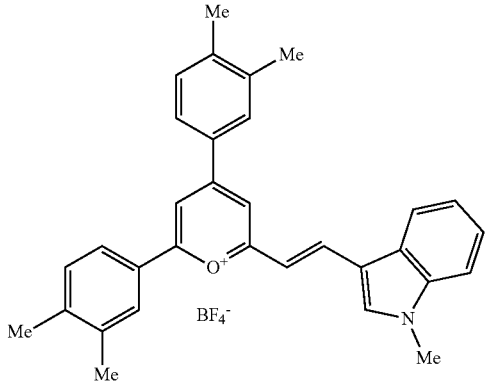 6jc66-4 | $C_{32}H_{30}BF_4NO$ | 531.39 | (E)-2,4-bis(3,4-dimethylphenyl)-6-(2-(1-methyl-1H-indol-3-yl)vinyl)pyrylium boron tetrafluoride salt | yes | 1 |
| 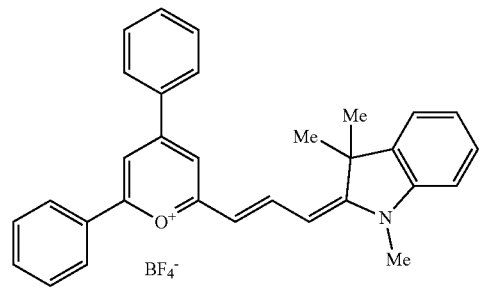 6jc67 | $C_{31}H_{28}BF_4NO$ | 430.57 | 2,4-diphenyl-6-((1E,3E)-3-(1,3,3-trimethylindolin-2-ylidene)prop-1-en-1-yl)pyrylium boron tetrafluoride salt | yes | 0.5 |
| 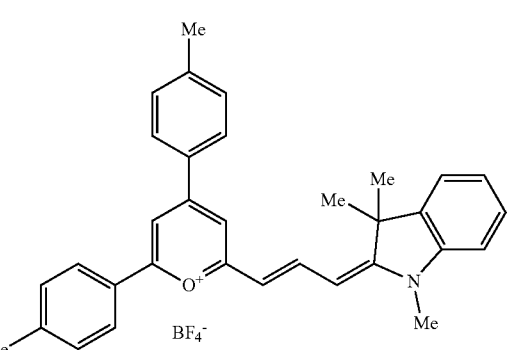 6jc67-A | $C_{33}H_{32}BF_4NO$ | 448.57 | 2,4-di-p-tolyl-6-((1E,3E)-3-(1,3,3-trimethylindolin-2-ylidene)prop-1-en-1-yl)pyrylium boron tetrafluoride salt | yes | 1 |

TABLE 5-continued

Compound Structure and Function.

| Structural Formula and Compound Name | Chemical Formula | MW (g/mol) | IUPAC Name | Lipid II Binding | *S. aureus* Killing |
|---|---|---|---|---|---|
| 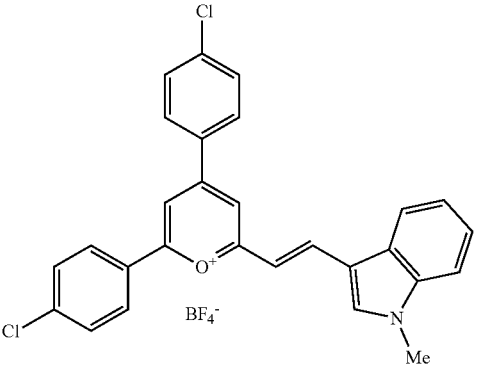<br>6jc68-1 | $C_{28}H_{20}BCl_2F_4NO$ | 544.18 | (E)-2,4-bis(4-chlorophenyl)-6-(2-(1-methyl-1H-indol-3-yl)vinyl)pyrylium boron tetrafluoride salt | ND | 64 |
| 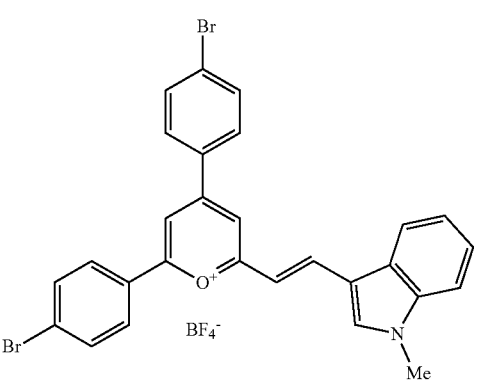<br>6jc68-2 | $C_{28}H_{20}BBr_2F_4NO$ | 633.08 | (E)-2,4-bis(4-bromophenyl)-6-(2-(1-methyl-1H-indol-3-yl)vinyl)pyrylium boron tetrafluoride salt | ND | 64 |
| 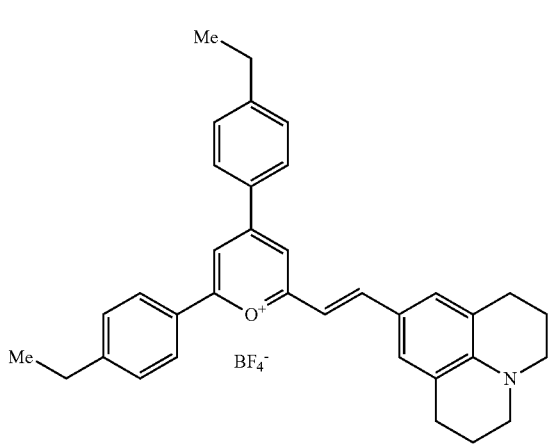<br>6jc69-1 | $C_{35}H_{36}BF_4NO$ | 573.74 | (E)-2,4-bis(4-ethylphenyl)-6-(2-(1,2,3,5,6,7-hexahydropyrido[3,2,1-ij]quinolin-9-yl)vinyl)pyrylium boron tetrafluoride salt | yes | 1 |

103
104

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 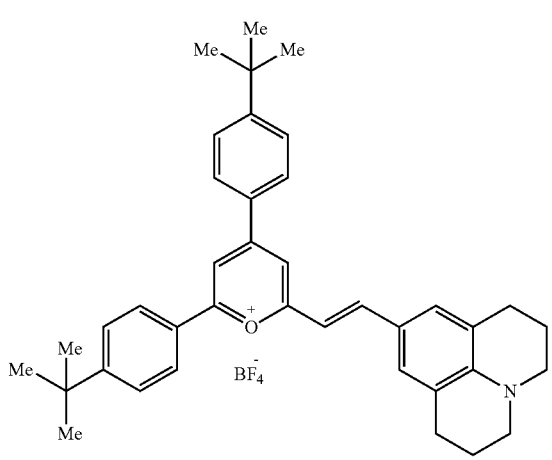 6jc69-2 | C$_{39}$H$_{44}$BF$_4$NO | 629.58 | (E)-2,4-bis(4-(tert-butyl)phenyl)-6-(2-(1,2,3,5,6,7-hexahydropyrido[3,2,1-ij]quinolin-9-yl)vinyl)pyrylium boron tetrafluoride salt | yes | 32 |
| 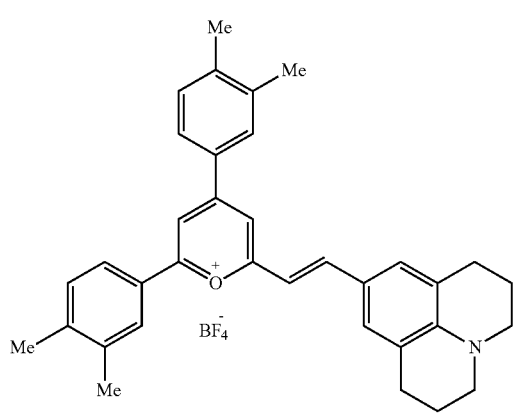 6jc69-3 | C$_{37}$H$_{40}$BF$_4$NO | 573.47 | (E)-2,4-bis(3,4-dimethylphenyl)-6-(2-(1,2,3,5,6,7-hexahydropyrido[3,2,1-ij]quinolin-9-yl)vinyl)pyrylium boron tetrafluoride salt | yes | 0.5 |
| 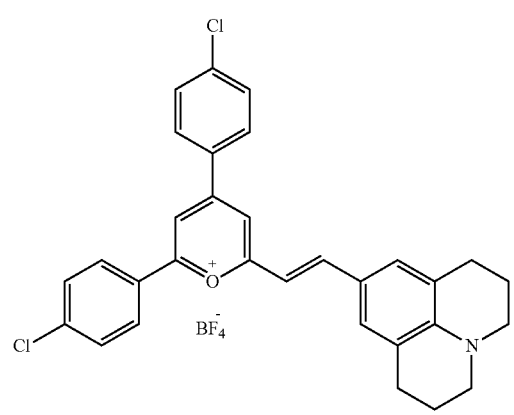 6jc69-4 | C$_{31}$H$_{26}$BCl$_2$F$_4$NO | 586.25 | (E)-2,4-bis(4-chlorophenyl)-6-(2-(1,2,3,5,6,7-hexahydropyrido[3,2,1-ij]quinolin-9-yl)vinyl)pyrylium boron tetrafluoride salt | yes | 1 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 6jc69-5 | $C_{31}H_{26}BBr_2F_4NO$ | 675.16 | (E)-2,4-bis(4-bromophenyl)-6-(2-(1,2,3,5,6,7-hexahydropyrido[3,2,1-ij]quinolin-9-yl)vinyl)pyrylium boron tetrafluoride salt | yes | 4 |
| 6jc76-1 | $C_{35}H_{36}BF_4NO$ | 573.47 | 2,4-bis(4-ethylphenyl)-6-((1E,3E)-3-(1,3,3-trimethylindolin-2-ylidene)prop-1-en-1-yl)pyrylium boron tetrafluoride salt | | |
| 6jc77-1 | $C_{31}H_{26}BCl_2F_4NO$ | 586.25 | 2,4-bis(4-chlorophenyl)-6-((1E,3E)-3-(1,3,3-trimethylindolin-2-ylidene)prop-1-en-1-yl)pyrylium boron tetrafluoride salt | | |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 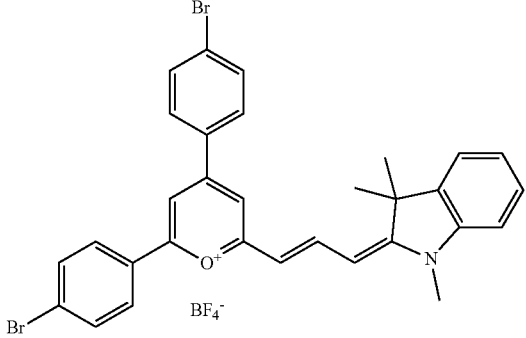 6jc77-2 | $C_{31}H_{26}BBr_2F_4NO$ | 675.16 | 2,4-bis(4-bromophenyl)-6-((1E,3E)-3-(1,3,3-trimethylindolin-2-ylidene)prop-1-en-1-yl)pyrylium boron tetrafluoride salt | | |
| 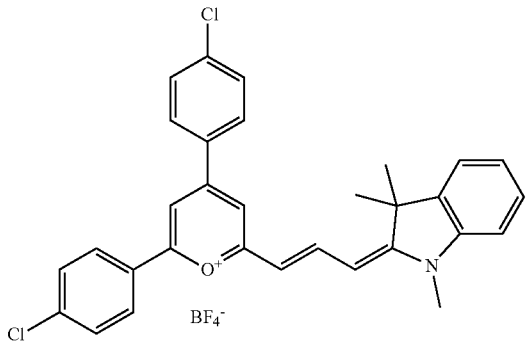 7jc42-1 | $C_{31}H_{26}BCl_2F_4NO$ | | 2,4-bis(4-chlorophenyl)-6-((1E,3E)-3-(1,3,3-trimethylindolin-2-ylidene)prop-1-en-1-yl)pyrylium boron tetrafluoride salt | | |
| 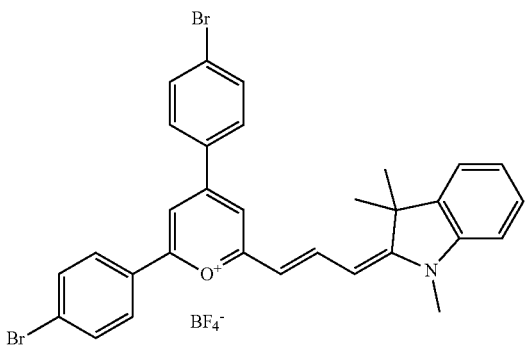 7jc42-2 | $C_{31}H_{26}BBr_2F_4NO$ | | 2,4-bis(4-bromophenyl)-6-((1E,3E)-3-(1,3,3-trimethylindolin-2-ylidene)prop-1-en-1-yl)pyrylium boron tetrafluoride salt | | |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 7jc46-1 | $C_{27}H_{22}BF_6NO$ | 501.27 | 2-((1E,3E)-4-(4-(dimethylamino)phenyl)buta-1,3-dien-1-yl)-4,6-bis(4-fluorophenyl)pyrylium boron tetrafluoride salt | | |
| 7jc47-1 | $C_{27}H_{22}BF_6NO$ | 501.27 | (E)-2-(4-(dimethylamino)styryl)-4,6-bis(4-fluorophenyl)pyrylium boron tetrafluoride salt | | |
| 7jc47-2 | $C_{29}H_{24}BF_6NO$ | 527.31 | 2-((1E,3E)-4-(4-(dimethylamino)phenyl)buta-1,3-dien-1-yl)-4,6-bis(4-fluorophenyl)pyrylium boron tetrafluoride salt | | |

Based on the results of these functional assays, selected compounds were further assayed for: (3) broad-range antibacterial activity and (4) cellular cytotoxicity against mammalian cells (HeLa) expressed as the concentration at which cell viability is decreased by 50% ($CC_{50}$). The medium used was cation-adjusted Mueller Hinton broth, including 10% BHI for E. faecium spp. Measured Lipid II binding was also further qualified by determining the binding constant of selected compounds. Further data from these assays are presented in Table 6, below, and represent the geomean of 2 samples. Concentrations (minimal inhibitory concentrations (MIC)) are given in µg/mL. The medium used was cation-adjusted Mueller-Hinton broth containing 10% BHI for E. faecium spp.; *CC50 based on E. faecium EF1509.

To explore the role of the indolene group on the potency, toxicity and LII binding of these compounds, a series of analogs were synthesized in which the indolene moiety was replaced by varying aldehydes at the $R^2$ position (see FIG. 10). Based on anti-bacterial activity, substitution of these moieties at the $R^2$ position can be ranked from highest to lowest (antibacterial) potency as: julolidine derivative (6jc65-1)>N-methyl-3-indolyl (6jc53-2)>3-indolyl (6jc53-2)>4-dimethylaminophenyl (6jc51-1)>N,N-dimethyl-4-vinylaniline (6jc51-2). Antibacterial killing potency was correlated with cytotoxicity. Notably, with the exception of compounds 6jc51-1, 6jc58 and 6jc67A, all compounds displayed reduced activity against Gram-negative species.

Effects on activity due to modifications to the $R^1$ positions on the two phenyl rings of the pyrylium core are summarized in FIG. 10. Compared to the parent compound 6jc48-1, none of the $R^1$ substitutions in generic Formula I shown here markedly enhanced potency or breadth of antibacterial activity. Irrespective of variations at the $R^2$ position, para-methyl (compounds: 6jc51-1, 6jc51-2, 6jc53-2, 6jc65-1, 6jc65-2), meta,para-dimethyl (compounds: 6jc59-1, 6jc59-2, 6jc59-3, 6jc66-4, 6jc69-3) or para-ethyl (compounds: 6jc64-1, 6jc64-2, 6jc64-3, 6jc66-2, 6jc69-1) groups at the $R^1$ position retained antibacterial activity most potently. Substitution of the $R^1$ moiety with tert-butyl, tri-methyl, chloride or bromide in the para position significantly reduced antibacterial killing.

Although in general antibacterial activity correlated with LII binding and cellular cytotoxicity, the 6jc48-1 and 6jc48-2 compounds were a notable exception. These compounds revealed high affinity LII binding and markedly reduced cellular cytotoxicity, with a surprisingly specific anti-*Enterococci* activity. These compounds, and their derivatives, are preferred compounds. The following compounds are compounds contemplated as part of this invention, and are useful as antibiotic compounds for use in treatment: 6jc39, 6jc43-1, 6jc48-1, 6jc48-2, 6jc51-1, 6jc51-2, 6jc53-2, 6jc58, 6jc59-1, 6jc59-2, 6jc59-3, 6jc64-1, 6jc64-2, 6jc64-3, 6jc65-1, 6jc65-2, 6jc66-1, 6jc66-2, 6jc66-3, 6jc66-4, 6jc67, 6jc69-1, 6jc69-3, 6jc69-4, 6jc76-1, 6jc76-2, 6jc77-1, 6jc77-2, 7jc46-1, 7jc47-1, and 7jc47-2. Preferred compounds include: 6jc48-1, 6jc58, 6jc66-3, 6jc66-4, 6jc67, 6jc77-1, 6jc77-2, 7jc46-1, 7jc47-1, and 7jc47-2, and most highly preferred compounds include: 6jc48-1, 6jc67, 7jc46-1, 7jc47-1, and 7jc47-2.

Based on its markedly decreased cytotoxicity (see FIG. 10), compound 6jc48-1 was selected for further analysis. First, given its specific potency against *Enterococci*, compound 6jc48-1 was tested for potency against a wider array of *E. faecium* and *E. faecalis* strains (see Table 6, below). For these tests, cation-adjusted Mueller Hinton broth, containing 10% brain-heart infusion (BHI) was used. Concentrations (MIC) are given in μg/mL. The compound was effective in killing the tested drug-resistant strains, confirming its specific activity against these species.

Figure 11A:
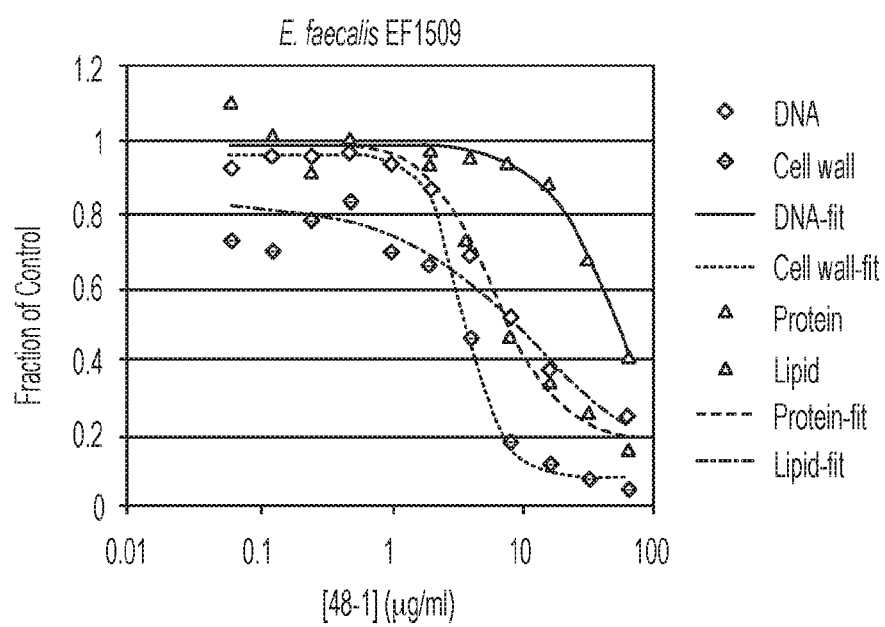
FIG. 11A and FIG. 11B show the effects of 6jc48-1 (MIC 4 µg/ml.
Figure 11B:
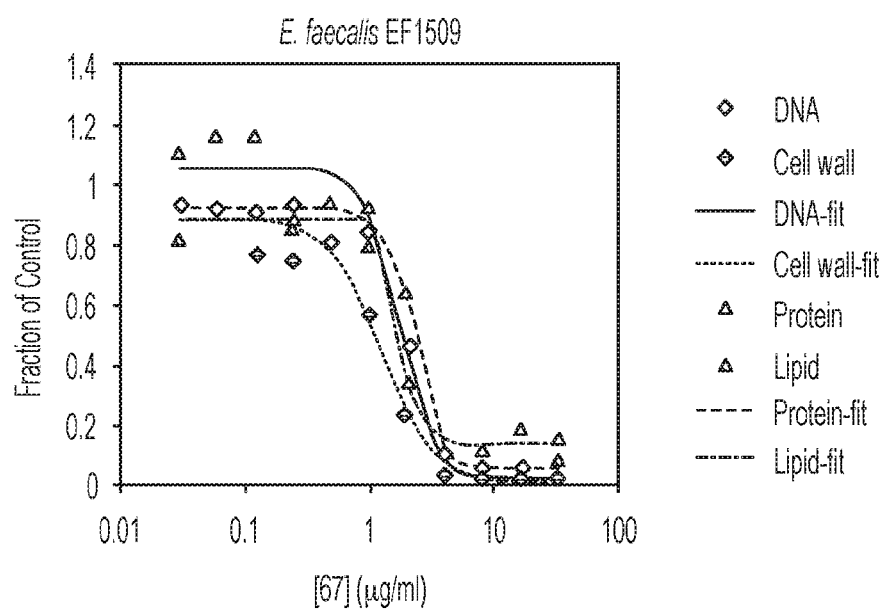

Compound 6jc48-1 (MIC: 4 μg/mL) most potently inhibited cell wall synthesis ($IC_{50}$ of 3.8 μg/mL), followed by inhibition of lipid and DNA synthesis ($IC_{50}$ of 7.8 and 8.3 μg/mL, respectively). See FIG. 11. Compound 6jc67 (MIC: 2 μg/mL), the de novo synthesized parent BAS00127538, also most potently inhibited cell wall synthesis ($IC_{50}$ of 1.1 μg/mL), followed by inhibition of DNA ($IC_{50}$ of 1.8 μg/mL) and lipid synthesis ($IC_{50}$ of 2.3 μg/mL), as previously reported for commercially available BAS00127538. Surprisingly, 6jc48-1 showed a markedly reduced inhibition of protein synthesis ($IC_{50}$ of 50.4 μg/mL) compared to the 6jc67 (BAS00127538) with an $IC_{50}$ of 1.6 μg/mL. Interestingly, the methyl analog of BAS00127538 also has the same activity of BAS00127538.

Without wishing to be bound by theory, it is possible that the pyrylium moiety in compound 6jc48-1 causes the compound to be reactive toward nucleophiles, including water, amines, and thiols. Therefore, compound 6jc48-1 was tested for drug-like properties in in vitro assays, including stability and a pharmacokinetic profile.

Compound stability was tested by LC/MS/MS after 2 minutes, 5 minutes, 15 minutes, 30 minutes, 1 hour, 2 hours and 19 hours. The analysis showed that compound 6jc48-1 has favorable purity and solubility, liver microsome stability, and with the exception of CYP3A4/BFC, did not inhibit P450 enzyme activity at >10 μM. Further, plasma protein binding was found to be 89%. See the results in Table 7, below. Due to incompatibility with solubilization conditions, membrane permeability and hepatotoxicity could not be determined.

TABLE 7

Drug-like Properties of Compound 6jc48-1, Tested in Vitro.

| Assay | Result |
|---|---|
| Purity (LC-MS-MS) | >95% |
| Solubility in water (laser nephelometry) | >50 μg/mL (n = 3) |
| Liver micosome stability (human; 1 hour; 37° C.) | Half-life >60 minutes Clearance <23 μL/min/mg |
| Plasma protein binding (human; Transil ™) | 89% ± |
| P450 enzyme inhibition (IC50 fluorescence) CYP3A4/DBF | >10 μM |
| P450 enzyme inhibition (IC50 fluorescence) CYP3A4/BFC | 1.3 μM |

TABLE 6

Activity of Compound 6jc48-1 and Derivatives against *Enterococcus* spp. Compound

| Organism | ATCC# | 6jc48-1 | V | BAS00127538 | 6jc67A | 6jc69-1 | 6jc69-3 |
|---|---|---|---|---|---|---|---|
| E. faecium | IH79985 | 8 | ND | 2 | 2 | 8 | 4 |
| E. faecium | C110914 | 4 | ND | 2 | 1 | 4 | 2 |
| E. faecium | S1559 | 2 | ND | 2 | 1 | 2 | 2 |
| E. faecalis | 51575 | 2 | ND | 2 | 1 | 2 | 2 |
| E. faecalis | 51299 | 4 | ND | 2 | 1 | 1 | 1 |
| E. faecalis | C99707 | 2 | ND | 2 | 1 | 1 | 1 |
| E. faecium* | none | 4-16 | >32 | ND | ND | ND | ND |
| E. faecalis* | none | 4-16 | >32 | ND | ND | ND | NC |

ND = not determined;
*clinical isolates sensitive to linezolid and daptomycin,
n = 5;
V = vancomycin.

TABLE 7-continued

Drug-like Properties of Compound 6jc48-1, Tested in Vitro.

| Assay | Result |
|---|---|
| P450 enzyme inhibition (IC50 fluorescence) CYP2D6/AMMC | >10 µM |
| P450 enzyme inhibition (IC50 fluorescence) CYP2C19/CEC | >10 µM |

DBF: dibenzylfluorescein; BFC: 7-benzoyloxy-4-trifluoromethyl coumarin; AMMC: 3-[2-(N,N-diethyl-N-methylamino)ethyl]-7-methoxy-4-methylcoumarin; CEC: 3-cyano-7-ethoxycoumarin.

Example 8: Bacterial Killing Activity in Additional Compounds

Ability to kill bacteria was determined as discussed in Example 1E, above. See Table 8, below.

TABLE 8

| Bacterial Killing. | | | |
|---|---|---|---|
| Compound | S. aureus | E. faecium | E. coli |
| 6jc48-1 | 16 | 4 | >64 |
| 7jc42-1 | 8 | 32 | >64 |
| 7jc42-2 | 32 | 32 | >64 |
| 7jc46-1 | 1 | 2 | >64 |
| 7jc47-1 | 1 | 1 | >64 |
| 7jc47-2 | 1 | 1 | >64 |
| 7jc50 | 8 | >64 | >64 |
| 7jc51 | 64 | >64 | >64 |

Example 9: In Vivo Efficacy of Compound 6jc48-1

General methods for the murine model of sepsis were as follows. To assess the protective potency of defensin mimetic compound 6jc48-1, groups of 5 mice were inoculated intraperitoneally with approximately $5 \times 10^6$ CFU/mL of *Enterococcus faecalis* EF1509 in 500 µL saline solution plus 4.5% (w/v) porcine gastric mucin (Sigma™ Chemical Co., St. Louis, Mo.). Infected animals subsequently were treated by intravenous injection 30 minutes, 120 minutes and 300 minutes post-infection with 5 mg/kg of the compound in 100 µL of one of (1) Tris-buffered saline solution, 50% PEG400, 10% DMSO (v/v), (2) linezolid (50 mg/kg, sterile Tris-buffered saline solution, 50% PEG400, 10% DMSO (v/v) as a positive control) or (3) vehicle (Tris-buffered saline solution, 50% PEG400, 10% DMSO (v/v) as a negative control). Animals were observed closely during a period of 7 days and mice that showed signs of severe sepsis were humanely euthanized. Mice were anesthetized by intraperitoneal injection of ketamine (80-100 mg/kg) and xylazine (10-15 mg/kg). Blood samples were collected by retroorbital puncture using lithium-heparin polystyrene tubes to prevent coagulation. Spleens were harvested aseptically, weighed and homogenized in 500 µL sterile saline solution using an IKA™ basic disperser (IKA™, Wilmington N.C.). Whole blood samples and spleen homogenates were serially diluted and plated onto lysogeny broth (LB) agar plates. Bacterial counts were determined following a 24-hour incubation at 37° C. and expressed as CFU per milliliter for blood and CFU per gram for spleen.

Preliminary maximum tolerated dose studies indicated that compound 6jc48-1 could be safely administered intraperitoneally at doses as high as 100 mg/kg. Solubility of the compound restricted testing concentrations above 100 mg/kg.

Figure 12:
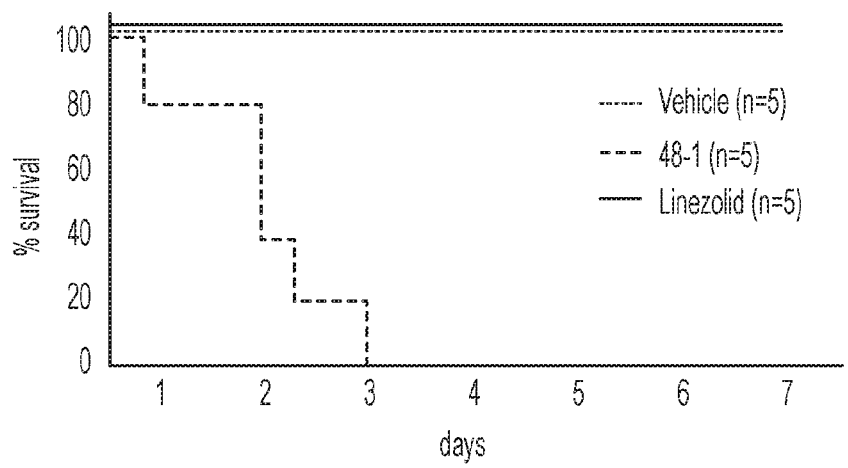
FIG. 12 shows the percent survival of mice with the indicated treatments.

A specific test was performed as follows. Based on the data obtained in the pharmacokinetic analysis, mice (n=5) were inoculated peritoneally with *E. faecalis* EF1509 and treated after 30 minutes and three times every 90 minutes following with compound at 5 mg/kg intravenously. Animals were monitored for survival. Blood and spleen samples were collected and tested for bacteria. Bacterial counts were determined and compared to control treatment with linezolid as measures of efficacy. Animals treated with vehicle (negative control) did not survive the length of the experiment. See FIG. 12, which shows the % survival for the various treatments.

Figure 13:
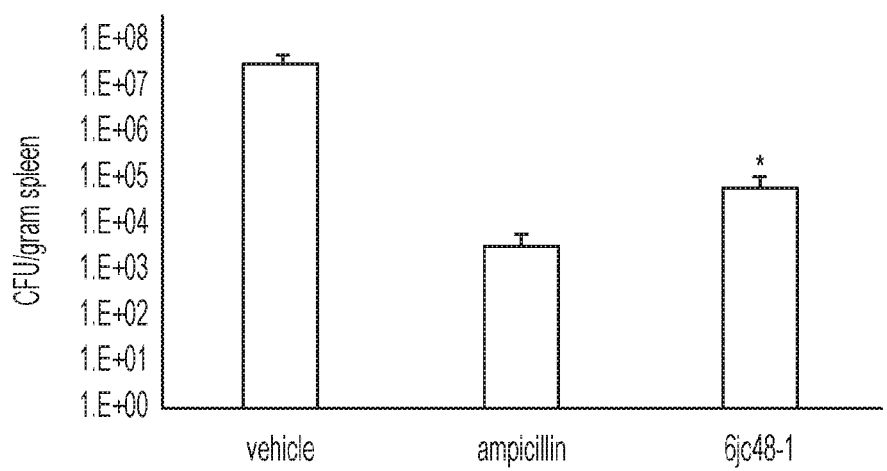
FIG. 13 is bar graph showing the CFU of bacteria per gram of spleen tissue in an animal model of murine sepsis, with the indicated treatments (n=5). The * indicates that one animal treated with compound 6jc48-1 did not survive.

In a separate test, mice (n=5) were inoculated intraperitoneally with *E. faecalis* EF1509 (approximately $5 \times 10^8$ CFU/animal) and treated after 30 minutes with compound 6jc48-1 (100 mg/kg IP), ampicillin (300 mg/kg IP) or a vehicle control. Animals were monitored for survival. After 24 hours, spleen samples were collected and analyzed for the presence of bacteria. Bacterial counts were determined by plating serial dilutions on BHI agar plates and compared to control treatments as measures of efficacy. The results are presented in FIG. 13. None of the animals treated with vehicle survived for the duration of the experiment. Four out of five animals treated with compound 6jc48-1 and all animals treated with ampicillin survived for the duration of the experiment. Bacterial counts measured in spleen revealed significant bacterial clearance for both drugs, indicating in vivo antibiotic efficacy.

REFERENCES

All references cited herein are hereby incorporated by reference in their entirety.

1. Allen et al., *Inhibition of peptidoglycan biosynthesis in vancomycin-susceptible and-resistant bacteria by a semi-synthetic glycopeptide antibiotic*. Antimicrob. Agents Chemother. 40(10):2356-2362, 1996.
2. Anders and Huber, *Differential expression analysis for sequence count data*. Genome Biol. 11(10):R106, 2010.
3. Anders et al., *HTSeq—a Python framework to work with high-throughput sequencing data*. Bioinformatics 31(2): 166-169, 2015.
4. Arias and Murray, *The rise of the Enterococcus: beyond vancomycin resistance*. Nat. Rev. Microbiol. 10(4): p. 266-278, 2012.
5. Åqvist et al., *A new method for predicting binding affinity in computer-aided drug design*. Protein Eng. 7:385-391, 1994.
6. Belley et al., *Ultrastructural effects of oritavancin on methicillin-resistant Staphylococcus aureus and vancomycin-resistant Enterococcus*. Antimicrob. Agents Chemother. 53(2):800-804, 2009.
7. Best et al., *Optimization of the additive CHARMM all-atom protein force field targeting improved sampling of the backbone φ, ψ and side-chain χ1 and χ2 dihedral angles*. J. Chem. Theory and Comp. 8:3257-3273, 2012.
8. Breukink et al., *Use of the cell wall precursor lipid II by a pore forming peptide antibiotic*. Science 286(5448): 2361-2364, 1999.
9. Breukink et al., *Lipid II is an intrinsic component of the pore induced by nisin in bacterial membranes*. J. Biol. Chem. 278(22):19898-19903, 2003.
10. Breukink and de Kruijff, *Lipid II as a target for antibiotics*. Nat. Rev. Drug Discov. 5(4):321-332, 2006.
11. Brooks, et al., *CHARMM: the biomolecular simulation program*. J. Comput. Chem. 30(10):1545-1614, 2009.

12. Bush and Bradford, *Beta-Lactams and beta-Lactamase Inhibitors: An Overview*. Cold Spring Harbor Perspect. Med. 2016:6:a025247.
13. Butler et al., *Antibacterial activity and mechanism of action of a novel anilinouracil-fluoroquinolone hybrid compound*. Antimicrob. Agents Chemother. 51(1):119-127, 2007.
14. Cardona and Wilson, *Skin and soft-tissue infections: a critical review and the role of telavancin in their treatment*. Clin. Infect. Dis. 61 Suppl 2:S69-78, 2015.
15. CLSI, *Methods for Dilution Antimicrobial Susceptibility Tests for Bacteria That Grow Aerobically; Approved Standard—Tenth Edition*. CLSI document M07-A10. Wayne, Pa.: Clinical and Laboratory Standards Institute, 2015.
16. Cotsonas and Wu, *Macromolecular synthesis and membrane perturbation assays for mechanisms of action studies of antimicrobial agents*. Curr. Protocols Pharmacol. Chapter 13, Unit 13A 7, 2009.
17. de Leeuw, *Efficacy of the small molecule inhibitor of Lipid II BAS00127538 against Acinetobacter baumannii*. Drug Des. Dev. Ther. 8:1061-1064, 2014.
18. de Leeuw et al., *Functional interaction of human neutrophil peptide-1 with the cell wall precursor lipid II*. FEBS Lett. 584(8):1543-1548, 2010.
19. den Blaauwen et al., *Bacterial cell division proteins as antibiotic targets*. Bioorg. Chem. 55:27-38, 2014.
20. Dengler et al., *Induction kinetics of the Staphylococcus aureus cell wall stress stimulon in response to different cell wall active antibiotics*. BMC Microbiol. 11:16, 2011.
21. Essig et al., *Copsin, a novel peptide-based fungal antibiotic interfering with the peptidoglycan synthesis*. J. Biol. Chem. 289(50):34953-34964, 2014.
22. Fletcher et al., *Structure-activity exploration of a small-molecule Lipid II inhibitor*. Drug Des. Devel. Ther. 9:2383-2394, 2015.
23. Ganz, *Defensins: antimicrobial peptides of innate immunity*. Nat. Rev. Immunol. 3(9):710-720, 2003.
24. Guvench et al., *CHARMM additive all-atom force field for carbohydrate derivatives and its utility in polysaccharide and carbohydrate protein modeling*. J. Chem. Theory Comput. 7(10):3162-3180, 2011.
25. Guvench et al., *CHARMM Additive All-Atom Force Field for Glycosidic Linkages between Hexopyranoses*. J. Chem. Theory Comput. 5(9):2353-2370, 2009.
26. Hanalei et al., *Increase in glutamine-non-amidated mucopeptides in the peptidoglycan of vancomycin-resistant Staphylococcus aureus strain Mu50*. J. Antimicrob. Chemother. 42(3):315-320, 1998.
27. Holland et al., *Clinical management of Staphylococcus aureus bacteremia: a review*. JAMA, 312(13):1330-1341, 2014.
28. Howden et al., *Reduced vancomycin susceptibility in Staphylococcus aureus, including vancomycin-intermediate and heterogeneous vancomycin-intermediate strains: resistance mechanisms, laboratory detection, and clinical implications*. Clin. Microbiol. Rev. 23(1):99-139, 2010.
29. Jorgensen, *Transferable Intermolecular Potential Functions for Waters, Alcohols, and Ethers. Application to Liquid Water*. J. Am. Chem. Soc., 103:335, 1981.
30. Klauda et al., *Update of the CHARMM all-atom additive force field for lipids: validation on six lipid types*. J. Phys. Chem. B, 114(23):7830-7843, 2010.
31. Kuroda et al., *Identification of the up- and down-regulated genes in vancomycin-resistant Staphylococcus aureus strains Mu3 and Mu50 by cDNA differential hybridization method*. Biochem. Biophys. Res. Commun. 269(2):485-490, 2000.
32. Kuroda et al., *Two-component system VraSR positively modulates the regulation of cell-wall biosynthesis pathway in Staphylococcus aureus*. Mol. Microbiol. 49(3):807-21, 2003.
33. Langmead et al., *Ultrafast and memory-efficient alignment of short DNA sequences to the human genome*. Genome Biol. 10(3):R25, 2009.
34. McCallum et al., *Mutational analyses of open reading frames within the vraSR operon and their roles in the cell wall stress response of Staphylococcus aureus*. Antimicrob. Agents Chemother. 55(4):1391-1402, 2011.
35. MacKerell et al., *All-atom empirical potential for molecular modeling and dynamics studies of proteins*. J. Phys. Chem. B, 102:3586-3616, 1998.
36. Munch et al., *Identification and in vitro analysis of the GatD/MurT enzyme-complex catalyzing lipid II amidation in Staphylococcus aureus*. PLoS Pathog, 8(1): e1002509, 2012.
37. Munita et al., *Daptomycin for the treatment of bacteraemia due to vancomycin-resistant enterococci*. Int. J. Antimicrob. Agents, 44(5):387-395, 2014.
38. Munita et al, *Evolving resistance among Gram-positive pathogens*. Clin. Infect. Dis. 1(suppl 2)):548-557, 2015.
39. O'Driscoll and Crank, *Vancomycin-resistant enterococcal infections: epidemiology, clinical manifestations, and optimal management*. Infect. Drug Resist. 8:217-230, 2015.
40. Oeemig et al., *Eurocin, a new fungal defensin: structure, lipid binding, and its mode of action*. J. Biol. Chem. 287(50):42361-42372, 2012.
41. Oppedijk et al., *Hit'em where it hurts: The growing and structurally diverse family of peptides that target lipid-II*. Biochim Biophys. Acta (5):947-957, 2015.
42. Overton et al., *Global network analysis of drug tolerance, mode of action and virulence in methicillin-resistant S. aureus*. BMC Syst. Biol. 5:68, 2011.
43. Paradise et al., *Cytochrome P450 inhibition assays using traditional and fluorescent substrates*. Curr. Protoc. Pharmacol., 2007. Chapter 7: p. Unit7 11.
44. Pietiainen et al., *Transcriptome analysis of the responses of Staphylococcus aureus to antimicrobial peptides and characterization of the roles of vraDE and vraSR in antimicrobial resistance*. BMC Genomics. 10:429, 2009.
45. Roberts et al., *Dalbavancin and Oritavancin: An Innovative Approach to the Treatment of Gram-Positive Infections*. Pharmacotherapy, 35(10):935-948, 2015.
46. Sass et al., *Human beta-defensin 3 inhibits cell wall biosynthesis in Staphylococci*. Infect. Immun. 78(6): 2793-2800, 2010.
47. Scherl et al., *Exploring glycopeptide-resistance in Staphylococcus aureus: a combined proteomics and transcriptomics approach for the identification of resistance-related markers*. BMC Genomics, 7:296, 2006.
48. Schmitt et al., *Insight into invertebrate defensin mechanism of action: oyster defensins inhibit peptidoglycan biosynthesis by binding to lipid II*. J. Biol. Chem. 285 (38):29208-29216, 2010.
49. Schneider and Sahl, *Lipid II and other bactoprenol-bound cell wall precursors as drug targets*. Curr. Opin. Investig. Drugs 11(2):157-164, 2010.
50. Schneider et al., *Plectasin, a fungal defensin, targets the bacterial cell wall precursor Lipid II*. Science 328(5982): 1168-1172, 2010.

51. Tran et al., *Mechanisms of drug resistance: daptomycin resistance*. Ann. N. Y. Acad. Sci. 1354(1):32-53, 2015.
52. van Heijenoort, *Lipid intermediates in the biosynthesis of bacterial peptidoglycan*. Microbiol. Mol. Biol. Rev. 71(4):620-635, 2007.
53. Vanommeslaeghe et al., *CHARMM general force field: A force field for drug-like molecules compatible with the CHARMM all-atom additive biological force fields*. J. Comp. Chem., 31(4):671-690, 2010.
54. Vanommeslaeghe and Mackerell, *Automation of the CHARMM General Force Field (CGenFF) I: Bond Perception and Atom Typing*. J. Chem. Inf. Model. 52(12):3144-3154, 2012.
55. Vanommeslaeghe et al., *Automation of the CHARMM General Force Field (CGenFF) Assignment of Bonded Parameters and Partial Atomic Charges*. J. Chem. Inf. Model. 52(12):3155-3168, 2012.
56. Varney et al., *Turning defense into offense: defensin mimetics as novel antibiotics targeting lipid II*. PLoS Pathog. 9(11):e1003732, 2013.
57. Vollmer et al., *Peptidoglycan structure and architecture*. FEMS Microbiol. Rev. 32(2):149-167, 2008.

What is claimed is:

1. A compound selected from the group consisting of:

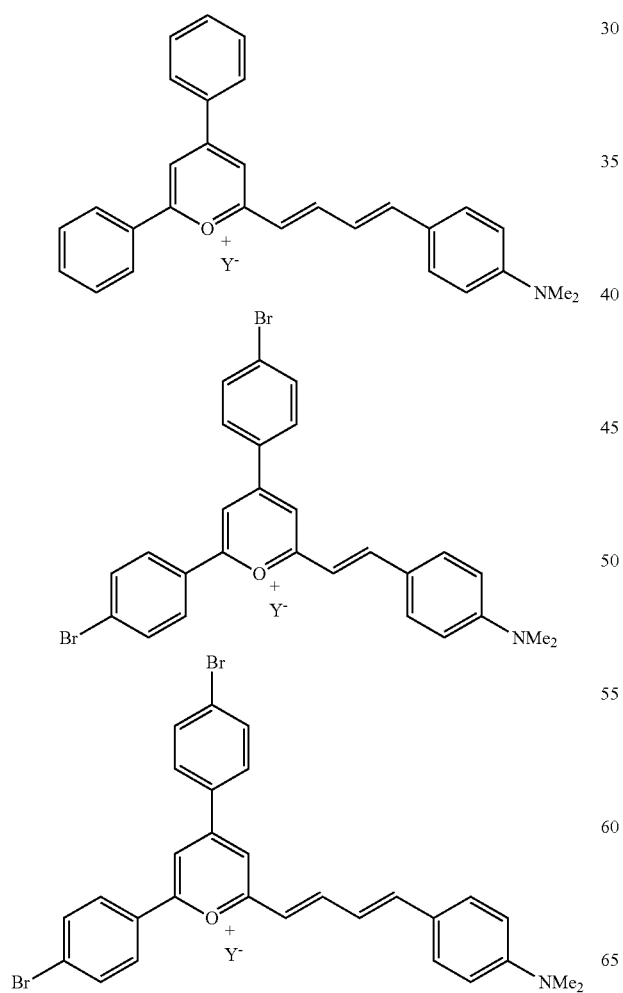

-continued

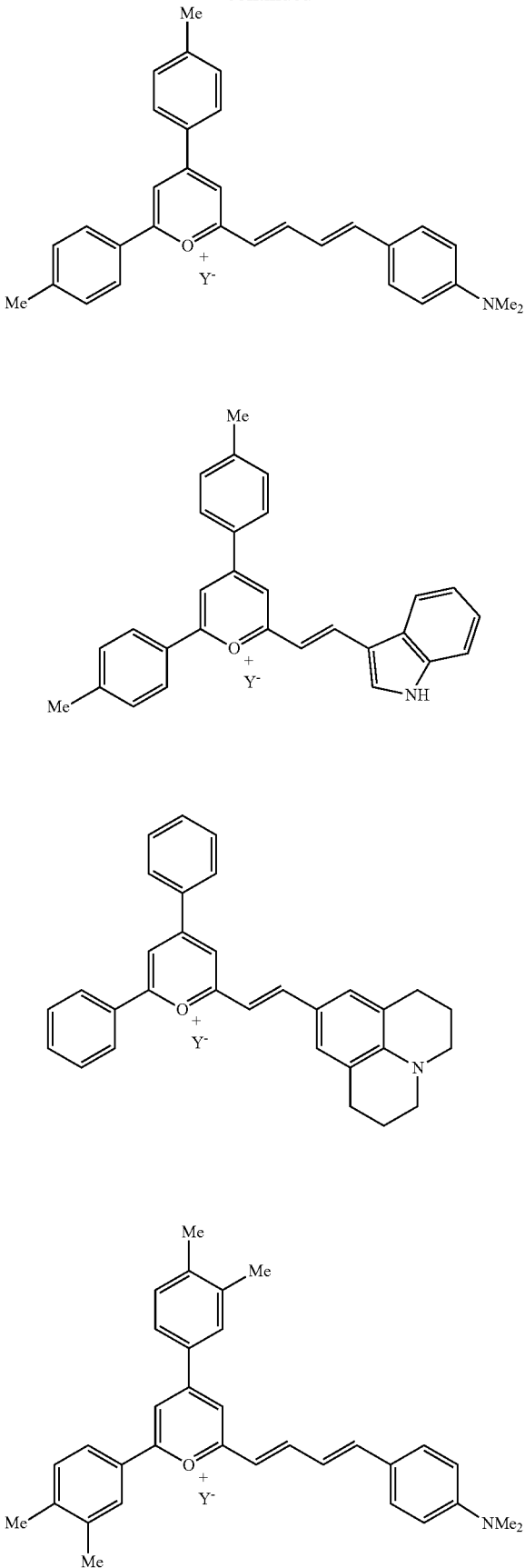

| 119 | 120 |
|---|---|
| -continued | -continued |
| 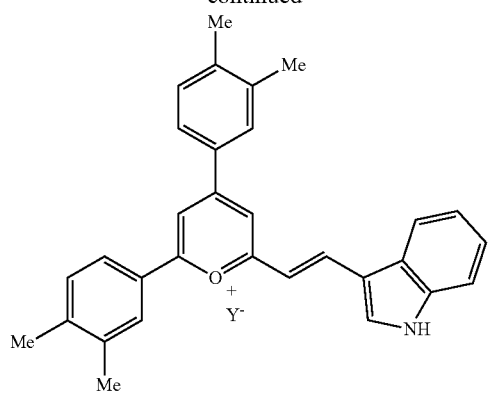 | 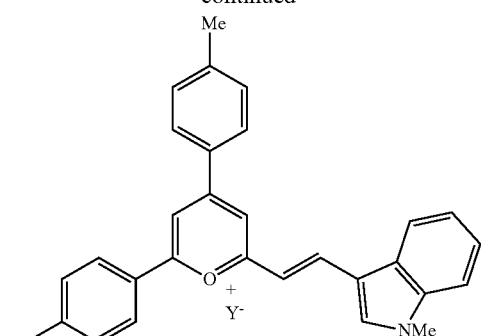 |
| 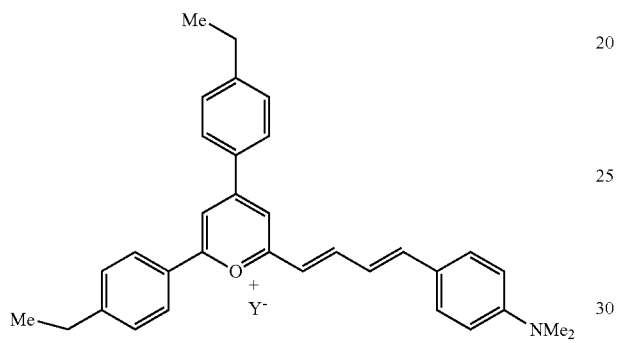 | 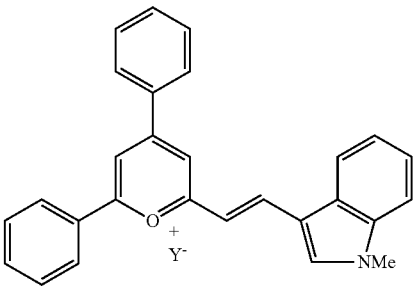 |
| 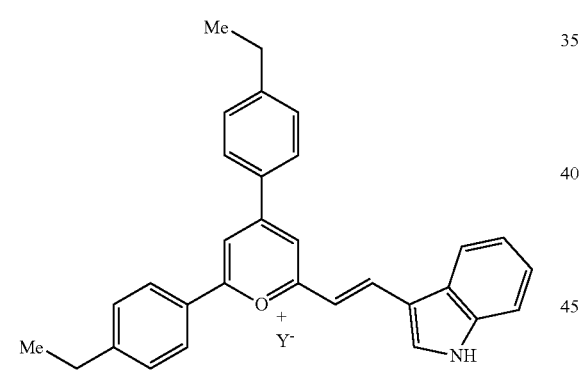 | 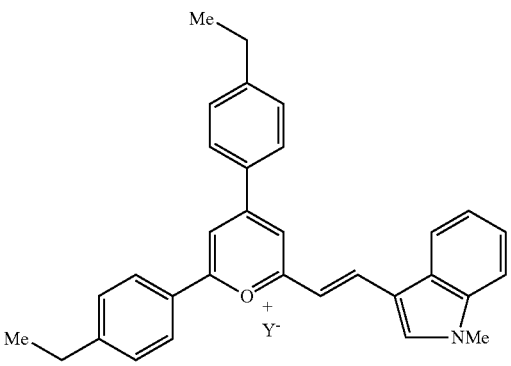 |
| 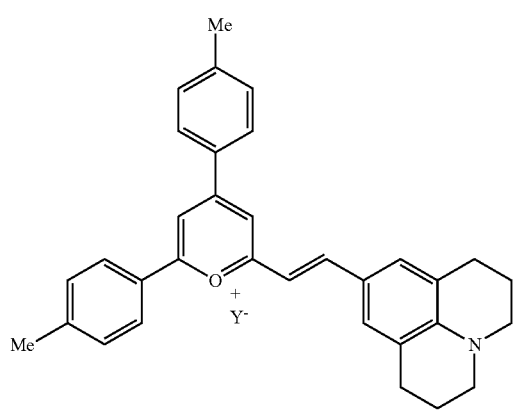 | 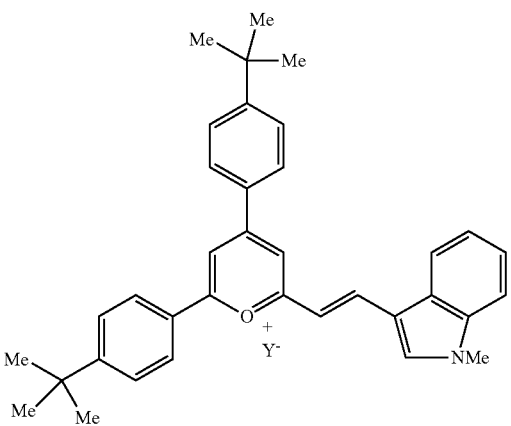 |

121
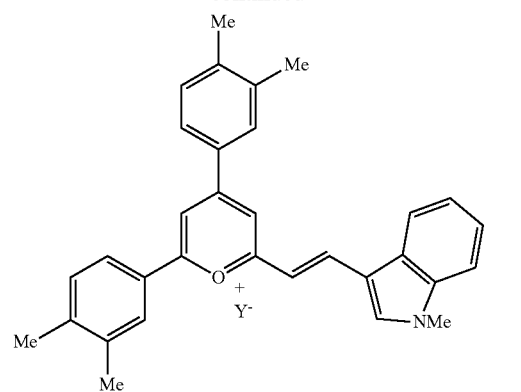
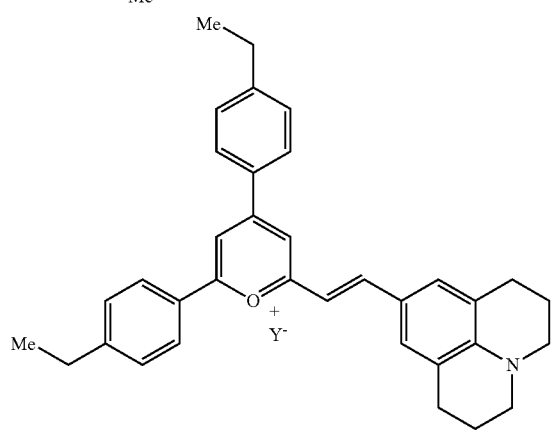
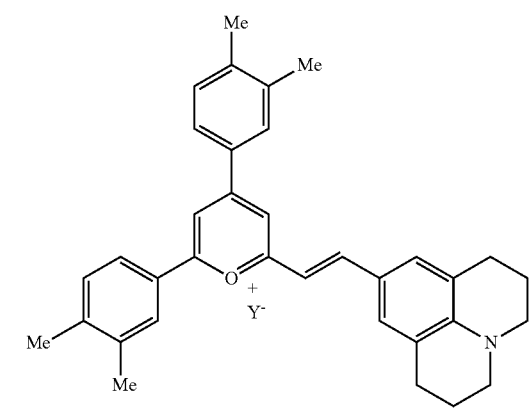
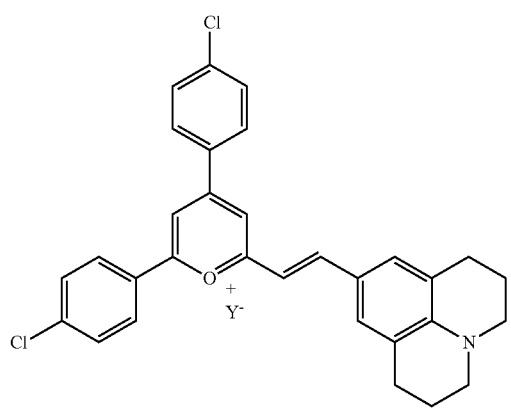
122
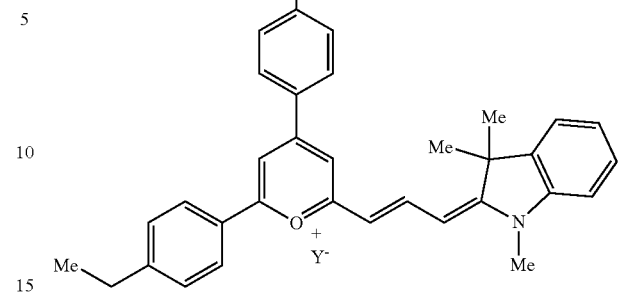
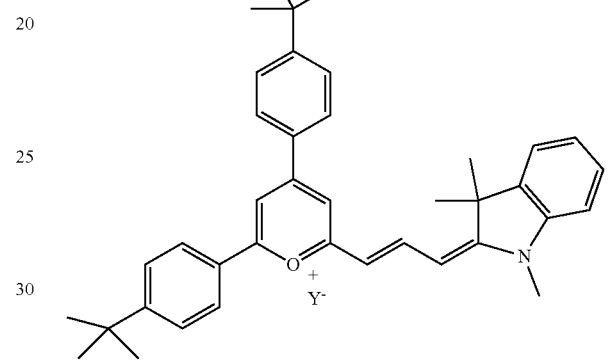
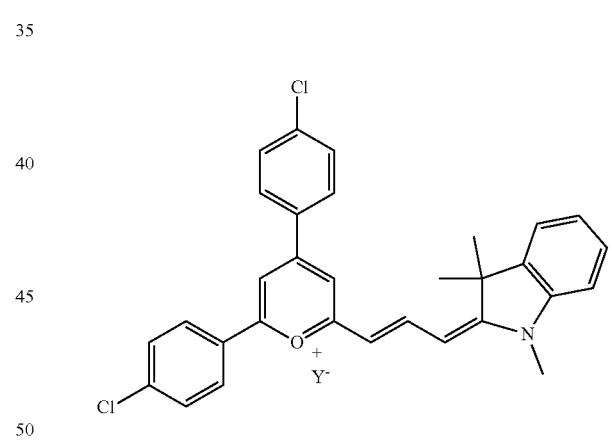
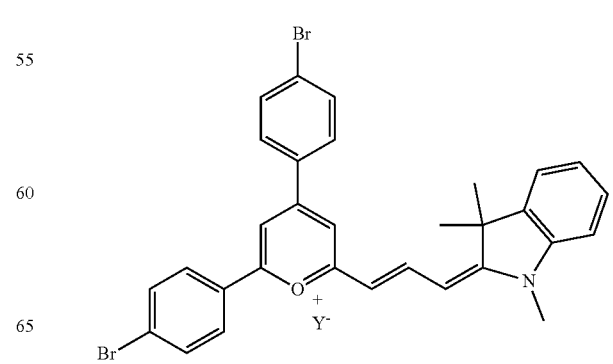

123
-continued
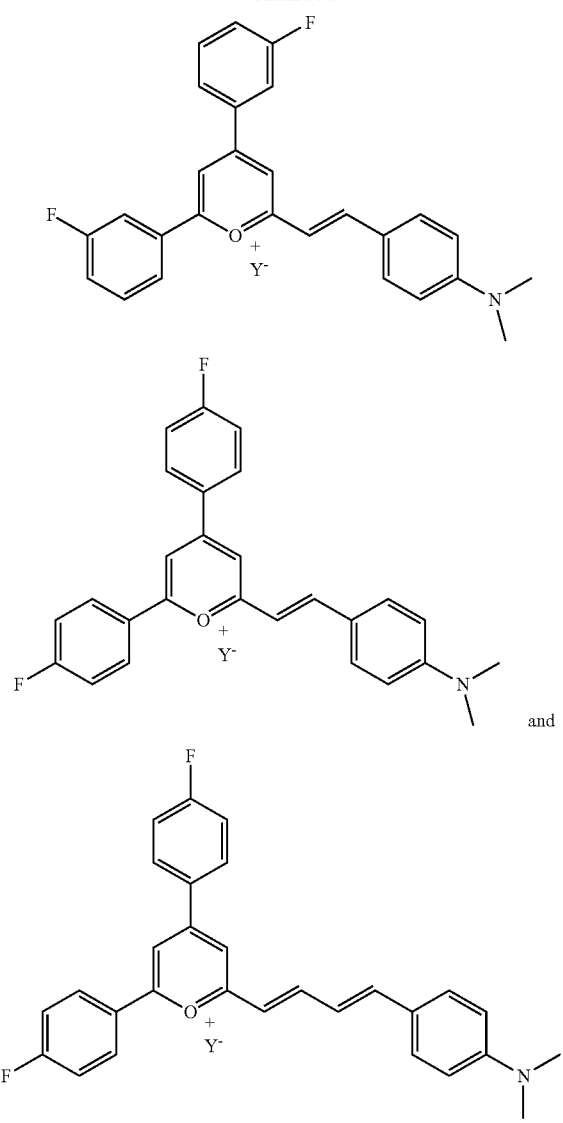
wherein Y is an anion.
2. The compound of claim 1 wherein Y is $BF_4^-$.
3. A compound of claim 1 selected from the group consisting of:
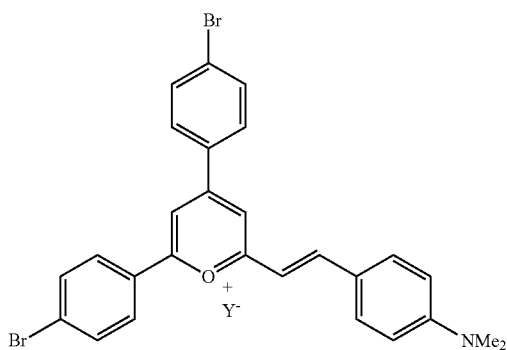
124
-continued
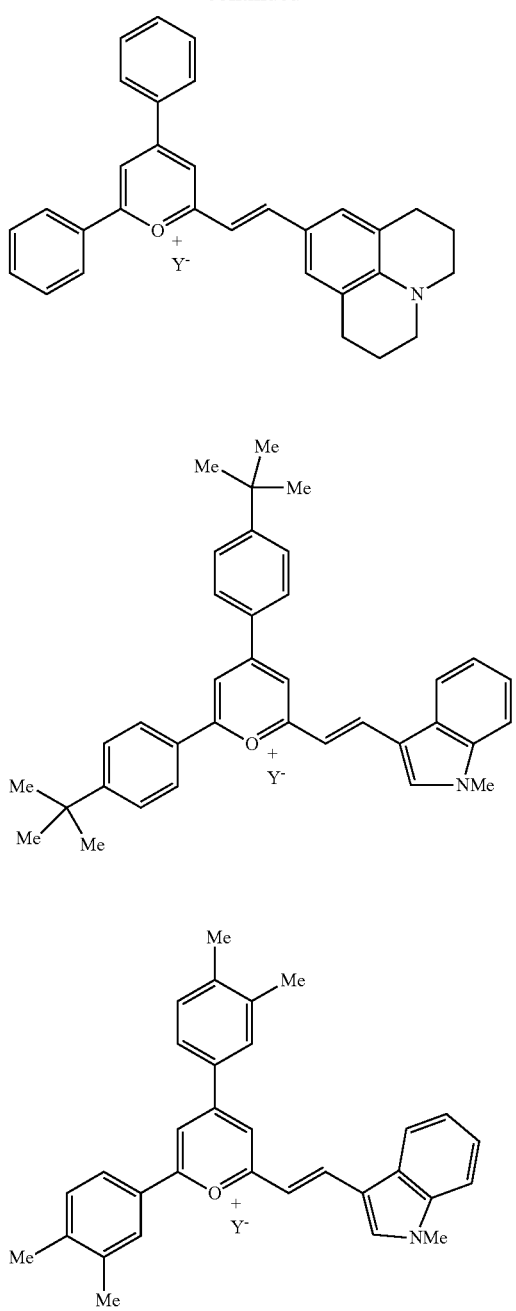
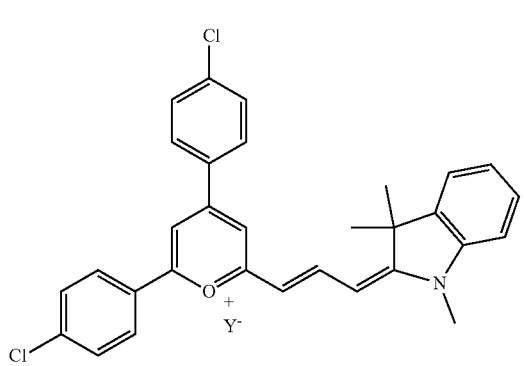

-continued
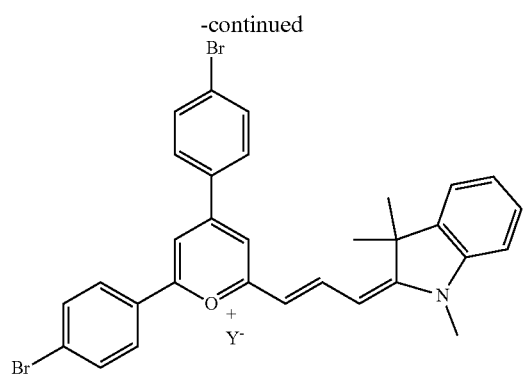
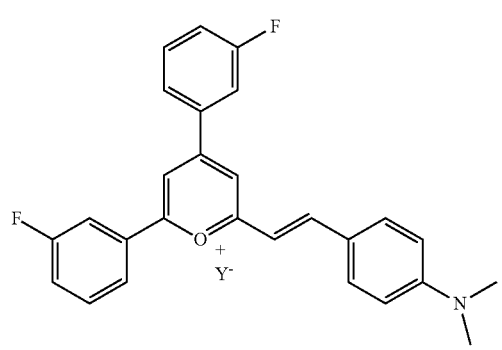
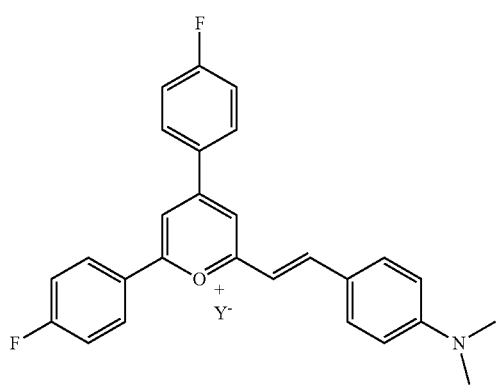
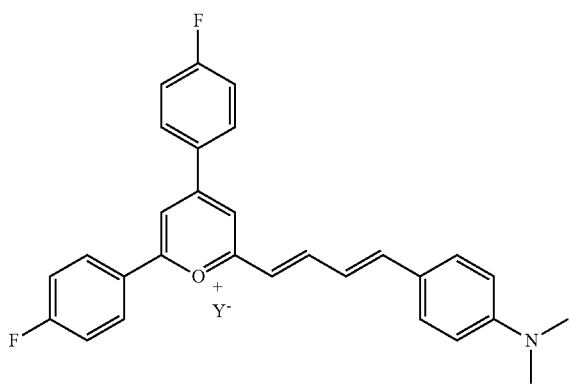
wherein Y is an anion.
4. The compound of claim 3 wherein Y is $BF_4^-$.
5. A compound of claim 1 selected from the group consisting of:
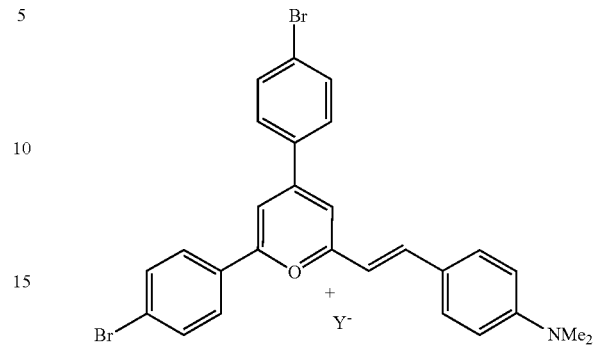
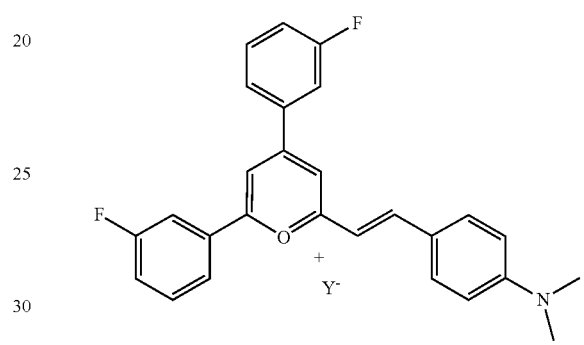
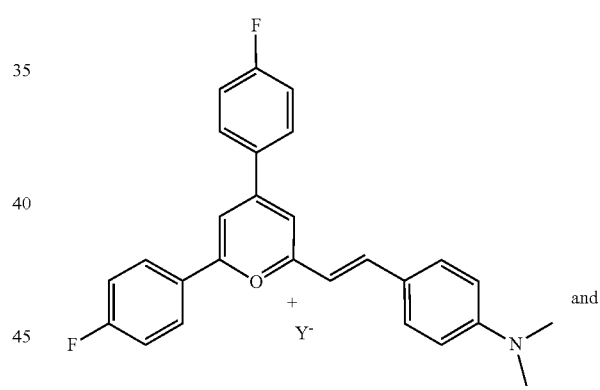
and
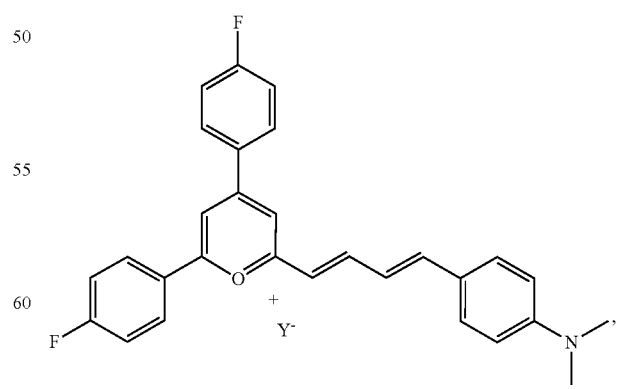
wherein Y is an anion.
6. The compound of claim 5 wherein Y is $BF_4^-$.

7. The compound of claim 1 which is:

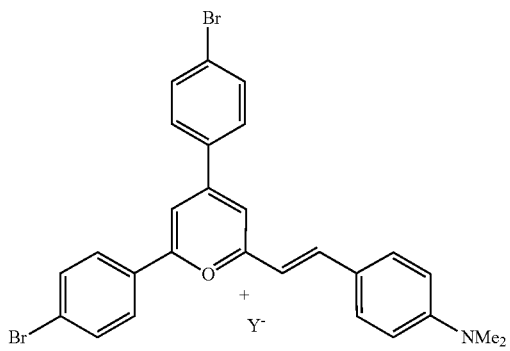

Y⁻ is an anion.

8. The compound of claim 7 wherein Y is $BF_4^-$.

9. A pharmaceutical composition comprising a pharmaceutically acceptable vehicle and a compound of claim 1.

10. A pharmaceutical composition comprising a pharmaceutically acceptable vehicle and a compound of claim 3.

11. A pharmaceutical composition comprising a pharmaceutically acceptable vehicle and a compound of claim 5.

12. A pharmaceutical composition comprising a pharmaceutically acceptable vehicle and a compound of claim 7.

13. A method of treating a subject in need for bacterial infection, comprising administering to the subject a compound of claim 1.

14. The method of claim 13 wherein the subject suffers from infection with *Enterococcus* spp.

15. The method of claim 14 wherein the *Enterococcus* spp. are selected from the group consisting of *E. faecalis* and *E. faecium*.

16. The method of claim 13 wherein the subject suffers from infection with a bacterium selected from the group consisting of *E. faecalis*, *E. faecium*, *Staphylococcus aureus*, *Bacillus anthracis*, and *Acinetobacter baumanii*.

17. The method of claim 13 wherein the bacterial infection is an infection with an antibiotic-resistant bacterial strain.

18. A method of killing or reducing bacteria comprising contacting the bacteria with a compound of claim 1.

19. A method of killing or reducing bacteria on an object comprising contacting the object with a compound of claim 1.

20. A method of protecting an object from colonization by bacteria comprising contacting the object with a compound of claim 1.

21. A compound according to:

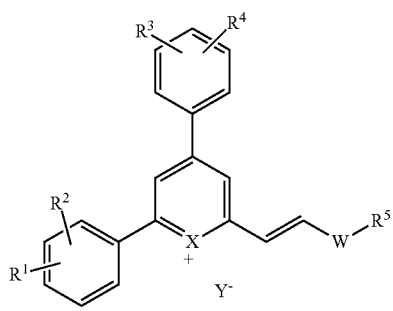

wherein each $R^1$, $R^2$, $R^3$ and $R^4$ independently is H; halogen; trihalomethyl; —$OR^6$; —$NHR^6$; —$NR^6R^6$; $C_1$-$C_6$ alkyl optionally substituted with amino or halo; $C_4$-$C_6$ tert-alkyl; $C_5$-$C_7$ cycloalkyl optionally substituted with amino or halo; $C_4$-$C_6$ cycloheteroalkyl optionally substituted with amino or halo; aryl optionally substituted with amino or halo; or heteroaryl optionally substituted with amino or halo, wherein each $R^6$ independently is H, $C_1$-$C_6$ alkyl, $C_5$-$C_7$ cycloalkyl, $C_4$-$C_6$ cycloheteroalkyl, aryl or heteroaryl and wherein halo is chloride, fluoride or bromide;

wherein W is a bond, —$CH_2$—, —$CH_2$—$CH_2$—, —CH═CH—, —CH═CH—$CH_2$—, or —$CH_2$—CH═CH—; CH═CH—;

wherein $R^5$ is a tricyclic moiety optionally containing one or more nitrogen heteroatoms, and which is optionally substituted with an amino group, a methyl group, an ethyl group, or a halogen, wherein halo is chloride, fluoride or bromide;

wherein X is O; and wherein Y is an anion.

22. A compound of claim 21, wherein $R^5$ is

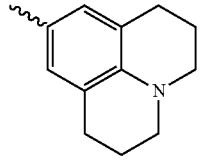

optionally substituted with an amino group, a methyl group, an ethyl group, or a halogen, wherein halo is chloride, fluoride or bromide.

* * * * *